United States Patent
Wagner et al.

(10) Patent No.: US 9,012,419 B2
(45) Date of Patent: Apr. 21, 2015

(54) METHODS AND COMPOSITIONS RELATED TO EOSINOPHIL REGULATION

(75) Inventors: Lori A. Wagner, Salt Lake City, UT (US); Katrin Szardenings, Torrance, CA (US); Gerald J. Gleich, Salt Lake City, UT (US); Tarek Aboul-Fadl Mohamed, Riyadh (SA)

(73) Assignee: University of Utah Research Foundation, Salt Lake City, UT (US)

( * ) Notice: Subject to any disclaimer, the term of this patent is extended or adjusted under 35 U.S.C. 154(b) by 820 days.

(21) Appl. No.: 12/300,894

(22) PCT Filed: May 17, 2007

(86) PCT No.: PCT/US2007/011839
§ 371 (c)(1),
(2), (4) Date: Aug. 17, 2009

(87) PCT Pub. No.: WO2007/136707
PCT Pub. Date: Nov. 29, 2007

(65) Prior Publication Data
US 2010/0016410 A1   Jan. 21, 2010

Related U.S. Application Data

(60) Provisional application No. 60/800,989, filed on May 17, 2006.

(51) Int. Cl.
*A61K 48/00* (2006.01)
*C07H 21/02* (2006.01)
*C07H 21/04* (2006.01)
*C12N 15/113* (2010.01)

(52) U.S. Cl.
CPC .......... *C12N 15/1136* (2013.01); *C12N 15/113* (2013.01); *C12N 2310/111* (2013.01); *C12N 2310/14* (2013.01)

(58) Field of Classification Search
USPC ............................................ 514/44; 536/24.5
See application file for complete search history.

(56) References Cited

U.S. PATENT DOCUMENTS

| | | | |
|---|---|---|---|
| 5,631,267 | A | 5/1997 | Gleich et al. |
| 7,001,595 | B2 | 2/2006 | Salcedo et al. |
| 2006/0040313 | A1 | 2/2006 | Li et al. |

OTHER PUBLICATIONS

Menzies-Gow et al. (Journal of Allergy and Clinical Immunology, 2003 vol. 111, No. 4, pp. 714-719).*
Hammond et al. (Nature Reviews Genetics 2001, vol. 2:110-119).*
Discussion of hypereosinophilic syndrome, provided by http://www.wrongdiagnosis.com. Downloaded on Nov. 30, 2010.*
Wagner et al. Blood. 2007 vol. 109:5191-5198.*
Adachi et al. A Novel Lyn-Binding Peptide Inhibitor Blocks Eosinophil Differentiation, Survival, and Airway Eosinophilic Inflammation. The Journal of Immunology, 1999, vol. 163: 939-946.
Bernard, P. S. & Wittwer, C. T. Real-time PCR technology for cancer diagnostics. Clin Chem 48, 1178-85 (2002).
Bokesh, P.M., C. Post, and G. Strichartz. Structure-activity relationship of lidocaine homologs producing tonic and frequency dependent impulse blockade in nerve. J 46.

(Continued)

*Primary Examiner* — Terra Cotta Gibbs
(74) *Attorney, Agent, or Firm* — Ballard Spahr LLP

(57) ABSTRACT

Disclosed are compositions and methods for regulating eosinophils.

9 Claims, 22 Drawing Sheets

(56) References Cited

OTHER PUBLICATIONS

Figure 3:
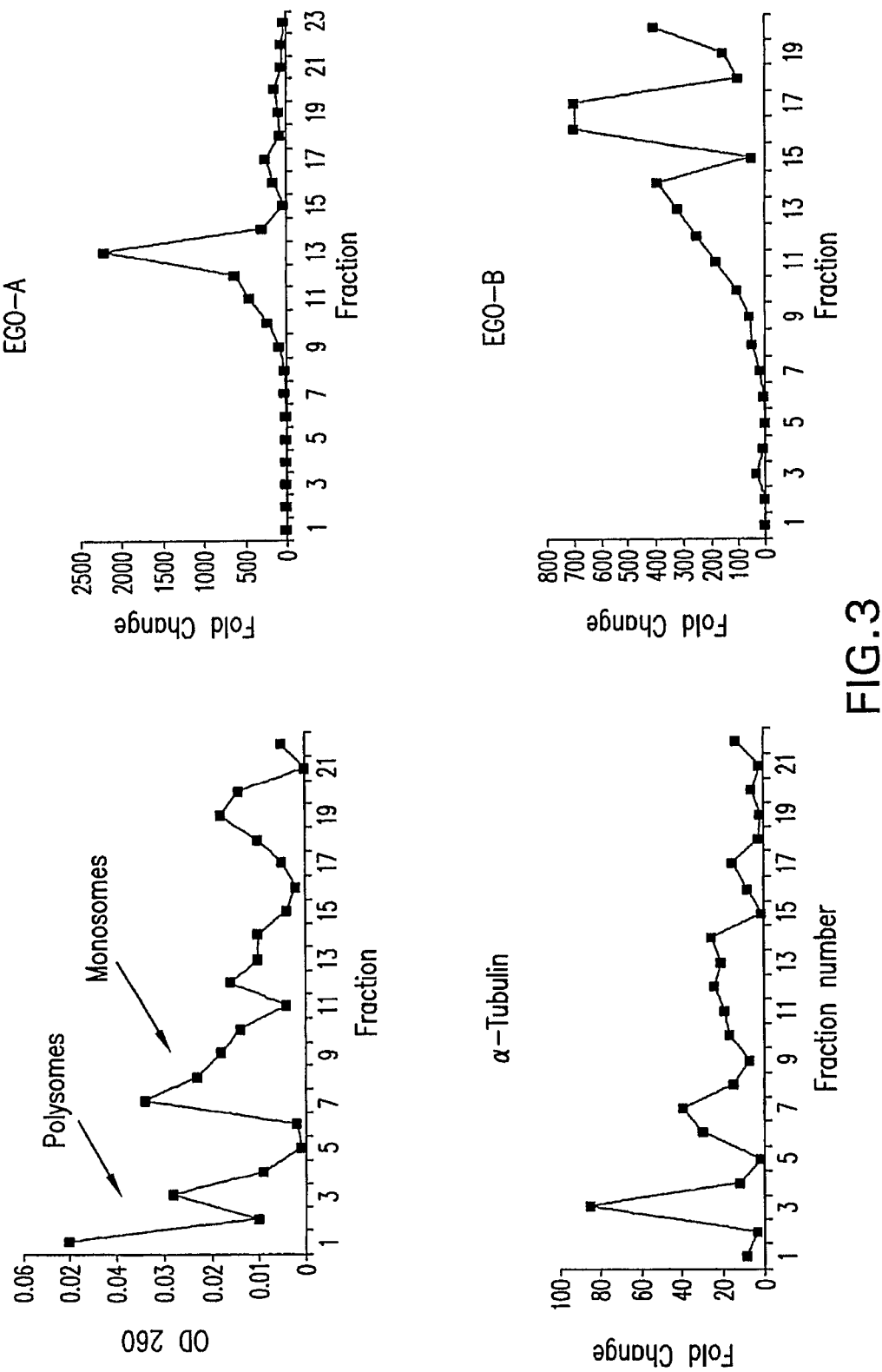

Breitling, R. & Herzyk, P. Rank-based methods as a non-parametric alternative of the T-statistic for the analysis of biological microarray data. J Bioinform Comput Biol 3, 117189 (2005).

Buitenhuis, M. et al. Differential regulation of granulopoiesis by the basic helix-loophelix transcriptional inhibitors Id1 and Id2. Blood 105, 4272-4281 (2005).

Carninci, P. et al. The transcriptional landscape of the mammalian genome. Science 309, 1559-63 (2005).

Claverie, J. M. Fewer genes, more noncoding RNA. Science 309, 1529-30 (2005).

Cockcroft, D.W., Pharmacologic Therapy for Asthma: Overview and Historical Perspective. J Clin Pharmacol, 1999. 35:219-222.

da Costa, J., Olsen, P., De Azereredo Siqueira, R., De Frias Carcalho, V., Serra, M., Alves, L., Faria, R., Xisto, D., Rocco, P., Cordeiro, R., Rodrigues, E., Silva, P., Martins, M. JMF-2, a lidocaine derivative acting on airways spasm and lung allergic inflammation in rats. J Allergy Clin Immunol, 2007. 119(1):219-25.

Decco, M.L., et al. Nebulized lidocaine in the treatment of severe asthma in children: a pilot study. Ann Allergy Asthma Immunol, 1998. 160(8): 4010-7.

Dent, L. A., Strath, M., Mellor, A. L. & Sanderson, C. J. Eosinophilia in transgenic mice expressing interleukin 5. J Exp Med 172, 1425-31 (1990).

Du, J. et al. Novel combinatorial interactions of GATA-1, PU.1, and C/EBPepsilon isoforms regulate transcription of the gene encoding eosinophil granule major basic protein. J Biol Chem 277, 43481-94 (2002).

Elagib, K. E. et al. Jun blockade of erythropoiesis: role for repression of GATA-1 by HERP2. Mol Cell Biol 24, 7779-94 (2004).

Ema, H. et al. Target cells for granulocyte colony-stimulating factor, interleukin-3, and interleukin-5 in differentiation pathways of neutrophils and eosinophils. Blood 76, 195661 (1990).

Foster, P. S., Hogan, S. P., Ramsay, A. J., Matthaei, K. I. & Young, I. G. Interleukin 5 deficiency abolishes eosinophilia, airways hyperreactivity, and lung damage in a mouse asthma model. J Exp Med 183, 195-201 (1996).

Gombart, A. F. et al. Regulation of neutrophil and eosinophil secondary granule gene expression by transcription factors C/EBP epsilon and PU.1. Blood 101, 3265-73 (2003).

Gorska et al. Signaling molecules as therapeutic targets in allergic diseases. J Allergy Clin Immunol,, Aug. 2003, vol. 112(2):241-50.

Haeseler, G., et al. Block of voltage-operated sodium channels by 2,6-dimethylphenol, a structural analogue of lidocaine's aromatic tail. Br J Pharmacol, 2002. 137(2): 285-93.

Hirasawa, R. et al. Essential and instructive roles of GATA factors in eosinophil development. J Exp Med 195, 1379-86 (2002).

Humbles, A. A. et al. A Critical Role for Eosinophils in Allergic Airways Remodeling. Science 305, 1776-9 (2004).

Hunt, L.W., et al. treatment of asthma with nebulized lidocaine: a randomized, placebo-controlled study. J Allergy Clin Immunol, 2004. 113(5): 853-9.

Hunt, L.W., H.A. Swedlund, and G.J. Gleich. Effect of nebulized lidocaine on severe glucocorticoid-dependent asthma. Mayo Clin Proc, 1996. 71(4): 361-8.

Iwasaki, H. et al. Identification of eosinophil lineage-committed progenitors in the murine bone marrow. J Exp Med 201, 1891-7 (2005).

Jungel, A. et al. Expression of interleukin-21 receptor, but not interleukin-21, in synovial fibroblasts and synovial macrophages of patients with rheumatoid arthritis. Arthritis Rheum 50, 1468-76 (2004).

Kitagaki, H. et al. Repeated elicitation of contact hypersensitivity induces a shift in cutaneous cytokine milieu from a T helper cell type 1 to a T helper cell type 2 profile. J Immunol 159, 2484-91 (1997).

Kitamura, T., Tange, T., Terasawa, T., Chiba, S., Kuwaki, T., Miyagawa, K., Piao, YR, Miyazono, K., Urabe, A., Takaku, F. Establishment and characterization of a unique human cell line that proliferates dependently on GM-CSF, IL-3, or erythropoietin. JCell Physiol, 1989. 140(2): 323-334.

Kopf, M. et al. IL-5-deficient mice have a developmental defect in CD5+ B-1 cells and lack eosinophilia but have normal antibody and cytotoxic T cell responses. Immunity 4, 15-24 (1996).

Leckie, M.J., et al. Effects of an interleukin-5 blocking monoclonal antibody on eosinophils, airway hyper-responsiveness, and the late asthmatic response. Lancet, 2000. 356(9248): 2144-8.

Lee, J. J. et al. Defining a Link with Asthma in Mice Congenitally Deficient in Eosinophils. Science 305, 1773-6 (2004).

Lee, N. A. et al. Expression of IL-5 in thymocytes/T cells leads to the development of a massive eosinophilia, extramedullary eosinophilopoiesis, and unique histopathologies. J Immunol 158, 1332-44 (1997).

McKinnon et al. An Interleukin 5 Mutant Distinguishes between Two Functional Responses in Human Eosinophils. JEM, Jul. 7, 1997, vol. 186, No. 1, pp. 121-129.

McNagny, K. & Graf, T. Making eosinophils through subtle shifts in transcription factor expression. J Exp Med 195, F43-7 (2002).

Morahan, G. et al. Association of IL12B promoter polymorphism with severity of atopic and non-atopic asthma in children. Lancet 360, 455-9 (2002).

Nerlov, C. & Graf, T. PU.1 induces myeloid lineage commitment in multipotent hematopoietic progenitors. Genes Dev 12, 2403-12 (1998).

Nerlov, C., McNagny, K. M., Doderlein, G., Kowenz-Leutz, E. & Graf, T. Distinct C/EBP functions are required for eosinophil lineage commitment and maturation. Genes Dev 12, 2413-23 (1998).

Okada, S., et al. Lidocaine and its analogues inhibit IL-5-mediated survival and activation of human eosinophils. J Immunol, 1998. 160(8): 4010-4017.

Okazaki, Y. et al. Analysis of the mouse transcriptome based on functional annotation of 60,770 full-length cDNAs. Nature 420, 563-73 (2002).

Querfurth, E. et al. Antagonism between C/EBPbeta and FOG in eosinophil lineage commitment of multipotent hematopoietic progenitors. Genes Dev 14, 2515-25 (2000).

Ravasi, T. et al. Experimental validation of the regulated expression of large numbers of non-coding RNAs from the mouse genome. Genome Res 16, 11-9 (2006).

Rizzo, M.C., Sole, D., Inhaled corticosteroids in the treatment of respiratory allergy: safety vs. efficacy. J Pediatr, 2006. 82(2): S 198-205.

Rolf, S., et al. Effects of antiarrhythmic drugs on cloned cardiac voltage-gated potassium channels expressed in *Xenopus* oocytes. Naunyn Schmiedebergs Arch Pharmacol, 2000. 362(1): 22-31.

Roquet, A., et al. Combined antagonism of leukotrienes and histamine produces predominant inhibition of allergen-induced early and late phase airway obstruction in asthmatics. Am J respire Crit Care Med, 1997. 155(6):1956-63.

Scheuer, T. Commentary: A Revised View of Local Anesthetic Action: What Channel State Is Really Stabilized? J Gen Physiol, 1999. 113(1): 3-6.

Shi, H. Z. et al. Effect of inhaled interleukin-5 on airway hyperreactivity and eosinophilia in asthmatics. Am J Respir Crit Care Med 157, 204-9 (1998).

Simon, HU. Molecules involved in the regulation o eosinophil apoptosis. Chem Immunol Allergy, 2006. 91:49-58.

Siqueira, J., Costa J., Cordiero, R., Serra, M., Silva, P., Martins, M. Local anesthetic medication for the treatment of asthma. Mem Inst Oswaldo Cruz, 2005. 100(1):161-165.

Tominaga, A. et al. Transgenic mice expressing a B cell growth and differentiation factor gene (interleukin 5) develop eosinophilia and autoantibody production. J Exp Med 173, 429-37 (1991).

Tsunemi, Y. et al. Interleukin-12 p40 gene (IL12B) 3'-untranslated region polymorphism is associated with susceptibility to atopic dermatitis and psoriasis vulgaris. J Dermatol Sci 30, 161-6 (2002).

Usami, A., et al. Theophylline and dexamethasone induce peroxisome proliferator-activated receptor-gamma expression in human eosinophils. Pharmacology. 2006. 77(1):33-37.

Wagner, L.E., 2nd, et al. Meperidine and lidocaine block of recombinant voltage-dependent Na+ channels: evidence that meperidine is a local anesthetic. Anesthesiology, 1999. 91(5): 1481-1490.

Willingham, A. T. et al. A strategy for probing the function of noncoding RNAs finds a repressor of NFAT. Science 309, 1570-3 (2005).

(56) References Cited

OTHER PUBLICATIONS

Yamaguchi, Y. et al. Mechanisms of transcription in eosinophils: GATA-1, but not GATA-2, transactivates the promoter of the eosinophil granule major basic protein gene. Blood 91, 3447-58 (1998).

Yamanaka, R. et al. Impaired granulopoiesis, myelodysplasia, and early lethality in CCAAT/enhancer binding protein epsilon-deficient mice. Proc Natl Acad Sci U S A 94, 13187-92 (1997).

Yu, P., Ma, D. & Xu, M. Nested genes in the human genome. Genomics 86, 414-22 (2005).

Zhang, D. E. et al. Absence of granulocyte colony-stimulating factor signaling and neutrophil development in CCAAT enhancer binding protein alpha-deficient mice. Proc Natl Acad Sci U S A 94, 569-74 (1997).

Zimmermann, N., Colyer, J. L., Koch, L. E. & Rothenberg, M. E. Analysis of the CCR3 promoter reveals a regulatory region in exon 1 that binds GATA-1. BMC Immunol 6, 7 (2005).

Zon et al. Expression of mRNA for the GATA-binding proteins in human eosinophils and basophils: potential role in gene transcription? The American Society of Hematology, Jun. 15, 1993 vol. 81, Iss 12, pp. 3234-3241.

Groeben, H., et al., Airway anesthesia alone does not explain attenuation of histamine-induced bronchospasm by local anesthetics: a comparison of lidocaine, ropivacaine, and dyclonine. Anesthesiology, 94:423-8 (2001).

Kita, H., Adolphson, C. R. & Gleich, G. J. in Middleton's Allergy: Principles & Practice (eds. Adkinson, N. F., Jr. et al., Mosby, Philadelphia), vol. 1, pp. 305-332 (2003).

* cited by examiner

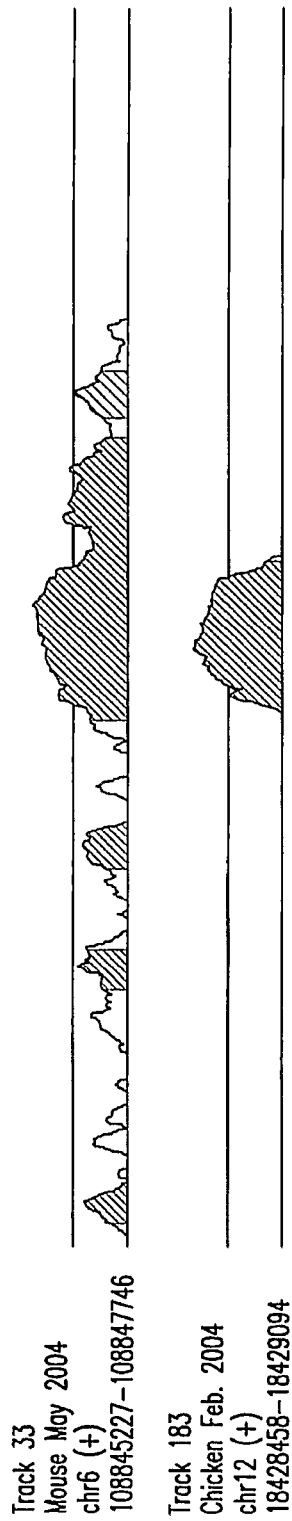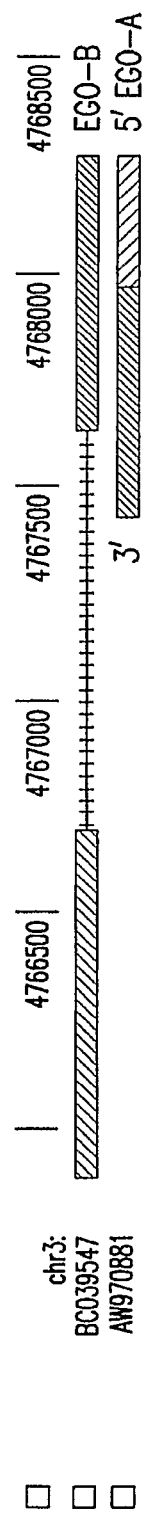
FIG. 1A
FIG. 1B

A.

1 kb →

— 1.7 kb

B. EGO-B splice juction: 4767665 TTCTATCAG....GCACGATGGT 4766655

C. 5' end: 4768205 ATGGAACTAC

FIG.2

0 Hours
Myeloblast Morphology

24 Hours
Promyelocyte

One Week
Metamyelocyte

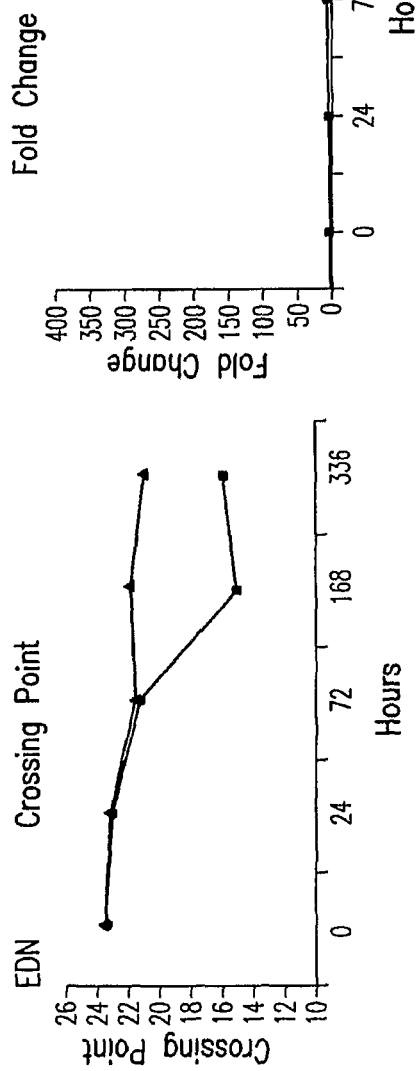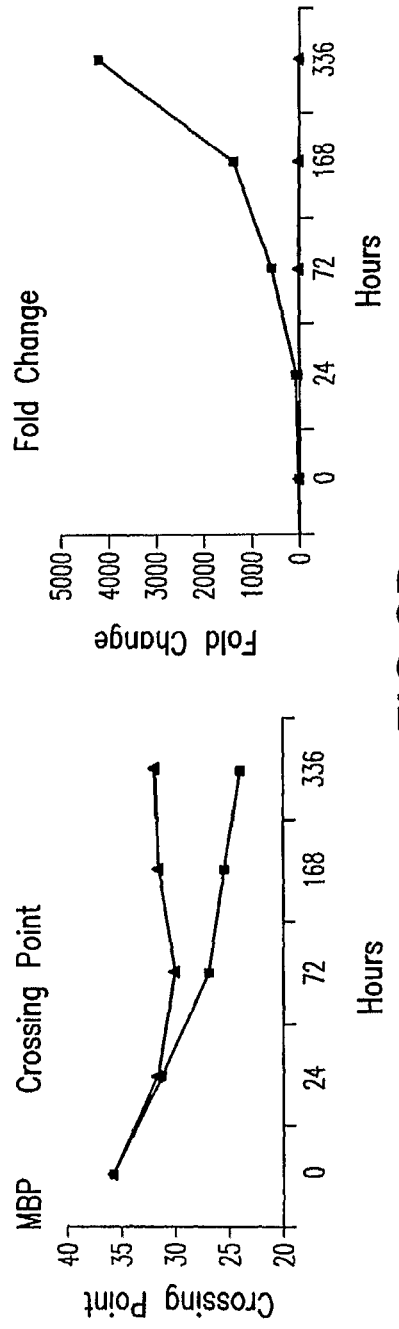
FIG.8A
FIG.8B

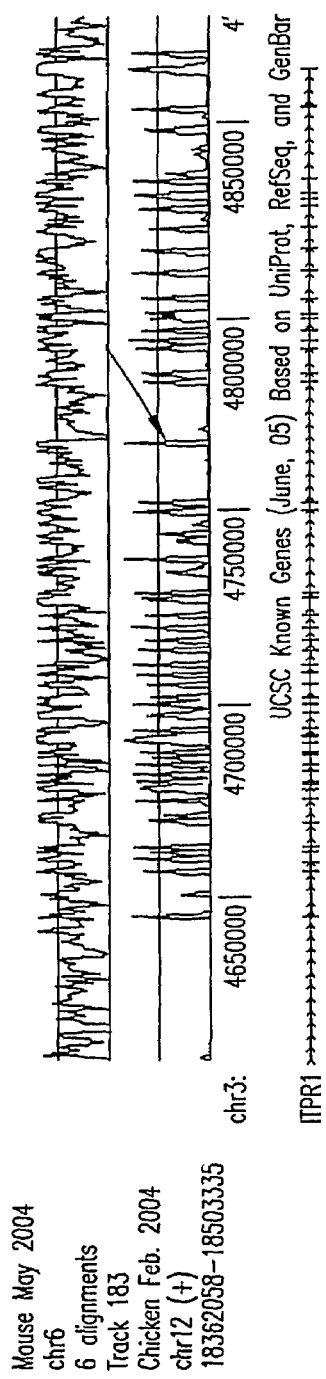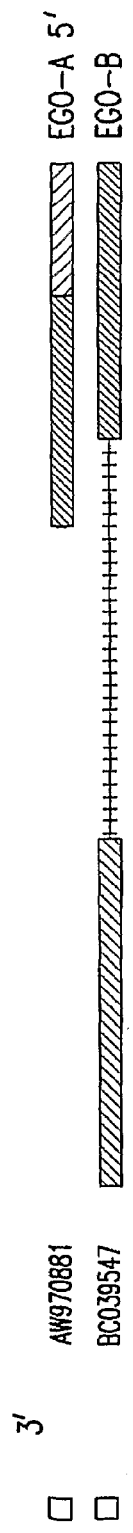
FIG.14A
FIG.14B
FIG.14C

METHODS AND COMPOSITIONS RELATED TO EOSINOPHIL REGULATION

I. PRIORITY

This application claims priority to U.S. Provisional Patent Application No. 60/800,989, which was filed on 17 May 2006.

II. ACKNOWLEDGEMENTS

This invention was made with government support under Public Health Service Grant R01 AI009728. The government has certain rights in this invention.

III. BACKGROUND

Eosinophils are tissue dwelling hematopoietic cell types that play a role in parasitic immunity and allergic disease, such as asthma (Kita et al. 2003). Activated eosinophils secrete toxic basic proteins such as Major Basic Protein (MBP) which are postulated to cause bronchial hyperreactivity, damage of the bronchial mucosa, and remodeling of the airways. Knockout mice with no eosinophils have been shown to lack hallmarks of asthma such as airway hyperresponsiveness, tissue remodeling, and mucous metaplasia (Lee et al. 2004, Humbles et al. 2004).

Eosinophils develop in the bone marrow from hematopoietic stem cells and migrate mainly to the gut or to sites of inflammation. Eosinophils, neutrophils and monocytes have a common progenitor in the myeloid pathway of development. The interplay of several transcription factors, including GATA-1, PU.1, and the CCAAT enhancer binding proteins, c/EBPα and ε, are important to eosinophil development (McNagny et al. 2002, Nerlov et al. 1998, Hirasawa et al. 2002, Zhang et al. 19997). High levels of PU.1 specify myeloid differentiation by antagonizing GATA-1 in the earliest stages of stem cell commitment (Nerlov et al. 1998). In particular, a high affinity GATA-1 binding site within the GATA-1 promoter appears to be critical for eosinophil development; deletion of this binding site in mice specifically abolishes the entire eosinophil lineage (Okazaki et al. 2002). During later stages of eosinophil development, an intermediate level of GATA-1 in synergy with PU.1 directs the formation of the eosinophil lineage by activating dual binding sites in MBP (Du et al. 2002, Gombart et al. 2003, Yamaguchi et al. 1998). GATA-1 also activates the eotaxin receptor CC chemokine receptor-3 promoter and the IL-5Rα gene (Zimmerman et al. 2005). The CCAAT enhancer binding protein, c/EBPα, is important in early myeloid development, whereas c/EBPε plays a later role in granulocyte lineage (Yamanaka et al. 1997). Mice knockouts of c/EBPε affect both neutrophil and eosinophil development at the myelocyte to metamyelocyte stage (Yamanaka et al. 1997). Other genes involved in eosinophil development include the helix-loop-helix transcription factors, Id 1 and 2, and FOG (Friend of GATA). FOG inhibits eosinophil development by interaction with GATA-1 (Querfurth et al. 2000). Id 1 inhibits eosinophil development whereas Id 2 enhances both neutrophil and eosinophil development (Buitenhuis et al. 2005). All of these transcription factors are used in general myeloid development; eosinophil development is regulated by fine tuning of expression levels of individual transcription factors.

The complex interplay of transcription factors is influenced by the cytokines IL-3, GM-CSF and particularly the Th2 cytokine, IL-5. CD34+ hematopoietic cells cultured in IL-5 are exclusively eosinophils after several weeks of culture (Ema et al. 1990). Furthermore, transgenic mice over-expressing IL-5 have a massive eosinophilia, including infiltration into nearly all organ systems (Lee et al. 1997, Dent et al. 1990, Tominaga et al. 1991). However, mice knockouts for IL-5 still have basal levels of eosinophils but do not develop eosinophilia when infected by helminthes or challenged with aeroallergen (Kopf et al. 1996, Foster et al. 1996). Inhalation of IL-5 in human asthmatics causes increased eosinophil numbers and airway hyperreactivity (Kitagaki et al. 1997, Shi et al. 1998). Furthermore, a subset of mouse bone marrow cells expressing the IL-5Rα are eosinophil progenitors (Iwasaki et al. 2005). Therefore, IL-5 is the most important cytokine in eosinophil development but alternative developmental pathways also exist. What is needed in the art is a method of reducing the negative effects of eosinophils.

IV. SUMMARY

Disclosed are methods and compositions related to inhibition of eosinophils.

Disclosed herein is a composition comprising a viral vector, wherein delivery of the vector to a cell inhibits eosinophil development. The vector can comprise a nucleic acid operably linked to an expression control sequence and wherein the nucleic acid inhibits expression of the eosinophil.

Also disclosed is a composition comprising a cell, wherein the cell is a vector.

Also disclosed is a method of inhibiting eosinophil development in a subject comprising administering to the subject a vector.

Disclosed herein is a method of inhibiting eosinophil development in a subject comprising reducing EGO mRNA levels in the subject.

Disclosed is a method of reducing eosinophil-related disease in a subject comprising reducing EGO mRNA levels in the subject.

Also disclosed is a method for preventing or reducing eosinophil development in a subject, comprising administering an eosinophil inhibitor to a subject in need thereof.

Disclosed is a method of screening for a composition that reduces or inhibits eosinophil development comprising the steps of: exposing an IL-5-dependent cell line to a test composition; determining inhibition of growth of the IL-5 dependent cell line, wherein inhibition of growth indicates the test composition that reduces or inhibits eosinophil development.

Further disclosed are compositions identified by the screening methods disclosed herein.

Disclosed is a method of treating or preventing an eosinophil-related disease comprising administering to a subject in need thereof an effective amount of one or more of the compounds of Table 5 or 6.

V. BRIEF DESCRIPTION OF THE DRAWINGS

The accompanying drawings, which are incorporated in and constitute a part of this specification, illustrate several embodiments and together with the description illustrate the disclosed compositions and methods.

FIG. 1 shows conservation and gene structure of EGO. A. Vista tracks of mouse and chicken on the UCSC browser. Y axis values range from a 50% minimum to 100% identity. B. The structure of EGO transcripts is shown. The representative cDNA clones (BC035947 and AW970881) from BLAT are shown. The putative 5' end of EGO A is shown in grey. C. The splice junction of EGO-B in CD34+cells differs from the BC035947 cDNA. D. The putative 5' end of EGO A and B as determined by S1 nuclease protection and PCR.

FIG. 2 shows the structure of EGO transcripts. Autoradiogram of TF-1 cell poly A+ RNA hybridized with radiolabeled probe for EGO-A (1 kb) and EGO-B (1.7 kb). B. Sequenced splice junction of EGO-B. C. 5' end of EGO as determined by PCR.

FIG. 3 shows sucrose gradient fractions. A. OD260 of RNA isolated from sucrose gradient fractions. B. Real time Q-RT-PCR of α-tubulin isolated from sucrose gradient fractions. C. Real time Q-RT-PCR of EGO-A. D. Real time Q-RT-PCR of EGO-B.

Figure 4A:
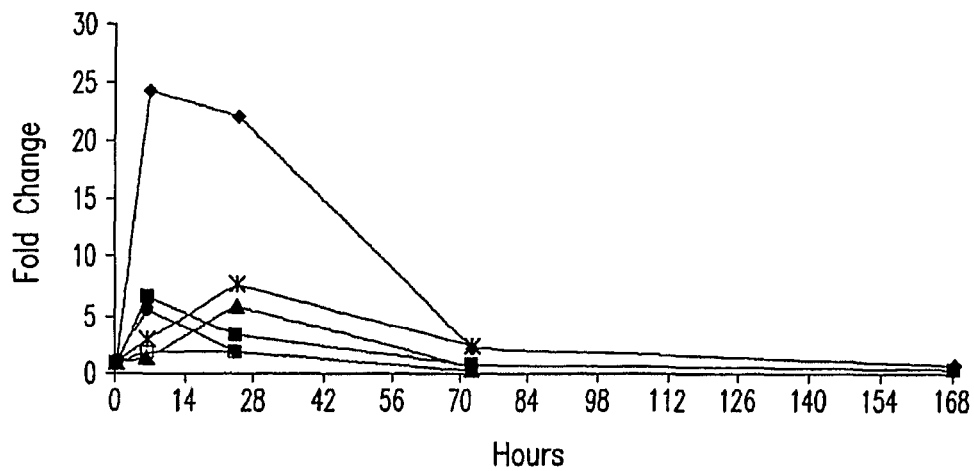
Figure 4B:
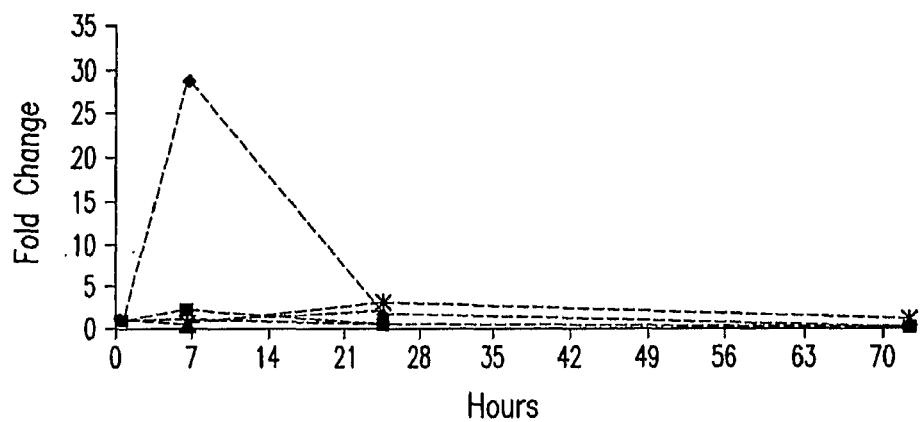

FIG. 4 shows increased expression of EGO transcripts following IL-5 stimulation. A. Quantitative real time RT-PCR of EGO-A transcripts following cytokine stimulation of umbilical cord blood CD34+ cells. B. Quantitative real time RT-PCR of EGO-B transcripts following cytokine stimulation of umbilical cord blood CD34+ cells. C. Q-RT-PCR of EGO transcripts following IL-5 stimulation of bone marrow CD34+ cells. EGO-A, solid line. EGO-B, dashed line. IL-5; filled diamonds, GM-CSF, G-CSF; crosses, epoietin; filled squares, M-CSF, GM-CSF; filled asterisks, SCF: open squares.

FIG. 5 shows quantitative real time RT-PCR of EGO transcripts derived from human tissue. A. Fold change of EGO-A in various tissues relative to brain. B. Fold change of EGO-B relative to brain. CD34+ cells and bone marrow mononuclear cell RNA was normalized to the average level of α-tubulin in the tissue panel. UC CD34+; umbilical cord CD34+, BM CD34+; bone marrow CD34+, BMMC; bone marrow mononuclear cells.

Figure 6A:
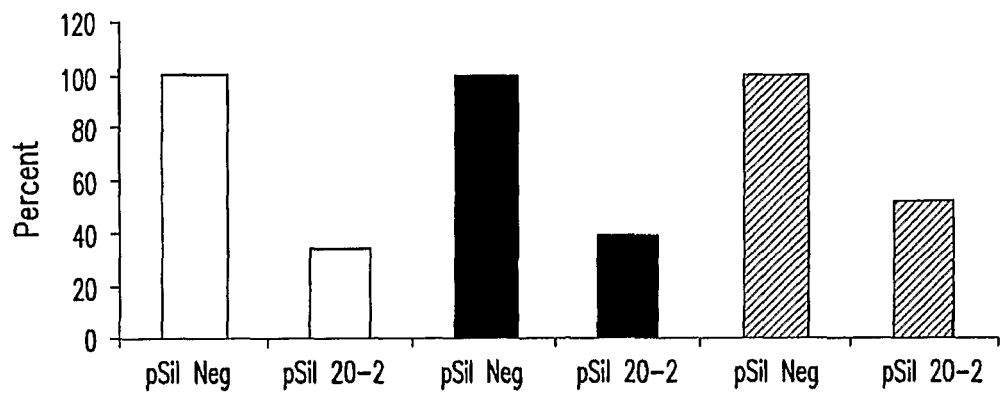
Figure 6B:
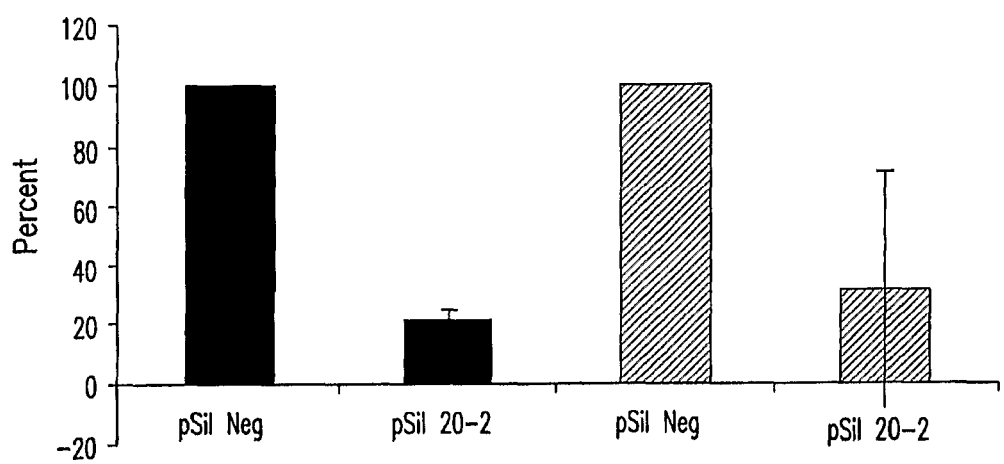

FIG. 6 shows EGO RNA Silencing decreases granule protein transcription. A. TF-1 cells transfected with negative control plasmid, pSi1 Neg or shRNA targeting both EGO transcripts, pSi1 20-2. B. Umbilical cord blood CD34+ cells transfected with negative control plasmid, pSi1 Neg or shRNA targeting both EGO transcripts, pSi1 20-2. White bars are EGO transcript levels, black bars are MBP transcript levels, and grey bars are EDN transcript levels relative to control. These graphs are representative of three experiments for CD34+ cells.

Figure 7A:
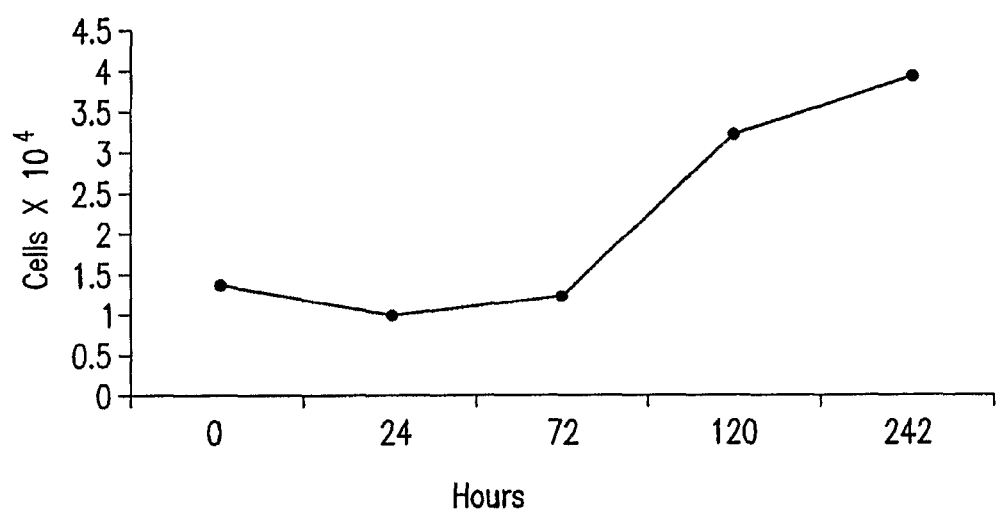

FIG. 7 shows that CD34+ cells were isolated from mononuclear cord blood cells using the Miltenyi Midi Macs System and Direct CD34+ Progenitor Isolation Kit. Cells were cultured in RPMI with glutamine, penicillin/streptomycin, 10% Fetal Calf Serum and 5 ng/ml IL-5. A. Cells were stained with 0.4% trypan blue and live cells were counted on a hemacytometer. B. Cells were cytospun onto slides and stained with Protocol Hema-3 (Fisher-similar to Wright-Giemsa) at various timepoints.

Figure 8C:
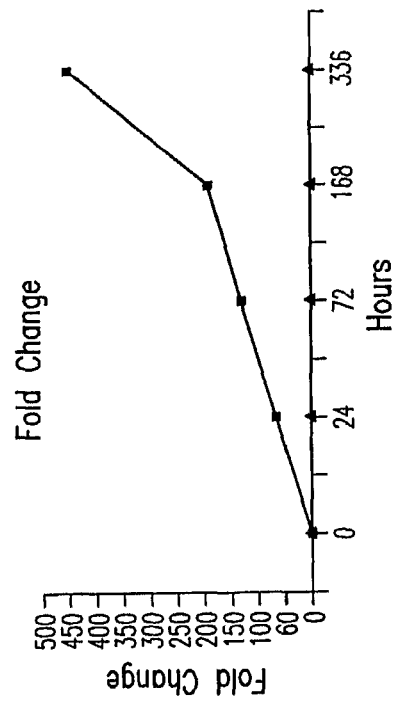
Figure 8C:
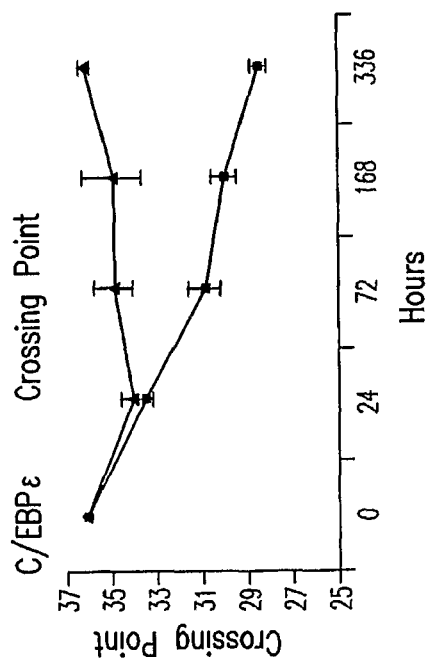

FIG. 8 shows time RT-PCR of transcription factor and granule protein mRNA derived from IL-5 (filled squares) or erythropoietin (triangles) stimulated CD34+ cord blood cells. Total RNA was isolated using the Qiagen Rneasy kit. First strand cDNA was synthesized using the Endofree RT kit (Ambion). PCR conditions were 2 mM dNTPs, 0.5 uM primers, 1/30,000 Sybr Green I, 0.5 UAmplitaq(ABI), 0.1 μg Taqstart antibody (Clontech), 4 mM PCR buffer (Idaho Technology, SLC,UT) and 4 ul 10× diluted cDNA in a 20 ul reaction. PCR was done in triplicate on a Roche LightCycler. Parameters were 94° C. for 0 seconds, 60° C. for 20 seconds, 40 cycles. All reactions are normalized to an α-tubulin control. Efficiency of the α-tubulin primers is 2.0 and efficiency of all other primers is assumed to be 2.0. Crossing point is based on 2nd derivative maximum using LightCycler Data Analysis v3.5. Error bars shown for crossing point are standard deviation from the mean (some error bars are too small to be visible). A. EDN B. MBP C. C/EBPε.

Figure 9A:
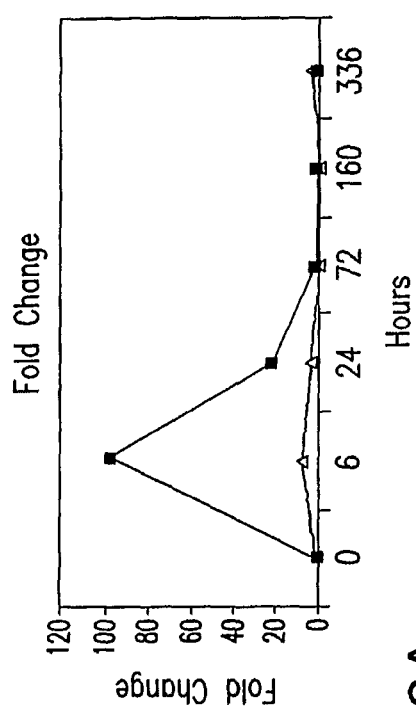
Figure 9B:
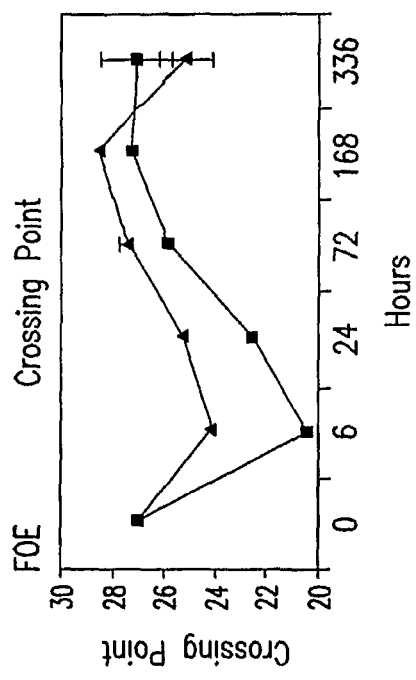
Figure 9B:
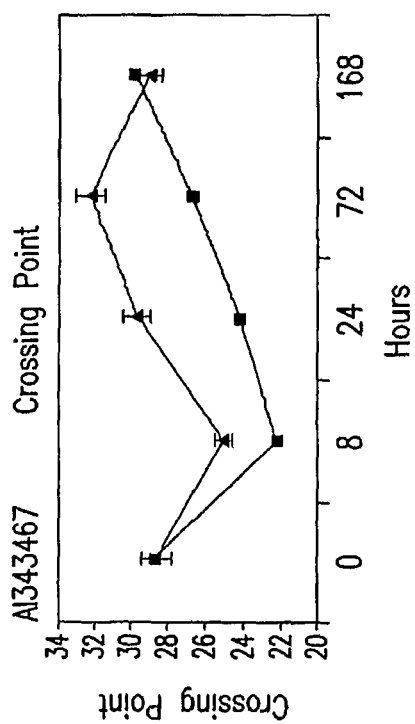

FIG. 9 shows real time RT-PCR of FOE (EGO) and A1343467 mRNA derived from IL-5 (filled squares) or erythropoietin (triangles) stimulated CD34+ cord blood cells. Methods are as in FIG. 8. A. FOE (EGO) B. A1343467. This experiment was done twice with different donors. PCR products were sequenced to verify that the correct gene was amplified.

Figure 10A:
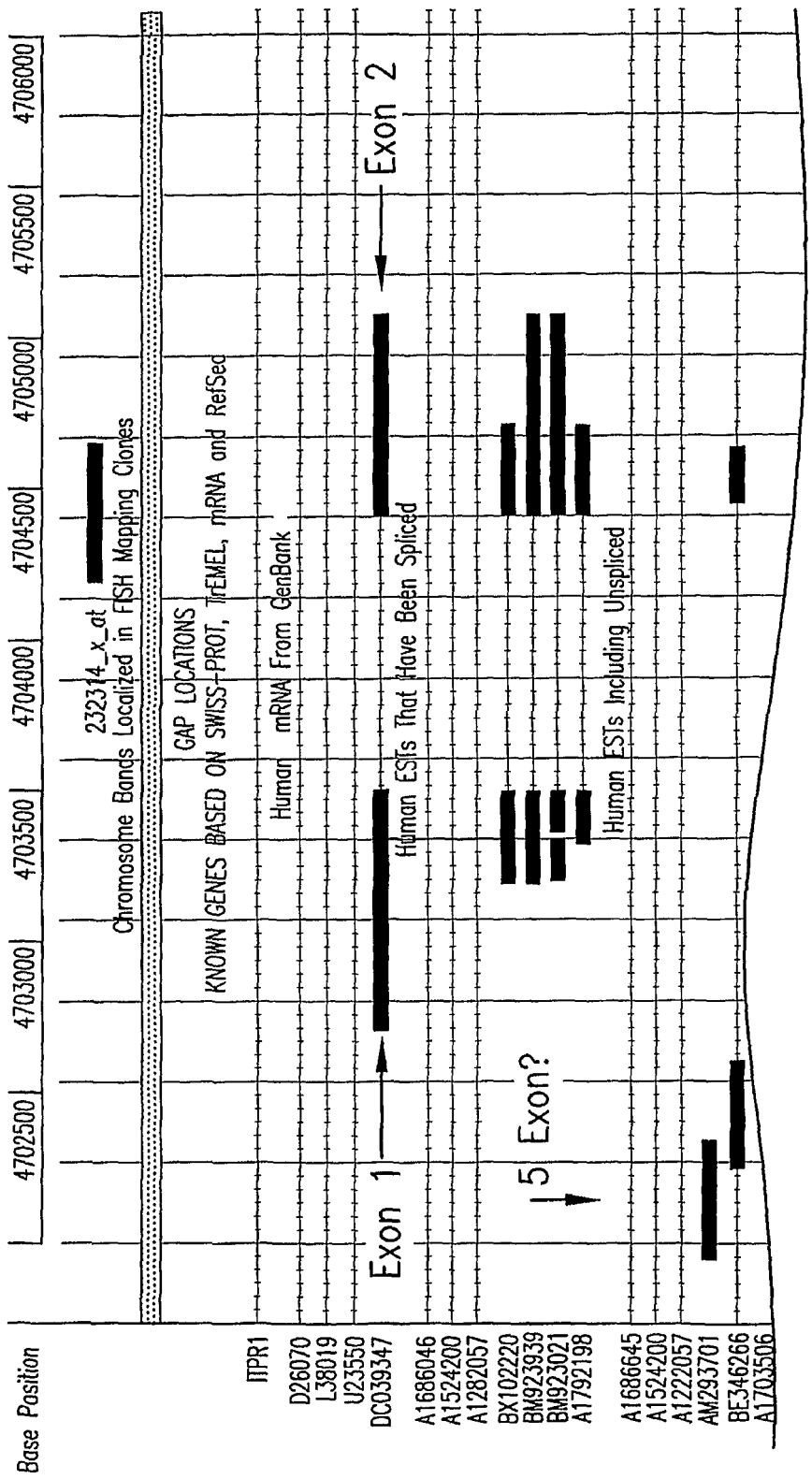
Figure 10B:
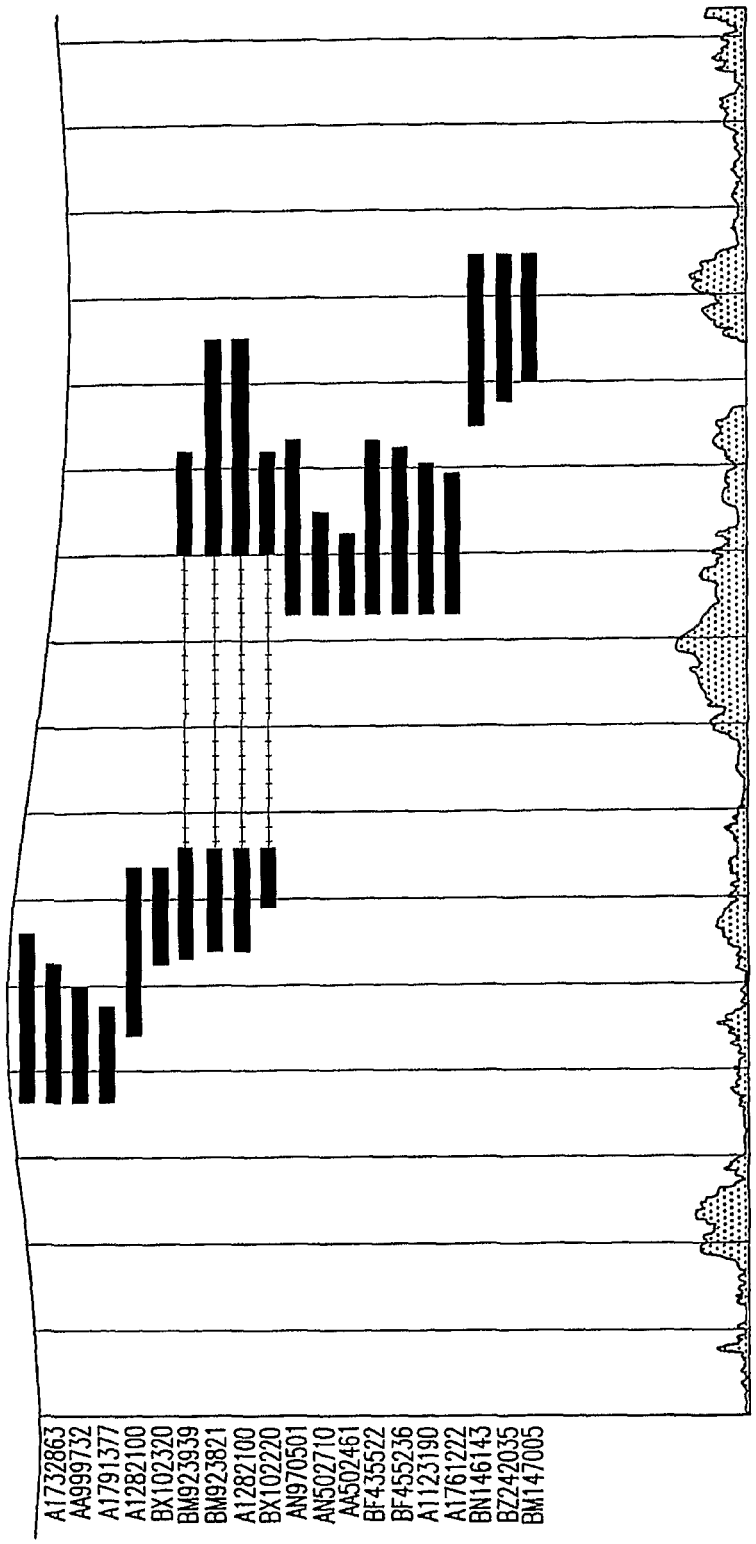

FIG. 10 shows a map of overlapping ESTs and Chromosomal Location of FOE (EGO). EST accession numbers are on the left. Blocks represent transcribed regions. Lines represent introns. Arrows within the lines show the direction of transcription. Mouse conservation is shown on a logarithmic scale.

Figure 11:
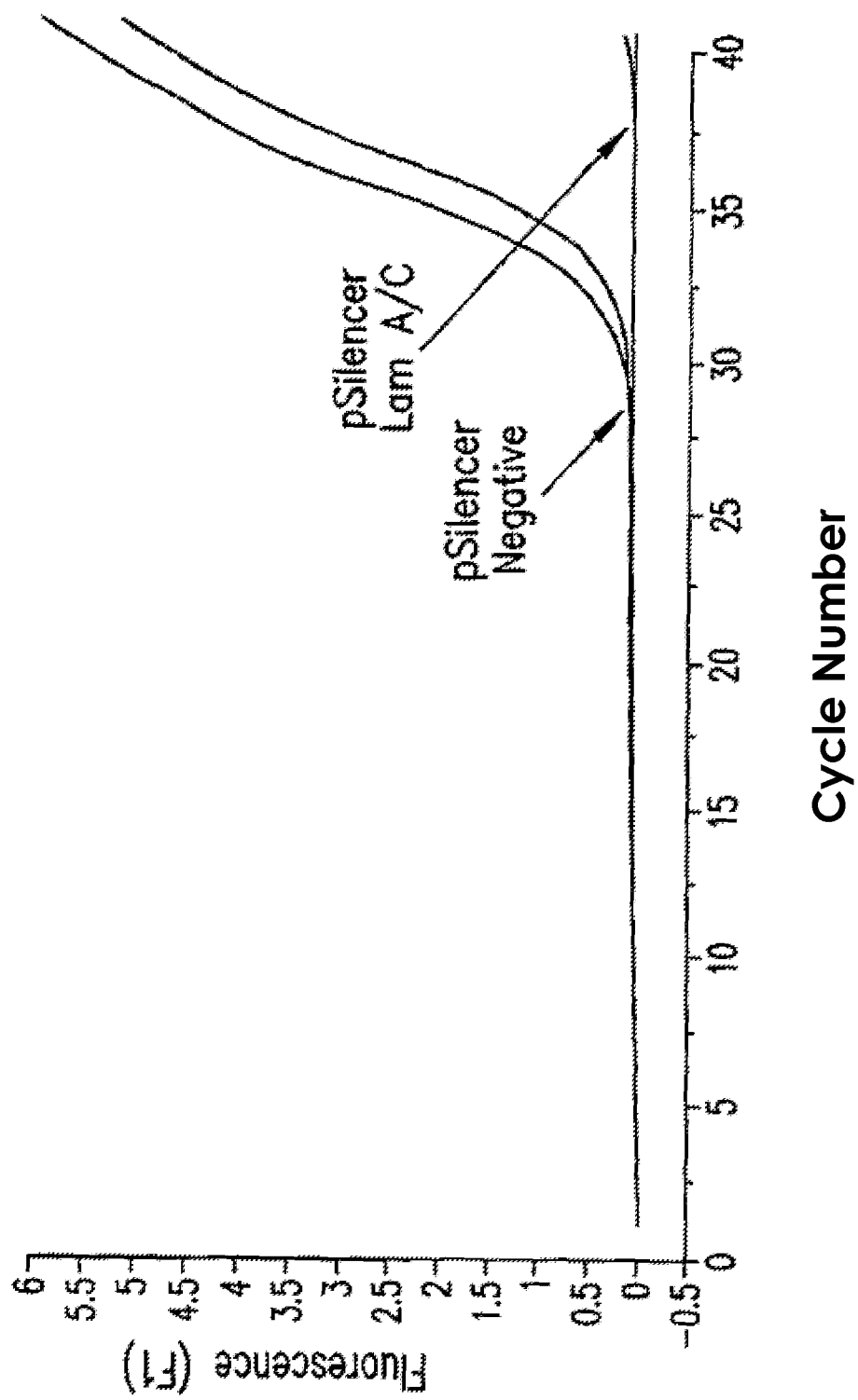

FIG. 11 shows RNA silencing of Lamin A/C. Plasmid DNA (1.0 μg) was electroporated in duplicate into 5-8×105 CD34+ cells using the CD34+ Nucleofector kit and a Nucleofector device (Amaxa) set on program U8. Cells were put in one well each of a 24 well plate and RPMI, 10% FCS/Gln was immediately added. After 18 hours 1ng/ml IL 5 was added (time=0') and at the 24 hour timepoint RNA was isolated. RT-PCR was as in FIG. 8 with α-tubulin amplification as a control for RNA levels (α-tubulin levels were equivalent).

Figure 12:
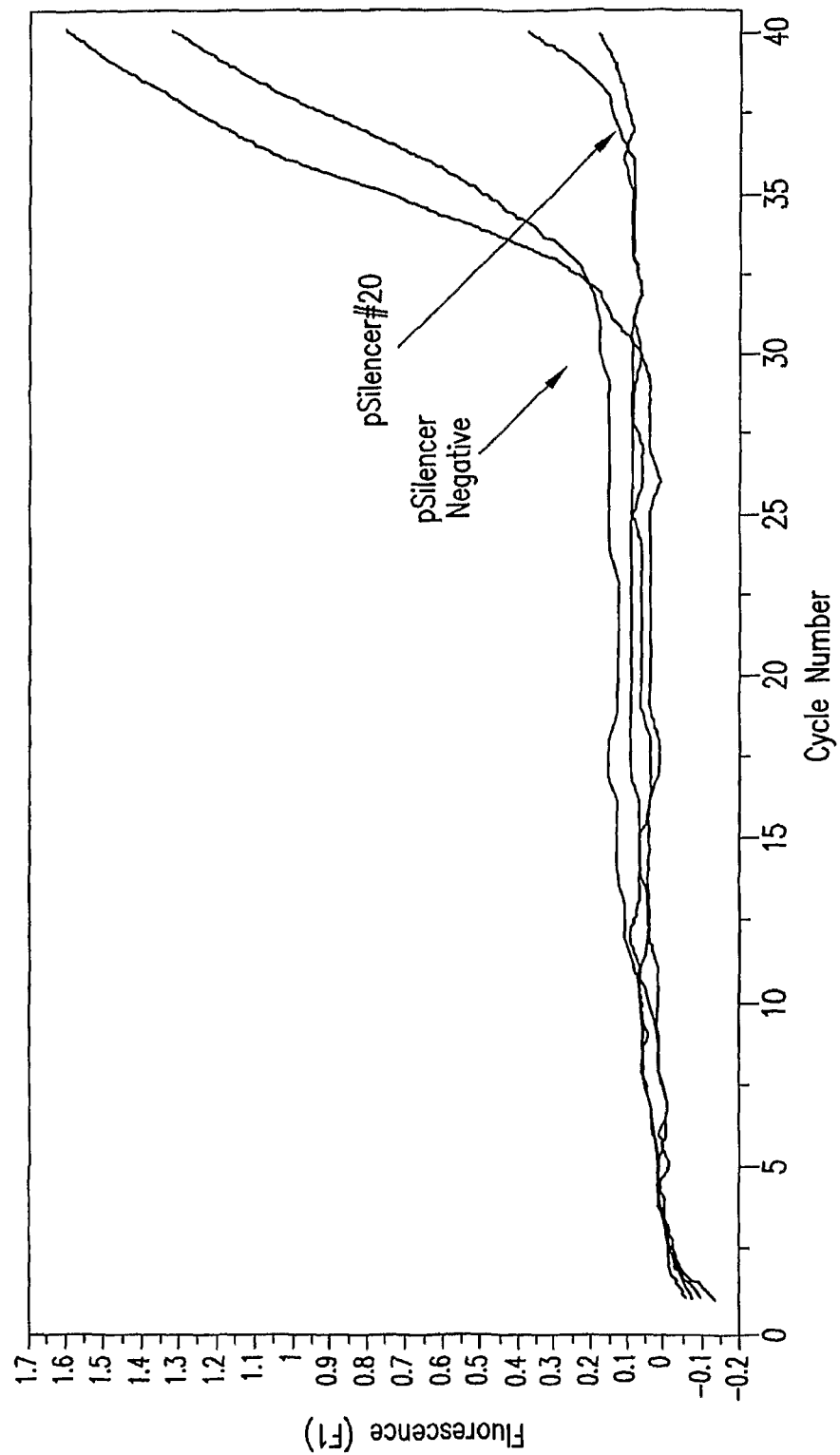
Figure 13A:
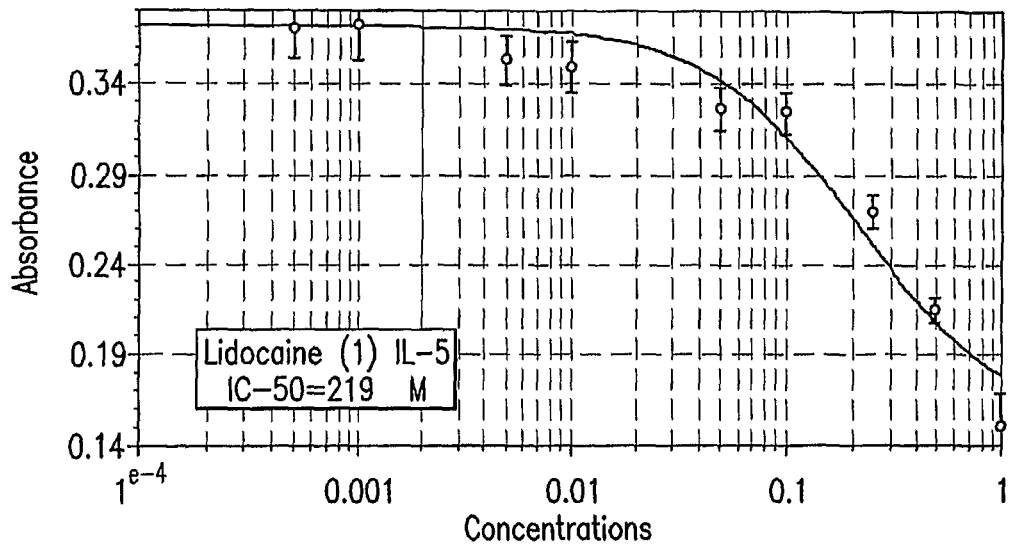
Figure 13B:
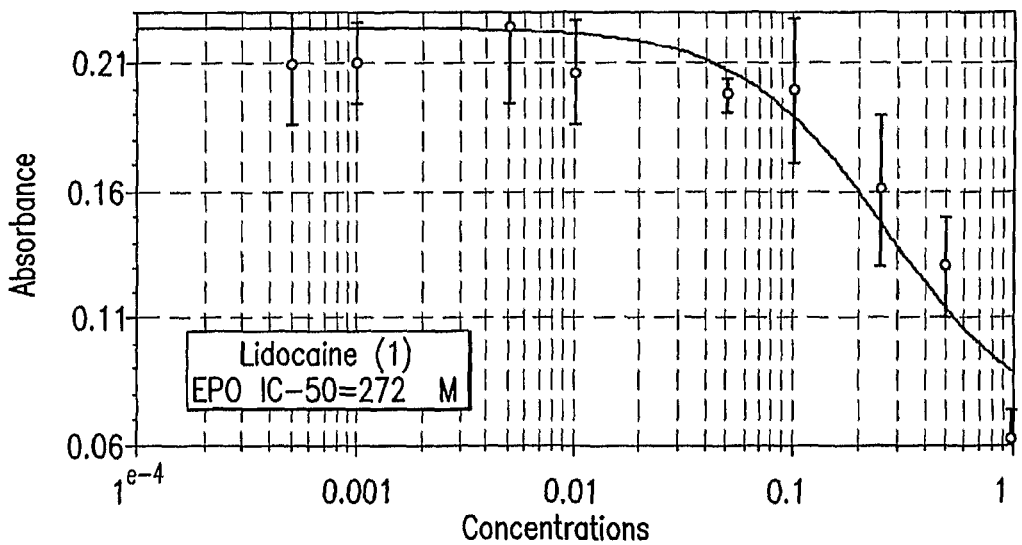
Figure 13C:
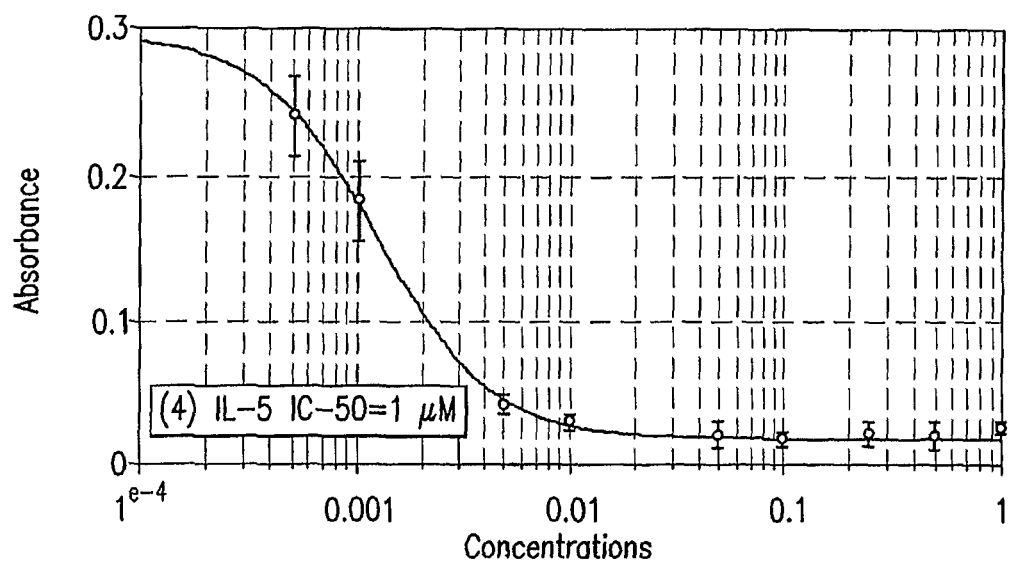
Figure 13D:
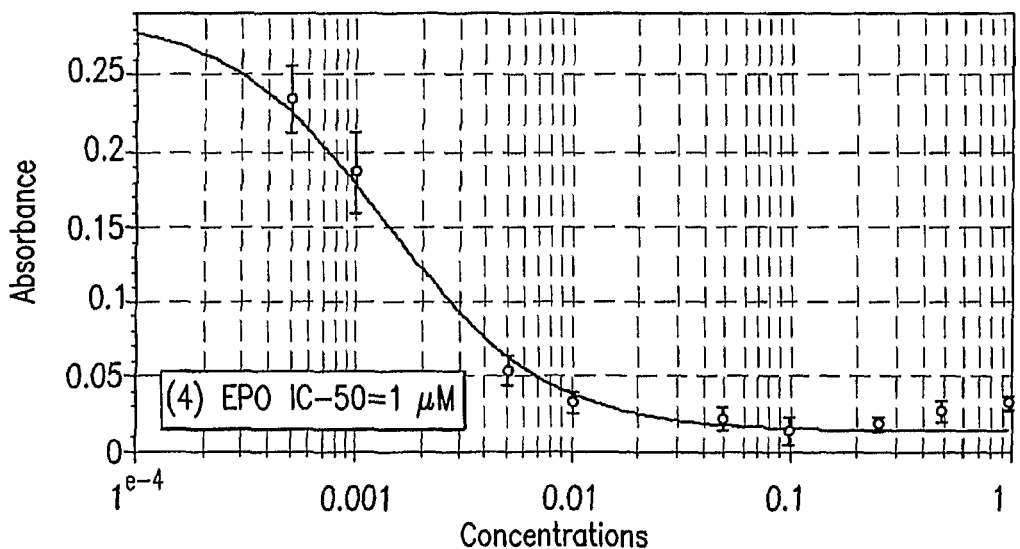

FIG. 12 shows A. FOE (EGO) mRNA silencing. B. MBP mRNA inhibition due to FOE (EGO) silencing. Methods are as in FIG. 8. α-tubulin levels are equivalent in samples shown.

FIG. 13 shows TF-1 cell proliferation assay graphs of Lidocaine (1), 4-Amino-N-pyridin-3-yl-methyl-benzamide (4), and N-(2,6-dimethylphenyl)hexanamide (9). A) Lidocaine in IL-5 stimulated cultures B) Lidocaine in EPO stimulated cultures C) 4-Amino-N-pyridin-3-yl-methyl-benzamide in IL-5 stimulated cultures. D) 4-Amino-N-pyridin-3-yl-methyl-benzamide in EPO stimulated cultures. E) N-(2,6-dimethylphenyl)hexanamide in IL-5 stimulated cultures. F) N-(2,6-dimethylphenyl)hexanamide in EPO stimulated cultures. IC-50 values listed are from that experiment rather than averages listed in the tables.

FIG. 14 shows conservation and gene structure of EGO. Vista tracks of mouse and chicken on the UCSC browser show conservation of the ITPR-1 region. The arrow indicates the EGO region. ITPR-1 exons are shown as vertical lines. The y axis ranges from 50-100% percent identity.

FIG. 15 shows real time Q-RT-PCR of transcript expression following cytokine stimulation of CD34+ cells. A. EGO-A, UCB CD34+ cells B. EGO-B, UCB CD34+ cells C. MBP transcripts following IL-5 or epoietin-α stimulation of UCB CD34+ cells. D. EGO-A and B transcripts following IL-5 stimulation of bone marrow CD34+ cells. EGO-A, solid line. EGO-B, dashed line. Standard errors of PCR triplicates are shown.

FIG. 16 shows expression of EGO in peripheral blood eosinophils. A. Real time Q-RT-PCR of unstimulated peripheral blood eosinophils. B. Real time Q-RT-PCR of IL-5 stimulated peripheral blood eosinophils for EGO-A, solid line and EGO-B, dashed line. Standard errors of PCR triplicates are shown.

Figure 17A:
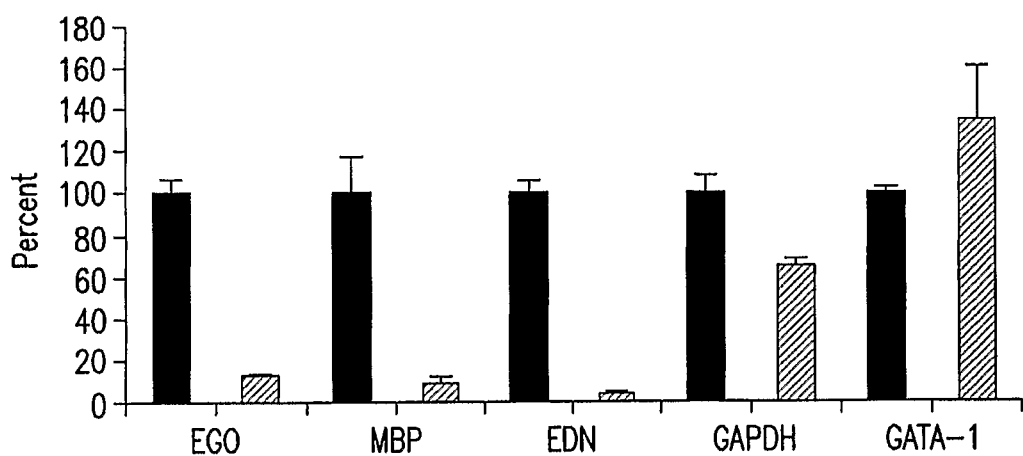
Figure 17B:
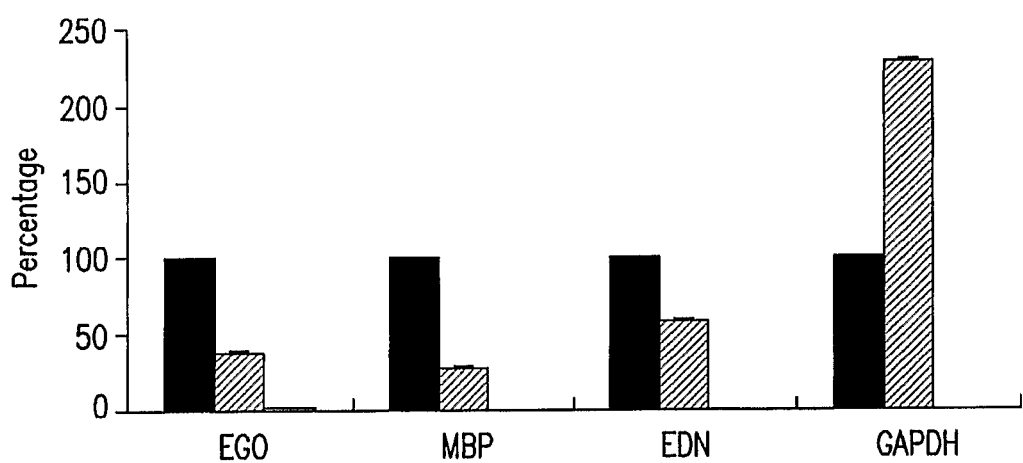

FIG. 17 shows EGO RNA silencing decreases EDN and MBP transcript levels. A. TF-1 cells transfected with negative control plasmid, pSi1 Neg (black) or shRNA targeting both EGO transcripts, pSi1 20-2 (grey). Results shown are from Experiment 5 in Table 8. B. UCB CD34+ cells transfected with negative control plasrnid, pSi1 Neg (black) or shRNA targeting both EGO transcripts, pSi1 20-2 (grey). Standard errors of PCR triplicates are shown.

VI. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. DEFINITIONS

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

"Primers" are a subset of probes which are capable of supporting some type of enzymatic manipulation and which can hybridize with a target nucleic acid such that the enzymatic manipulation can occur. A primer can be made from any combination of nucleotides or nucleotide derivatives or analogs available in the art which do not interfere with the enzymatic manipulation.

"Probes" are molecules capable of interacting with a target nucleic acid, typically in a sequence specific manner, for example through hybridization. The hybridization of nucleic acids is well understood in the art and discussed herein. Typically a probe can be made from any combination of nucleotides or nucleotide derivatives or analogs available in the art.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. GENERAL DESCRIPTION

Eosinophils are tissue dwelling immune cells that are involved in parasitic immunity, especially to helminths. The hallmark of the eosinophil is the presence of toxic, cationic granule proteins that are used to fight parasites but are also detrimental to tissues in the body if inappropriately expressed. The major granule proteins, in order of abundance, are major basic protein (MBP), eosinophil peroxidase (EPO), eosinophil derived neurotoxin (EDN), and eosinophil cationic protein (ECP). These proteins have cytotoxic effects due to their basicity (MBP, EDN, ECP), free radical production (EPO) and ribonuclease activity (EDN, ECP). The toxic effects of these proteins are apparent only when the eosinophil releases its contents by degranulation. Eosinophils develop in the bone marrow in response to interleukins, IL-3, IL-5 and GM-CSF.

Eosinophils are associated with many allergic diseases including asthma, atopic dermatitis, drug reactions and chronic urticaria. Eosinophil-associated gastrointestinal diseases include eosinophilic esophagitis, cosinophilic gastroenteritis and collagenous colitis. Malignant diseases of the eosinophil include hypereosinophilic syndrome. The eosinophil is also involved in diseases caused by adulterated food products such as eosinophilia myalgia syndrome and toxic oil syndrome. Glucocortocoids have been used as a treatment for many of these diseases; however, long term steroid usage causes significant side effects. The myriad of cosinophil related diseases has led us to research the development of the cosinophil from hematopoictic stem cells in an attempt to understand the signals prompting eosinophil production in the bone marrow.

Asthma is a chronic inflammatory condition characterized by eosinophilic, mast cell and T lymphocytic infiltrates in the bronchial mucosa. Inflammation is caused by an increase in Th2 lymphocytes and the production of Th2 cytokines, such as interleukin-4, and -13 which contribute to IgE production and IL-5, which leads to eosinophilia (Nerlov, C., McNagny, K. M., Doderlein, G., Kowenz-Leutz, E. & Graf, T. Distinct C/EBP functions are required for eosinophil lineage commitment and maturation. Genes Dev 12, 2413-23 (1998)). Eosinophil numbers are correlated with disease severity in asthma (Hirasawa, R. et al. Essential and instructive roles of GATA factors in eosinophil development. J Exp Med 195, 1379-86 (2002)). Activated eosinophils secrete toxic granular basic proteins such as major basic protein (BP) which lead to bronchial hyperreactivity, damage of the bronchial mucosa and remodeling of the airways (W. V. Filley, K. E. Holley, G. M. Kephart, G. J. Gleich, Lancet 2, 11 (Jul. 3, 1982)). The eosinophil can cause significant damage to the asthmatic lung.

IL-5 is involved in the eosinophilic response to allergens and parasites. IL-5 deficient mice lack blood and tissue eosinophila when infected with helminths but maintain low baseline levels of apparently normal eosinophils (M. Kopf et al., Immunity 4, 15 (January, 1996)). IL-5 (−/−) mice challenged with aeroallergen lack lung damage, eosinophilia and airway hyperreactivity (P. S. Foster, S. P. Hogan, A. J. Ramsay, K. I. Matthaei, I. G. Young, J Exp Med 183, 195 (Jan. 1, 1996)).

In allergic human asthmatics, inhaled IL-5 causes increased airways sensitivity and blood and sputum eosinophilia (H. Z. Shi et al., Am J Respir Crit Care Med 157, 204 (January, 1998)). Administration of systemic IL-5 also causes increased circulating eosinophil progenitors in patients with mild asthma (H. Z. Shi, C. Q. Li, S. M. Qin, Z. F. Xie, Y. Liu, Clin. Immunol. 91,163 (1999)). Bone marrow CD34+ cells exhibit increased numbers of IL-5R+ cells and increased IL-5 mRNA expression following antigen challenge in mild asthmatics (R. Sehmi et al., J Clin Invest 100, 2466 (Nov. 15, 1997); J. W. Upham, L. M. Hayes, J. Lundahl, R. Sehmi, J. A. Denburg, J Allergy Clin Inmunol 104, 370 (August, 1999)). Therefore, IL-5 is not absolutely required to produce eosinophils but is involved in asthmatic responses and parasite defense.

Asthma is treated with an array of bronchodilating drugs as well as inhaled corticosteroids. However, an attempt is being made to develop new drugs for patients with refractory symptoms. The contribution of IL-5 to eosinophil differentiation, maturation and survival has led to the development of anti-IL-5 therapies in an effort to control asthma. In mice, anti-IL-5 administration inhibited pulmonary eosinophilia, airway hyperresponsiveness and allergic bronchoconstriction. In allergic rabbit and monkey models anti-IL-S also blocked pulmonary eosinophilia (R. W. Egan et al., Arzneimittelforschung 49, 779 (September, 1999); P. J. Mauser et al., Am J Respir Crit Care Med 152, 467 (August, 1995)). Anti-IL-5 therapy has been partially successful in humans; blood, sputum and bone marrow eosinophils are depleted, however, airway tissue eosinophils are only partially depleted and major basic protein (MBP) is not depleted from tissue (T. K. Hart et al., J Allergy Clin Immunol 108, 250 (August, 2001)). Furthermore, allergen-induced bronchoconstriction and airway hyperresponsiveness are uninhibited in humans. Levels of bone marrow eosinophils are not affected by anti IL-5 therapy in animal models and are reduced to 52% in human models (P. T. Flood-Page, A. N. Menzies-Gow, A. B. Kay, D. S. Robinson, Am J Respir Crit Care Med 167, 199 (Jan. 15, 2003)). Alternative targets for asthma drugs, such as genes involved in eosinophilopoiesis, could produce a more effective response and clarify the role of the eosinophil in asthma.

Atopic Dermatitis. Atopic Dermatitis is a chronic, pruritic, eczematous skin disease that has been increasing in prevalence over the past several decades. AD occurs with respiratory allergies approximately 50% of the time and food and aeroallergens provoke lesions in some cases. Skin lesions show dermal infiltrates of IgE receptor bearing Langerhans cells and macrophages as well as CD4+ Th2 T lymphocytes and eosinophils (K. M. Leifennan, J Allergy Clin Immunol 94, 1310 (December, 1994); O. Kaminuma, A. Mori, Int Arch Allergy Immunol 128 Suppl 1, 21 (2002)). Eosinophils are not prominent, however deposition of toxic eosinophil granular proteins such as MBP, EDN and ECP are seen in the majority of patients, showing extensive eosinophil degranulation. Serum IgE, MBP, EDN and ECP are also elevated in atopic dermatitis patients and the level of MBP correlates with % body involvement in the disease (N. L. Ott et al., J Allergy Clin Immunol 94, 120 (July, 1994)). Atopic dermatitis has been correlated with cutaneous lyrmphocyte positive skin homing Th2 T cells. CD4+ cells (R. Lever, M. Turbitt, A. Sanderson, R. MacKie, J Invest Dermatol 89, 4 (July, 1987); M. Akdis, C. A. Akdis, L. Weigl, R. Disch, K. Blaser, J Immunol 159, 4611 (Nov. 1, 1997); M. Akdis et al., J Immunol 163, 466 (Jul. 1, 1999)). The cutaneous late phase reaction in atopic dermatitis patients allergic to dust mite antigen has been correlated with IL-5 production by allergen stimulated peripheral blood mononuclear cells (M. Okada et al., J Dermatol Sci 29, 73 (August, 2002)). IL-5 production can trigger eosinophil migration into the dermis. In summary, eosinophil degranulation is present in most atopic dermatitis lesions and can be a major factor in contributing to the disease.

Eosinophilic Esophagitis. Eosinophilic esophagitis (EE) is a rapidly increasing disease characterized by inflammation-induced dysphasia and a predominant eosinophilic infiltrate in the esophagus. In contrast to gastro esophageal reflux, patients are unresponsive to anti reflux medication (A. Moon, R. E. Kleinman, Ann Allergy Asthma Immunol 74, 5 (January, 1995)). EE patients often have food allergies and elimination of causative foods in the diet can lead to symptom resolution (J. M. Spergel, J. L. Beausoleil, M. Mascarenhas, C. A. Liacouras, J Allergy Clin Immunol 109, 363 (February, 2002); J. Kokkonen, T. Ruuska, T. J. Karttunen, A. Niinimaki, Acta Paediatr 90, 16 (January, 2001)). Furthermore, aeroallergens provoke eosinophilia in the esophagus and lung in a mouse model (A. Mishra, S. P. Hogan, E. B. Brandt, M. E. Rothenberg, J Clin Invest 107, 83 (January, 2001)). The Th2 cytokine, IL-5, induces eosinophil trafficking to the esophagus in transgenic mice and IL-5 deficient mice are resistant to EE. Increased amounts of IL-5 are also present in human EE patients (A. Straumann, M. Bauer, B. Fischer, K. Blaser, H. U. Simon, J Allergy Clin Immunol 108, 954 (December, 2001)). EE is an allergic disease caused by IL-5 dependent eosinophil infiltration.

Introduction to development. Eosinophils develop from CD34+ bematopoietic stem cells in the bone marrow. Eosinophils develop from myeloid progenitors and are regulated primarily by the cytokines, interleukin-3, IL-5 and GM-CSF. Myeloblasts which are largely nucleus, differentiate into promyelocytes, myelocytes, metamyelocytes and finally into mature eosinophils. During this process the nucleus shrinks, becomes bi-lobed and granules appear in the cytoplasm. Interleukin-5 (IL-5) is critical to differentiation, and GATA and C/EBP family transcription factors play central roles in development.

The role of IL-5 eosinophilopoiesis. Interleukin-5 plays a central but probably, redundant role in eosinophilopoiesis. Transgenic mice overproducing IL-5 have persistent eosinophilia (L. A. Dent, M. Strath, A. L. Mellor, C. J. Sanderson, J Exp Med 172, 1425 (Nov. 1, 1990)). However, IL-5 (−/−) mice have low levels of eosinophils showing alternative pathways of eosinophil production. In vitro, eosinophilic differentiation and proliferation are driven selectively by the cytokine, IL-5. Cord blood mononuclear cells grown in IL-5 consist of 78% immature eosinophils by day 14 of culture and 92% eosinophils after 3 weeks of culture. Bone marrow cells incubated with IL-5 also develop into eosinophils. IL-3 and GM-CSF also support eosinophil development but these cytokines are not specific (H. Saito et al., Proc Natl Acad Sci USA 85, 2288 (April, 1988); E. J. Clutterbuck, E. M. Hirst, C. J. Sanderson, Blood 73, 1504 (May 1, 1989)). Lineage specificity of IL-5 is thought to be due to limited expression of the IL-5R because transgenic mice expressing IL5Ra constitutively in all hematopoeitic cells form multi-lineage colonies in response to IL-5 (M. Takagi, T. Hara, M. Ichihara, K. Takatsu, A. Miyajima, J Exp Med 181, 889 (Mar. 1, 1995)).

Transcription factors in eosinophil development. The transition from stem cell to eosinophil is orchestrated by the transcriptional control of developmental and structural genes. In particular, GATA-1, C/EBPα, and C/EBPε play an important role in the regulation of eosinophil development.

GATA transcription factors play a role in lineage commitment as well as in expression of granule proteins. GATA-1 and 2 are expressed in eosinophil and mast cells during myeloid differentiation. Forced expression of GATA-1 or 2 in CD34+ cells in the presence of SCF and GM-CSF gives rise exclusively to eosinophil colonies. This is in contrast to controls which develop predominantly into granulocyte/macrophage colonies (R. Hirasawa et al., J Exp Med 195, 1379 (Jun. 3, 2002)). Similarly, intermediate levels of GATA-1, expressed in chicken myelomonocytic cells, reprogram cells into eosinophils (H. Kulessa, J. Frampton, T. Graf, Genes Dev 9, 1250 (May 15, 1995)). The GATA-1 promoter contains several start sites and enhancing elements including a high affinity GATA-1 binding site within a palindrome in its promoter. GATA-1 null mice die at embryonic day 10-11 of severe anemia. However a knockout of the high affinity GATA-1 binding site in mice selectively abolishes the eosinophil lineage (C. Yu et al., J Exp Med 195, 1387 (Jun. 3, 2002)). This mouse knockout selectively targets eosinophils and shows that the level of GATA-1 expression is critical for lineage-specific development. GATA-1 is also involved in granule protein expression. GATA-1 regulates MBP expression synergistically with PU. 1, an ets family transcription factor. (GATA-1 also interacts with FOG (Friend of GATA) which is an inhibitor of eosinophil differentiation). GATA-1 is an important transcription factor involved in early lineage commitment in a variety of cell types. The level of its expression can be the key to eosinophil specific commitment.

The C/EBP family of transcription factors are CCAAT enhancer binding proteins that have specific effects on eosinophil development. C/EBPα is present in myeloid cell lines, CD34+ CD33+ (a marker of myeloid progenitor commitment) cells and mature granulocytes; CD34+ CD33− cells and lymphocytes do not express C/EBPα (H. S. Radomska et al., Mol Cell Biol 18, 4301 (July, 1998)). C/EBPα is expressed highly in myeloblasts and then decreases (L. M. Scott, C. I. Civin, P. Rorth, A. D. Friedman, Blood 80, 1725 (Oct 1, 1992)). Also, C/EBPα (−/−) mice die at birth and show a selective loss of mature neutrophils and eosinophils in the blood or fetal liver due to a defect in G-CSF signaling (D. E. Zhang et al., Proc Natl Acad Sci USA 94, 569 (Jan. 21, 1997)). C/EBPε is a later acting transcription factor that is preferentially expressed during granulocytic differentiation. Mice null for C/EBPε survive for 2-5 months in pathogen free conditions. The mouse knockout of C/EBPε has specific effect on granulocytes; only neutrophils and eosinophils are affected. Mice knockouts show arrest in development at the myelocyte to metamyelocyte stage but have mature dysfunctional neutrophils and eosinophils in the peripheral blood (R. Yamanaka et al., Proc Natl Acad Sci USA 94, 13187 (Nov. 25, 1997)). The CCAAT binding proteins have both early and late effects on eosinophil development.

EGO (Eosinophil Granule Ontogeny, also referred to herein as FOE, or Friend of Eosinophils) is a novel nested, non-coding, RNA (ncRNA) gene involved in eosinophil development. ncRNA accounts for at least half of transcribed genes in mammals and has been increasingly implicated in playing a functional role in biology (Claverie, J. M. Fewer genes, more noncoding RNA. Science 309, 1529-30 (2005); Carninci, P. et al. The transcriptional landscape of the mammalian genome. Science 309, 1559-63 (2005); Ravasi, T. et al. Experimental validation of the regulated expression of large numbers of non-coding RNAs from the mouse genome. Genome Res 16, 11-9 (2006); Willingham, A. T. et al. A strategy for probing the function of noncoding RNAs finds a repressor of NFAT. Science 309, 1570-3 (2005)). ncRNAs are often found nested in the introns or in 3' untranslated regions of coding genes. EGO is an ncRNA involved in regulating eosinophil development.

Genes expressed in early eosinophil development were investigated by transcriptional profiling of CD34+ cells stimulated with IL-5. An increase in inflammatory cytokine, cytokine receptor and chemokine ligand transcript expression was shown by microarray. Included in the differentially expressed proinflammatory molecules are: IL-6, IL1F9, CCL19, CCL1, CCL6, COX-2, IL12B, IL21R, EBI3, IL1RL1 and IL1RB. IL12B promoter polymoiphism has been reported to be linked with asthma severity and atopic dermatitis (Morahan et al. 2002, Tsunemi et al. 2002) and IL21R is associated with rheumatoid arthritis (Jungel et al. 2004). Of particular interest is the increased expression of the HEY1 (hairy enhancer of split) transcription factor. HEY1 is reported to physically interact with GATA-1 to decrease its activity (Elagib et al. 2004). An intermediate level of GATA-1 is instrumental in eosinophil development; therefore, HEY1 can be the effector molecule that maintains these critical levels. Furthermore, the results show that, EGO, a transcript nested within an intron on the opposite strand of ITPR-1, also increases levels in response to IL-5. However, ITPR-1 does not increase mRNA levels following IL-5 stimulation (Table 1). EGO is an ncRNA gene as shown by both the absence of a conserved open reading frame and the lack of association with ribosomes. EGO is highly expressed in the bone marrow and is induced by IL-5. Finally, RNA silencing experiments show that EGO is instrumental in the expression of granule proteins that are critical to eosinophil development.

EGO is nested within an intron of the ITPR-1 gene. Approximately 158 coding nested genes have been identified in the human genome (Yu et al. 2005). However, at least half of transcripts in mammals are non-coding and many ncRNAs are found in introns or in the 3' untranslated regions of coding genes (Carninci et al. 2005, Ravasi et al. 2006). The conservation in the ITPR-1 intron in which EGO is nested is higher than most ITPR-1 exons, with up to 90% identity. However, the highest region of conservation is within the intron of EGO-B, showing an additional transcript or a regulatory region. Q-RT-PCR shows the intron of EGO-B is highly expressed, but not inducible with IL-5 (L. Wagner, Supplementary FIG. 2), suggesting an additional novel gene in this region. Northern blot data also show an additional 2 kb transcript when probed with the intron of EGO-B (Supplementary FIG. 3). EGO-A and the 5' exon of EGO-B have up to 75% identity between human and mouse, reflecting evolutionary pressure and a possible functional role for these transcripts. These data suggest that EGO has been retained by evolutionary pressure and may have a functional role.

The lack of a large open reading frame and poor amino acid conservation of small open reading frames show that EGO is an ncRNA. Furthermore, EGO transcripts are not associated with ribosomes in vitro, although translated mRNA, such as α-tubulin, is present in the polyribosome fraction of the sucrose gradient. This shows that EGO does not code for a protein.

Tissue specific expression and inducible expression of ncRNA shows functionality. Expression of EGO RNA is rapidly and transiently upregulated following IL-5 addition to CD34+ hematopoietic cell culture derived from umbilical cord blood or bone marrow. However, person to person variation of transcriptional regulation of EGO gene expression following IL-5 stimulation is large and can vary from 2-90 folds. EGO RNA is very highly expressed in bone marrow; 6-10 fold higher than kidney, an organ with high expression levels, and several orders of magnitude higher than the lowest expressing organs, such as brain. EGO RNA is also expressed highly in bone marrow mononuclear cells. Bone marrow mononuclear cells that have lost CD34 expression during development may still express EGO at moderate levels. EGO transcript levels were not high in thymus cDNA, suggesting that EGO does not have a role in lymphoid development. The high, tissue specific expression of EGO in bone marrow is indicative of a role in hematopoietic development.

The functional role of EGO was investigated by RNA silencing. TE-1, a CD34+ cell line, which is dependent on cytokine induced proliferation and CD34+ UCB cells were used to evaluate the effect of EGO RNA silencing on eosinophil granule mRNA expression. TF-1 cells express EGO and granule protein mRNA constitutively during growth on a variety of cytokines. Knockdown of EGO transcripts in TF-1 cells affects the level of granule protein mRNA; MBP mRNA levels are approximately 23% of control transfectants and EDN transcript levels are 59% of control levels. Likewise, in CD34+ UCB cells grown on IL-5, knockdown of both EGO transcripts decreases MBP mRNA levels to 23% of control and EDN transcript levels are 31% of control. IL-3 was added in addition to IL-5 in an attempt to cause the cells to complete differentiation after transfection; however, although control cells grew well, EGO silenced cells died at approximately one week. Therefore, EGO is an ncRNA which is developmentally regulated in eosinophil progenitors in the bone marrow and affects granule protein mRNA levels.

C. METHODS

Disclosed herein are methods of inhibiting eosinophil development in a subject comprising reducing EGO mRNA levels in the subject. "Reducing or inhibiting EGO mRNA levels" is defined as actually reducing the number of mRNA molecules in the cell, or functionally reducing the number of independent EGO mRNAs, by for example, modulating the activity of the mRNA. This can mean, for example, causing the mRNA to be complexed with another nucleic acid or other composition that will reduce its availability, changing the conformation of the mRNA, or otherwise limiting the ability of EGO mRNA to function in a cell or a subject or to interact with other molecules. The term "reducing or inhibiting EGO mRNA levels" means reducing the total amount of EGO mRNA, or reducing the amount of functional EGO mRNA available, by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%. The term "reducing or inhibiting eosinophil development" means reducing the number of eosinophils present by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%. In one example, the level of EGO is reduced by RNA silencing. In the RNA interference (RNAi) pathway, dsRNAs get processed into 20-25 nucleotide (nt) small interfering RNAs (siRNAs) by an RNase III-like enzyme called Dicer (initiation step). Then, the siRNAs assemble into endoribonuclease-containing complexes known as RNA-induced silencing complexes (RISCs), unwinding in the process. The siRNA strands subsequently guide the RISCs to complementary RNA molecules, where they cleave and destroy the cognate RNA (effecter step). Cleavage of cognate RNA takes place near the middle of the region bound by the siRNA strand. siRNA design is known to those of skill in the art, and there are multiple sources of information for designing such molecules which have been published and are on the internet, such as the website A further discussion of RNA silencing follows.

Also disclosed herein are methods of reducing eosinophil-related diseases in a subject comprising reducing EGO mRNA levels in the subject. Examples of such diseases are given above. Further examples include, but are not limited to, asthma; skin diseases such as atopic dermatitis, urticaria, drug reactions, reactions to insect stings, or CTCL; Eosinophilia Myalgia Syndrome; eosinophilic esophagitis, Toxic Oil Syndrome, and Hypereosinophilic Syndrome.

D. COMPOSITIONS

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B and C are disclosed as well as a class of molecules D, E and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

1. Modulators of Eosinophils/EGO

Provided herein are compositions that act to modulate an activity of eosinophils. This can be done, for example, by modulating EGO. "Activity," as used herein, refers to any function or process of a composition disclosed herein and includes, for example, transcription, translation, post-translational modification, translocation, homophilic or heterophilic binding, secretion, endocytosis, or degradation. Disclosed therefore are compositions that inhibit one or more activities of eosinophils, or EGO, as provided herein. These compositions are referred to herein as eosinophil or EGO inhibitors. Inhibition or a form of inhibition, such as inhibit or inhibiting, as used herein means to restrain or limit. Reduce or a form of reduce, such as reducing or reduces, as used herein, means to diminish, for example in size or amount. It is understood that wherever one of inhibit or reduce is used, unless explicitly indicated otherwise, the other can also be used. For example, if something is referred to as "inhibited," it is also considered referred to as "reduced."

2. Sequence Similarities

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Saeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

3. Nucleic Acids

There are a variety of molecules disclosed herein that are nucleic acid based, including for example the nucleic acids that encode, for example, EGO as well as any other proteins disclosed herein, as well as various functional nucleic acids. The disclosed nucleic acids are made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G and U. Likewise, it is understood that if, for example, an antisense molecule is introduced into a cell or cell environment through for example exogenous delivery, it is advantagous that the antisense molecule be made up of nucleotide analogs that reduce the degradation of the antisense molecule in the cellular environment.

a) Nucleotides and Related Molecules

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U) and thymin-1-yl (T). The sugar moiety of a nucleotide is a ribose or a deoxyribose. The phosphate moiety of a nucleotide is pentavalent phosphate. An non-limiting example of a nucleotide would be 3'-AMP (3'-adenosine monophosphate) or 5'-GMP (5'-guanosine monophosphate).

A nucleotide analog is a nucleotide which contains some type of modification to the base, sugar or phosphate moieties. Modifications to nucleotides are well known in the art and would include for example, 5-methylcytosine (5-me-C), 5-hydroxymethyl cytosine, xanthine, hypoxanthine and 2-aminoadenine as well as modifications at the sugar or phosphate moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety. (Letsinger et al., Proc. Natl. Acad. Sci. USA, 1989,86, 6553-6556), A Watson-Crick interaction is at least one interaction with the Watson-Crick face of a nucleotide, nucleotide analog or nucleotide substitute. The Watson-Crick face of a nucleotide, nucleotide analog or nucleotide substitute includes the C2, N1 and C6 positions of a purine based nucleotide, nucleotide analog or nucleotide substitute and the C2, N3, C4 positions of a pyrimidine based nucleotide, nucleotide analog or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

b) Sequences

There are a variety of sequences related to, for example, EGO, as well as any other protein disclosed herein that are disclosed on Genbank, and these sequences and others are herein incorporated by reference in their entireties as well as for individual subsequences contained therein.

A variety of sequences are provided herein and these and others can be found in Genbank. Those of skill in the art understand how to resolve sequence discrepancies and differences and to adjust the compositions and methods relating to a particular sequence to other related sequences. Primers and/or probes can be designed for any sequence given the information disclosed herein and known in the art.

c) Functional Nucleic Acids

Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, and external guide sequences, as disclosed herein. The functional nucleic acid molecules can act as affectors, inhibitors, modulators and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the RNA of EGO. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($k_d$) less than or equal to $10^{-6}$, $10^{-8}$, $10^{-10}$ or $10^{-12}$. A representative sample of methods and techniques which aid in the design and use of antisense molecules can be found in the following non-limiting list of U.S. Pat. Nos. 5,135,917, 5,294,533, 5,627,158, 5,641,754, 5,691,317, 5,780,607, 5,786,138, 5,849,903, 5,856,103, 5,919,772, 5,955,590, 5,990,088, 5,994,320, 5,998,602, 6,005,095, 6,007,995, 6,013,522, 6,017,898, 6,018,042, 6,025,198, 6,033,910, 6,040,296, 6,046,004, 6,046,319 and 6,057,437.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP (U.S. Pat. No. 5,631,146) and theophiline (U.S. Pat. No. 5,580,737), as well as large molecules, such as reverse transcriptase (U.S Pat. No. 5,786,462) and thrombin (U.S. Pat. No. 5,543,293). Aptamers can bind very tightly with $k_d$s from the target molecule of less than $10^{-12}$ M. It is preferred that the aptamers bind the target molecule with a $k_d$ less than $10^{-6}$, $10^{-8}$, $10^{-10}$ or $10^{-12}$. Aptamers can bind the target molecule with a very high degree of specificity. For example, aptamers have been isolated that have greater than a 10000 fold difference in binding affinities between the target molecule and another molecule that differ at only a single position on the molecule (U.S. Pat. No. 5,543,293). It is preferred that the aptamer have a $k_d$ with the target molecule at least 10, 100, 1000, 10,000 or 100,000 fold lower than the $k_d$ with a background binding molecule. Representative examples of how to make and use aptamers to bind a variety of different target molecules can be found in the following non-limiting list of U.S. Pat. Nos. 5,476,766, 5,503,978, 5,631,146, 5,731,424, 5,780,228, 5,792,613, 5,795,721, 5,846,713, 5,858,660, 5,861,254, 5,864,026, 5,869,641, 5,958,691, 6,001,988, 6,011,020, 6,013,443, 6,020,130, 6,028,186, 6,030,776 and 6,051,698.

Gene expression can also be effectively silenced in a highly specific manner through RNA interference (RNAi). This silencing was originally observed with the addition of double stranded RNA (dsRNA) (Fire, A., et al. (1998) *Nature*, 391, 806 811) (Napoli, C., et al. (1990) *Plant Cell* 2, 279 289) (Hannon, G. J. (2002) *Nature*, 418, 244 251). Once dsRNA enters a cell, it is cleaved by an RNase III-like enzyme, Dicer, into double stranded small interfering RNAs (siRNA) 21-23 nucleotides in length that contains 2 nucleotide overhangs on the 3' ends (Elbashir, S. M., et al. (2001) *Genes Dev.*, 15:188-200) (Bernstein, E., et al. (2001) *Nature*, 409, 363 366) (Hammond, S. M., et al. (2000) *Nature*, 404:293-296). In an ATP dependent step, the siRNAs become integrated into a multi-subunit protein complex, commonly known as the RNAi induced silencing complex (RISC), which guides the siRNAs to the target RNA sequence (Nykanen, A., et al. (2001) *Cell*, 107:309 321). At some point the siRNA duplex unwinds, and it appears that the antisense strand remains bound to RISC and directs degradation of the complementary mRNA sequence by a combination of endo and exonucleases (Martinez, J., et al. (2002) *Cell*, 110:563-574). However, the effect of iRNA or siRNA or their use is not limited to any type of mechanism.

Short Interfering RNA (siRNA) is a double-stranded RNA that can induce sequence-specific post-transcriptional gene silencing, thereby decreasing or even inhibiting gene expression. In one example, an siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends, herein incorporated by reference for the method of making these siRNAs. Sequence specific gene silencing can be achieved in mammalian cells using synthetic, short double-stranded RNAs that mimic the siRNAs produced by the enzyme dicer (Elbashir, S. M., et al. (2001) *Nature*, 411:494 498) (Ui-Tei, K., et al. (2000) *FEBS Lett* 479:79-82). siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's *SILENCER* siRNA Construction Kit.

The production of siRNA from a vector is more commonly done through the transcription of a shRNA. Kits for the production of vectors comprising shRNA are available, such as for example Imgenex's GeneSuppressor Construction Kits and Invitrogen's BLOCK-iT inducible RNAi plasmid and lentivirus vectors.

Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes, (for example, but not limited to the following U.S. Pat. Nos. 5,334,711, 5,436,330, 5,616,466, 5,633,133, 5,646,020, 5,652,094, 5,712,384, 5,770,715, 5,856,463, 5,861,288, 5,891,683, 5,891,684, 5,985,621, 5,989,908, 5,998,193, 5,998,203, WO 9858058 by Ludwig and Sproat, WO 9858057 by Ludwig and Sproat and WO 9718312 by Ludwig and Sproat) hairpin ribozymes (for example, but not limited to the following U.S. Pat. Nos. 5,631,115, 5,646,031, 5,683,902, 5,712,384, 5,856,188, 5,866,701, 5,869,339 and 6,022,962) and tetrahymena ribozymes (for example, but not limited to the following U.S. Pat. Nos. 5,595,873 and 5,652,107). There are also a number of ribozymes that are not found in natural systems, but which have been engineered to catalyze specific reactions de novo (for example, but not limited to the following U.S. Pat. Nos. 5,580,967, 5,688,670, 5,807,718 and 5,910,408). Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Representative examples of how to make and use ribozymes to catalyze a variety of different reactions can be found in the following non-limiting list of U.S. Pat. Nos. 5,646,042, 5,693,535, 5,731,295, 5,811,300, 5,837,855, 5,869,253, 5,877,021, 5,877,022, 5,972,699, 5,972,704, 5,989,906 and 6,017,756.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependant on both Watson-Crick and Hoogsteen base-pairing. Triplex molecules are preferred because they can bind target regions with high affinity and specificity. It is preferred that the triplex forming molecules bind the target molecule with a $k_d$ less than $10^{-6}$, $10^{-8}$, $10^{-10}$ or $10^{-12}$. Representative examples of how to make and use triplex forming molecules to bind a variety of different target molecules can be found in the following non-limiting list of U.S. Pat. Nos. 5,176,996, 5,645,985, 5,650,316, 5,683,874, 5,693,773, 5,834,185, 5,869,246, 5,874,566 and 5,962,426.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. (WO 92/03566 by Yale, and Forster and Altman, *Science* 238:407-409 (1990)).

Similarly, eukaryotic EGS/RNAse P-directed cleavage of RNA can be utilized to cleave desired targets within eukarotic cells. (Yuan et al., *Proc. Natl. Acad. Sci.* USA 89:8006-8010 (1992); WO 93/22434 by Yale; WO 95/24489 by Yale; Yuan and Altman, *EMBO J* 14:159-168 (1995), and Carrara et al., *Proc. Natl. Acad. Sci.* (USA) 92:2627-2631 (1995)). Representative examples of how to make and use EGS molecules to facilitate cleavage of a variety of different target molecules be found in the following non-limiting list of U.S. Pat. Nos. 5,168,053, 5,624,824, 5,683,873, 5,728,521, 5,869,248 and 5,877,162.

4. Nucleic Acid Delivery

In the methods described above which include the administration and uptake of exogenous DNA into the cells of a subject (i.e., gene transduction or transfection), the disclosed nucleic acids can be in the form of naked DNA or RNA, or the nucleic acids can be in a vector for delivering the nucleic acids to the cells, whereby the antibody-encoding DNA fragment is under the transcriptional regulation of a promoter, as would be well understood by one of ordinary skill in the art. The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available .liposome preparations such as LIPOFECTIN, LIPOFECTAMiNE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

As one example, vector delivery can be via a viral system, such as a retroviral vector system which can package a recombinant retroviral genome (see e.g., Pastan et al., *Proc. Natl. Acad. Sci. U.S.A.* 85:4486, 1988; Miller et al., *Mol. Cell. Biol.* 6:2895, 1986). The recombinant retrovirus can then be used to infect and thereby deliver to the infected cells nucleic acid encoding a broadly neutralizing antibody (or active fragment thereof). The exact method of introducing the altered nucleic acid into mammalian cells is, of course, not limited to the use of retroviral vectors. Other techniques are widely available for this procedure including the use of adenoviral vectors (Mitani et al., *Hum. Gene Ther.* 5:941-948, 1994), adeno-associated viral (AAV) vectors (Goodman et al., *Blood* 84:1492-1500, 1994), lentiviral vectors (Naidini et al., *Science* 272:263-267, 1996), pseudotyped retroviral vectors (Agrawal et al., *Exper. Hematol.* 24:738-747, 1996). Physical transduction techniques can also be used, such as liposome delivery and receptor-mediated and other endocytosis mechanisms (see, for example, Schwartzenberger et al., *Blood* 87:472-478, 1996). This disclosed compositions and methods can be used in conjunction with any of these or other commonly used gene transfer methods.

As one example, if the antibody-encoding nucleic acid is delivered to the cells of a subject in an adenovirus vector, the dosage for administration of adenovirus to humans can range from about $10^7$ to $10^9$ plaque forming units (pfu) per injection but can be as high as $10^{12}$ pfu per injection (Crystal, *Hum. Gene Ther.* 8:985-1001, 1997; Alvarez and Curiel, *Hum. Gene Ther.* 8:597-613, 1997). A subject can receive a single injection, or, if additional injections are necessary, they can be repeated at six month intervals (or other appropriate time intervals, as determined by the skilled practitioner) for an indefinite period and/or until the efficacy of the treatment has been established.

Parenteral administration of the nucleic acid or vector, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. For additional discussion of suitable formulations and various routes of administration of therapeutic compounds, see, e.g., *Remington: The Science and Practice of Pharmacy* (19th ed.) ed. A. R. Gennaro, Mack Publishing Company, Easton, Pa. 1995.

5. Delivery of the Compositions to Cells

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991) Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

a) Nucleic Acid Based Delivery Systems

Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)).

As used herein, plasmid or viral vectors are agents that transport the disclosed nucleic acids into the cell without degradation and include a promoter yielding expression of the gene in the cells into which it is delivered. In some embodiments the vectors are derived from either a virus or a retrovirus. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transaction (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

(1) Retroviral Vectors

A retrovirus is an animal virus belonging to the virus family of Retroviridae, including any types, subfamilies, genus, or tropisms. Retroviral vectors, in general, are described by Verma, L M., Retroviral vectors for gene transfer. In Microbiology-1985, American Society for Microbiology, pp. 229-232, Washington, (1985), which is incorporated by reference herein. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol and env genes which are involved in the making of the protein coat. It is the gag, pol and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

(2) Adenoviral Vectors

The construction of replication-defective adenoviruses has been described (Berkner et al., J. Virology 61:1213-1220 (1987); Massie et al., Mol. Cell. Biol. 6:2872-2883 (1986); Haj-Ahmad et al., J. Virology 57:267-274 (1986); Davidson et al., J. Virology 61:1226-1239 (1987); Zhang "Generation and identification of recombinant adenovirus by liposome-mediated transfection and PCR analysis" BioTechniques 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, J. Clin. Invest. 92:1580-1586 (1993); Kirshenbaum, J. Clin. Invest. 92:381-387 (1993); Roessler, J. Clin. Invest. 92:1085-1092 (1993); Moullier, Nature Genetics 4:154-159 (1993); La Salle, Science 259:988-990 (1993); Gomez-Foix, J. Biol. Chem. 267:25129-25134 (1992); Rich, Human Gene Therapy 4:461-476 (1993); Zabner, Nature Genetics 6:75-83 (1994); Guzman, Circulation Research 73:1201-1207 (1993); Bout, Human Gene Therapy 5:3-10 (1994); Zabner, Cell 75:207-216 (1993); Caillaud, Eur. J. Neuroscience 5:1287-1291 (1993); and Ragot, J. Gen. Virology 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, Virology 40:462-477 (1970); Brown and Burlingham, J. Virology 12:386-396 (1973); Svensson and Persson, J. Virology 55:442-449 (1985); Seth, et al., J. Virol. 51:650-655 (1984); Seth, et al., Mol. Cell. Biol. 4:1528-1533 (1984); Varga et al., J. Virology 65:6061-6070 (1991); Wickham et al., Cell 73:309-319 (1993)).

A viral vector can be one based on an adenovirus which has had the E1 gene removed and these virons are generated in a cell line such as the human 293 cell line. In another preferred embodiment both the E1 and E3 genes are removed from the adenovirus genome.

(3) Adeno-asscociated Viral Vectors

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorproated by reference for material related to the AAV vector.

The disclosed vectors thus provide DNA molecules which are capable of integration into a mammalian chromosome without substantial toxicity.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

(4) Large Payload Viral Vectors

Molecular genetic experiments with large human herpesviruses have provided a means whereby large heterologous DNA fragments can be cloned, propagated and established in cells permissive for infection with herpesviruses (Sun et al., Nature genetics 8: 33-41, 1994; Cotter and Robertson,.Curr Opin Mol Ther 5: 633-644, 1999). These large DNA viruses (herpes simplex virus (HSV) and Epstein-Barr virus (EBV), have the potential to deliver fragments of human heterologous DNA>150 kb to specific cells. EBV recombinants can maintain large pieces of DNA in the infected B-cells as episomal DNA. Individual clones carried human genomic inserts up to 330 kb appeared genetically stable. The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA >220 kb and to infect cells that can stably maintain DNA as episomes.

Other useful systems include, for example, replicating and host-restricted non-replicating vaccinia virus vectors.

b) Non-nucleic Acid Based Systems

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed compositions or vectors for example, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. *Am. J Resp. Cell. Mol. Biol.* 1:95-100 (1989); Felgner et al. *Proc. Natl. Acad. Sci USA* 84:7413-7417 (1987); U.S. Pat. No.4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129: 57-80, (1992); and Roffler, et al., *Biochem. Pharmacol*, 42:2062-2065, (1991)). These techniques can be used for a variety of other speciifc cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

Nucleic acids that are delivered to cells which are to be integrated into the host cell genome, typically contain integration sequences. These sequences are often viral related sequences, particularly when viral based systems are used. These viral integration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

c) In vivo/ex vivo

As described above, the compositions can be administered in a pharmaceutically acceptable carrier and can be delivered to the subject=s cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

6. Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

a) Viral Promoters and Enhancers

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., *Nature*, 273: 113 (1978)). The immediate early promoter of the human cytomegalovirus is conveniently obtained as a HindIII E restriction fragment (Greenway, P. J. et al., *Gene* 18: 355-360 (1982)). Of course, promoters from the host cell or related species also are useful herein.

Enhancer generally refers to a sequence of DNA that functions at no fixed distance from the transcription start site and can be either 5' (Laimins, L. et al., *Proc. Natl. Acad. Sci.* 78: 993(1981)) or 3' (Lusky, M. L., et al., *Mol. Cell Bio.* 3: 1108(1983)) to the transcription unit. Furthermore, enhancers can be within an intron (Banerji, J. L. et al., *Cell* 33: 729 (1983)) as well as within the coding sequence itself (Osborne, T. F., et al., *Mol. Cell Bio.* 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, -fetoprotein and insulin), typically one will use an enhancer from a eukaryotic cell virus for general expression.

Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

b) Markers

The viral vectors can include nucleic acid sequence encoding a marker product. This marker product is used to determine if the gene has been delivered to the cell and once delivered is being expressed. Preferred marker genes are the *E. Coli* lacZ gene, which encodes β-galactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR– cells and mouse LTK– cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., *J. Molec. Appl. Genet.* 1: 327 (1982)), mycophenolic acid, (Mulligan, R. C. and Berg, P. *Science* 209: 1422 (1980)) or hygromycin, (Sugden, B. et al., *Mol. Cell. Biol.* 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

7. Antibodies (1) Antibodies Generally

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with EGO such that EGO is inhibited from acting in eosinophil development. The antibodies can be tested for their desired activity using the in vitro assays described herein, or by analogous methods, after which their in vivo therapeutic and/or prophylactic activities are tested according to known clinical testing methods.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., *Proc. Natl. Acad. Sci. USA,* 81:6851-6855 (1984)).

The disclosed monoclonal antibodies can be made using any procedure which produces mono clonal antibodies. For example, disclosed monoclonal antibodies can be prepared using hybridoma methods, such as those described by Kohler and Milstein, *Nature,* 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro, e.g., using the HIV Env-CD4-co-receptor complexes described herein.

The monoclonal antibodies may also be made by recombinant DNA methods, such as those described in U.S. Pat. No.

4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. *Curr. Opin. Biotechnol.* 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

(2) Human Antibodies

The disclosed human antibodies can be prepared using any technique. Examples of techniques for human monoclonal antibody production include those described by Cole et al. (*Monoclonal Antibodies and Cancer Therapy*, Alan R. Liss, p. 77, 1985) and by Boerner et al. (*J. Immunol.*, 147(1):86-95, 1991). Human antibodies (and fragments thereof) can also be produced using phage display libraries (Hoogenboom et al., *J. Mol. Biol.*, 227:381, 1991; Marks et al., *J. Mol. Biol.*, 222:581, 1991).

The disclosed human antibodies can also be obtained from transgenic animals. For example, transgenic, mutant mice that are capable of producing a fill repertoire of human antibodies, in response to immunization, have been described (see, e.g., Jakobovits et al., *Proc. Natl. Acad. Sci. USA*, 90:2551-255 (1993); Jakobovits et al., *Nature*, 362:255-258 (1993); Bruggermann et al., *Year in Immunol.*, 7:33 (1993)). Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge. Antibodies having the desired activity are selected using Env-CD4-co-receptor complexes as described herein.

(3) Humanized Antibodies

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., *Nature*, 321:522-525 (1986), Reichmann et al., *Nature*, 332:323-327 (1988), and Presta, *Curr. Opin. Struct. Biol.*, 2:593-596 (1992)).

Methods for humanizing non-human antibodies are well known in the art. For example, humanized antibodies can be generated according to the methods of Winter and co-workers (Jones et al., *Nature*, 321:522-525 (1986), Riechmann et al., *Nature*, 332:323-327 (1988), Verhoeyen et al., *Science*, 239: 1534-1536 (1988)), by substituting rodent CDRs or CDR sequences for the corresponding sequences of a human antibody. Methods that can be used to produce humanized antibodies are also described in U.S. Pat. No.4,816,567 (Cabilly et al.), U.S. Pat. No.5,565,332 (Hoogenboom et al.), U.S. Pat. No. 5,721,367 (Kay et al.), U.S. Pat. No.5,837,243 (Deo et al.), U.S. Pat. No. 5, 939,598 (Kucherlapati et al.), U.S. Pat. No.6,130,364 (Jakobovits et al.), and U.S. Pat. No. 6,180,377 (Morgan et al.).

(4) Administration of Antibodies

Administration of the antibodies can be done as disclosed herein. Nucleic acid approaches for antibody delivery also exist. The broadly neutralizing anti EGO antibodies and antibody fragments can also be administered to patients or subjects as a nucleic acid preparation (e.g., DNA or RNA) that encodes the antibody or antibody fragment, such that the patient's or subject's own cells take up the nucleic acid and produce and secrete the encoded antibody or antibody fragment. The delivery of the nucleic acid can be by any means, as disclosed herein, for example.

8. Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pieterz and McKenzie, *Immunolog. Reviews*, 129:57-80, (1992); and Roffler, et al., *Biochem. Pharmacol*, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a) Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharnaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid and phosphoric acid, and organic acids such as formic acid, acetic acid, propionic acid, glycolic acid, lactic acid, pyruvic acid, oxalic acid, malonic acid, succinic acid, maleic acid and fumaric acid, or by reaction with an inorganic base such as sodium hydroxide, ammonium hydroxide, and potassium hydroxide, and organic bases such as mono-, di-, trialkyl and aryl amines and substituted ethanolamines.

b) Therapeutic Uses

Effective dosages and schedules for administering the compositions may be determined empirically, and making such determinations is within the skill in the art. The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

Following administration of a disclosed composition, such as an antibody, for treating, inhibiting, or preventing eosinophil development, the efficacy of the therapeutic antibody can be assessed in various ways well known to the skilled practitioner. For instance, one of ordinary skill in the art will understand that a composition, such as an antibody, disclosed herein is efficacious in treating or inhibiting eosinophils in a subject by observing that the composition reduces eosinophil numbers.

The compositions that inhibit eosinophil development disclosed herein may be administered prophylactically to patients or subjects who are at risk for diseases related to eosinophils, such as asthma.

The disclosed compositions and methods can also be used for example as tools to isolate and test new drug candidates for a variety of eosinophil-related diseases.

9. Chips and Micro Arrays

Disclosed are chips where at least one address is the sequences or part of the sequences set forth in any of the nucleic acid sequences disclosed herein. Also disclosed are chips where at least one address is the sequences or portion of sequences set forth in any of the peptide sequences disclosed herein.

Also disclosed are chips where at least one address is a variant of the sequences or part of the sequences set forth in any of the nucleic acid sequences disclosed herein. Also disclosed are chips where at least one address is a variant of the sequences or portion of sequences set forth in any of the peptide sequences disclosed herein.

10. Screening Methods

Disclosed herein are methods of screening for inhibitors of eosinophil development. Lidocaine inhibits interleukin-5 (IL-5) mediated survival and activation of human eosinophils and is able to replace inhaled glucocorticoids for the treatment of asthma; however, lidocaine has many undesired side effects. Consequently, a collection of compounds, including commercially available lidocaine analogs and synthesized compounds designed by modification of lidocaine structure, were investigated for inhibitory activity on the proliferation of TF-1 cells, a CD34+cytokine dependent erythroleukemic cell line model for eosinophil development (Example 5).

TF-1 cell proliferation assays can be performed in order to identify compounds that can inhibit eosinophil development. The compounds can act in a variety of ways, such as inhibiting IL-5 or EGO mRNA.

Also disclosed herein are methods of inhibiting or reducing eosinophil development comprising exposing a cell to any of the compounds disclosed herein, such as those found in tables 5 and 6. Also disclosed are methods of treating a subject in need thereof by administering to the subject an effective amount of one or more of the compounds disclosed herein.

11. Compositions Identified by Screening with Disclosed Compositions/Combinatorial Chemistry a) Combinatorial Chemistry The disclosed compositions can be used as targets for any combinatorial technique to identify molecules or macromolecular molecules that interact with the disclosed compositions in a desired way. Also disclosed are the compositions that are identified through combinatorial techniques or screening techniques in which the compositions herein, or portions thereof, are used as the target in a combinatorial or screening protocol.

It is understood that when using the disclosed compositions in combinatorial techniques or screening methods, molecules, such as macromolecular molecules, will be identified that have particular desired properties such as inhibition or stimulation or the target molecule's function. The molecules identified and isolated when using the disclosed compositions, such as, EGO, are also disclosed. Thus, the products produced using the combinatorial or screening approaches that involve the disclosed compositions, such as, EGO, are also considered herein disclosed.

It is understood that the disclosed methods for identifying molecules that inhibit the interactions between, for example, EGO and eosinophils, can be performed using high through put means. For example, putative inhibitors can be identified using Fluorescence Resonance Energy Transfer (FRET) to quickly identify interactions. The underlying theory of the techniques is that when two molecules are close in space, ie, interacting at a level beyond background, a signal is produced or a signal can be quenched. Then, a variety of experiments can be performed, including, for example, adding in a putative inhibitor. If the inhibitor competes with the interaction between the two signaling molecules, the signals will be removed from each other in space, and this will cause a decrease or an increase in the signal, depending on the type of signal used. This decrease or increasing signal can be correlated to the presence or absence of the putative inhibitor. Any signaling means can be used. For example, disclosed are methods of identifying an inhibitor of the interaction between any two of the disclosed molecules comprising, contacting a first molecule and a second molecule together in the presence of a putative inhibitor, wherein the first molecule or second molecule comprises a fluorescence donor, wherein the first or second molecule, typically the molecule not comprising the donor, comprises a fluorescence acceptor; and measuring Fluorescence Resonance Energy Transfer (FRET), in the presence of the putative inhibitor and the in absence of the putative inhibitor, wherein a decrease in FRET in the presence of the putative inhibitor as compared to FRET measurement in its absence indicates the putative inhibitor inhibits binding between the two molecules. This type of method can be performed with a cell system as well.

Combinatorial chemistry includes but is not limited to all methods for isolating small molecules or macromolecules that are capable of binding either a small molecule or another macromolecule, typically in an iterative process. Proteins, oligonucleotides, and sugars are examples of macromolecules. For example, oligonucleotide molecules with a given function, catalytic or ligand-binding, can be isolated from a complex mixture of random oligonucleotides in what has been referred to as "in vitro genetics" (Szostak, *TIBS* 19:89, 1992). One synthesizes a large pool of molecules bearing random and defined sequences and subjects that complex mixture, for example, approximately $10^{15}$ individual sequences in 100 µg of a 100 nucleotide RNA, to some selection and enrichment process. Through repeated cycles of affinity chromatography and PCR amplification of the molecules bound to the ligand on the column, Ellington and Szostak (1990) estimated that 1 in $10^{10}$ RNA molecules folded in such a way as to bind a small molecule dyes. DNA molecules with such ligand-binding behavior have been isolated as well (Ellington and Szostak, 1992; Bock et al, 1992). Techniques aimed at similar goals exist for small organic molecules, proteins, antibodies and other macromolecules known to those of skill in the art. Screening sets of molecules for a desired activity whether based on small organic libraries, oligonucleotides, or antibodies is broadly referred to as combinatorial chemistry. Combinatorial techniques are particularly suited for defining binding interactions between molecules and for isolating molecules that have a specific binding activity, often called aptamers when the macromolecules are nucleic acids.

There are a number of methods for isolating proteins which either have de novo activity or a modified activity. For example, phage display libraries have been used to isolate numerous peptides that interact with a specific target. (See for example, U.S. Pat. Nos. 6,031,071; 5,824,520; 5,596,079; and 5,565,332 which are herein incorporated by reference at least for their material related to phage display and methods relate to combinatorial chemistry)

Using methodology well known to those of skill in the art, in combination with various combinatorial libraries, one can isolate and characterize those small molecules or macromolecules, which bind to or interact with the desired target. The relative binding affinity of these compounds can be compared and optimum compounds identified using competitive binding studies, which are well known to those of skill in the art.

Techniques for making combinatorial libraries and screening combinatorial libraries to isolate molecules which bind a desired target are well known to those of skill in the art. Representative techniques and methods can be found in but are not limited to U.S. Pat. Nos. 5,084,824, 5,288,514, 5,449,754, 5,506,337, 5,539,083, 5,545,568, 5,556,762, 5,565,324, 5,565,332, 5,573,905, 5,618,825, 5,619,680, 5,627,210, 5,646,285, 5,663,046, 5,670,326, 5,677,195, 5,683,899, 5,688,696, 5,688,997, 5,698,685, 5,712,146, 5,721,099, 5,723,598, 5,741,713, 5,792,431, 5,807,683, 5,807,754, 5,821,130, 5,831,014, 5,834,195, 5,834,318, 5,834,588, 5,840,500, 5,847,150, 5,856,107, 5,856,496, 5,859,190, 5,864,010, 5,874,443, 5,877,214, 5,880,972, 5,886,126, 5,886,127, 5,891,737, 5,916,899 , 5,919,955, 5,925,527, 5,939,268, 5,942,387, 5,945,070, 5,948,696, 5,958,702, 5,958,792, 5,962,337, 5,965,719, 5,972,719, 5,976,894, 5,980,704, 5,985,356, 5,999,086, 6,001,579, 6,004,617, 6,008,321, 6,017,768, 6,025,371, 6,030,917, 6,040,193, 6,045,671, 6,045,755, 6,060,596, and 6,061,636.

Combinatorial libraries can be made from a wide array of molecules using a number of different synthetic techniques. For example, libraries containing fused 2,4-pyrimidinediones (U.S. Pat. No. 6,025,371) dihydrobenzopyrans (U.S. Pat. Nos. 6,017,768 and 5,821,130), amide alcohols (U.S. Pat. No. 5,976,894), hydroxy-amino acid amides (U.S. Pat. No. 5,972,719) carbohydrates (U.S. Pat. No. 5,965,719), 1,4-benzodiazepin-2,5-diones (U.S. Pat. No. 5,962,337), cyclics U.S. Pat. No. 5,958,792), biaryl amino acid amides (U.S. Pat. No. 5,948,696), thiophenes (U.S. Pat. No. 5,942,387), tricyclic Tetrahydroquinolines (U.S. Pat. No. 5,925,527), benzofurans (U.S. Pat. No. 5,919,955), isoquinolines (U.S. Pat. No. 5,916,899), hydantoin and thiohydantoin (U.S. Pat. No. 5,859,190), indoles (U.S. Pat. No. 5,856,496), imidazol-pyrido-indole and imidazol-pyrido-benzothiophenes (U.S. Pat. No. 5,856,107) substituted 2-methylene-2,3-dihydrothiazoles (U.S. Pat. No. 5,847,150), quinolines (U.S. Pat. No. 5,840,500), PNA (U.S. Pat. No. 5,831,014), containing tags (U.S. Pat. No. 5,721,099), polyketides (U.S. Pat. No. 5,712,146), morpholino-subunits (U.S. Pat. Nos. 5,698,685 and 5,506,337), sulfamides (U.S. Pat. No. 5,618,825), and benzodiazepines (U.S. Pat. Nos. 5,288,514).

b) Computer Assisted Drug Design

The disclosed compositions can be used as targets for any molecular modeling technique to identify either the structure of the disclosed compositions or to identify potential or actual molecules, such as small molecules, which interact in a desired way with the disclosed compositions.

It is understood that when using the disclosed compositions in modeling techniques, molecules, such as macromolecular molecules, will be identified that have particular desired properties such as inhibition or stimulation or the target molecule's function. The molecules identified and isolated when using the disclosed compositions, such as, EGO, are also disclosed. Thus, the products produced using the molecular modeling approaches that involve the disclosed compositions, such as, EGO, are also considered herein disclosed.

Thus, one way to isolate molecules that bind a molecule of choice is through rational design. This is achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 *Acta Pharmaceutica Fennica* 97, 159-166; Ripka, *New Scientist* 54-57 (Jun. 16, 1988); McKinaly and Rossmann, 1989 *Annu. Rev. Pharmacol. Toxiciol.* 29, 111-122; Perry and Davies, *OSAR: Quantitative Structure-Activity Relationships in Drug Design* pp. 189-193 (Alan R. Liss, Inc. 1989); Lewis and Dean, 1989 *Proc. R. Soc. Lond.* 236, 125-140 and 141-162; and, with respect to a model enzyme for nucleic acid components, Askew, et al., 1989 *J. Am. Chem. Soc.* 111, 1082-1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of molecules specifically interacting with specific regions of DNA or RNA, once that region is identified.

Although described above with reference to design and generation of compounds which could alter binding, one could also screen libraries of known compounds, including natural products or synthetic chemicals, and biologically active materials, including proteins, for compounds which alter substrate binding or enzymatic activity.

12. Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include primers to perform the amplification reactions discussed in certain embodiments of the methods, as well as the buffers and enzymes required to use the primers as intended.

13. Compositions with Similar Functions

It is understood that the compositions disclosed herein have certain functions, such as binding EGO or interacting with eosinophils. Disclosed herein are certain structural requirements for performing the disclosed functions, and it is understood that there are a variety of structures which can perform the same function which are related to the disclosed structures, and that these structures will ultimately achieve the same result, for example inhibition of eosinophils.

E. METHODS OF MAKING THE COMPOSITIONS

The compositions disclosed herein and the compositions necessary to perform the disclosed methods can be made using any method known to those of skill in the art for that particular reagent or compound unless otherwise specifically noted.

1. Nucleic Acid Synthesis

For example, the nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook et al., *Molecular Cloning: A Laboratory Manual*, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System iPlus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323-356 (1984), (phosphotriester and phosphite-triester methods), and Narang et al., *Methods Enzymol.*, 65:610-620 (1980), (phosphotriester method). Protein nucleic acid molecules can be made using known methods such as those described by Nielsen et al., *Bioconjug. Chem.* 5:3-7 (1994).

2. Process for Making the Compositions

Disclosed are processes for making the compositions as well as making the intermediates leading to the compositions. There are a variety of methods that can be used for making these compositions, such as synthetic chemical methods and standard molecular biology methods. It is understood that the methods of making these and the other disclosed compositions are specifically disclosed.

Disclosed are nucleic acid molecules produced by the process comprising linking in an operative way a nucleic acid comprising the sequence set forth herein and a sequence controlling the expression of the nucleic acid.

Also disclosed are nucleic acid molecules produced by the process comprising linking in an operative way a nucleic acid molecule comprising a sequence having 80% identity to a sequence set forth herein, and a sequence controlling the expression of the nucleic acid.

Disclosed are nucleic acid molecules produced by the process comprising linking in an operative way a nucleic acid molecule comprising a sequence that hybridizes under stringent hybridization conditions to a sequence set forth herein, and a sequence controlling the expression of the nucleic acid.

Disclosed are cells produced by the process of transforming the cell with any of the disclosed nucleic acids. Disclosed are cells produced by the process of transforming the cell with any of the non-naturally occurring disclosed nucleic acids.

Disclosed are any of the disclosed peptides produced by the process of expressing any of the disclosed nucleic acids. Disclosed are any of the non-naturally occurring disclosed peptides produced by the process of expressing any of the disclosed nucleic acids. Disclosed are any of the disclosed peptides produced by the process of expressing any of the non-naturally disclosed nucleic acids.

Disclosed are animals produced by the process of transfecting a cell within the animal with any of the nucleic acid molecules disclosed herein. Disclosed are animals produced by the process of transfecting a cell within the animal any of the nucleic acid molecules disclosed herein, wherein the animal is a mammal. Also disclosed are animals produced by the process of transfecting a cell within the animal any of the nucleic acid molecules disclosed herein, wherein the mammal is mouse, rat, rabbit, cow, sheep, pig, or primate.

Also disclose are animals produced by the process of adding to the animal any of the cells disclosed herein.

F. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

Non-Coding RNA as a Regulator of Hematopoiesis: EGO, a Nested RNA Gene Regulates Human Eosinophil Development a) Microarray Genes involved in early eosinophil development were investigated by gene expression profiling. Affymetrix HG-U133 A human microarray chips were hybridized with labeled antisense RNA amplified from CD34+ human hematopoietic stem cells cultured for 24 hours in IL-5, an eosinophil specific cytokine, or epoietin-α as a control. Arrays were normalized by GC-RMA and increased transcript levels were analyzed using rank based statistics (Breitling et al. 2005). The top thirty eight ranked genes have transcript levels at least four fold higher in IL-5 treated cells compared to control (Table 1). Several interleukins, interleukin receptors and chemokine receptor transcripts are increased in response to IL-5: CXCL13, IL-6, IL-1 family members as well as IL-12B and IL21R have increased mRNA levels. COX-2, a gene involved in inflammatory prostaglandin synthesis is also differentially upregulated. In addition, two transcription factors, WT-1 and HEY1 increase in transcriptional expression following IL-5 treatment. Of particular interest, one transcript, (Affymetrix 2223 14_x_at) is nested within an intron on the opposite strand of the Inositol Triphosphate Receptor Type1 (ITPR1) gene. This transcript is interesting because of its inducible expression to high transcript levels, conservation and lack of a large open reading frame (FIG. 1). This gene was named EGO (Eosinophil Granule Ontogeny).

b) Gene Structure

Two splice variants of the EGO transcript were found using a BLAT Search (May 2004 Assembly) (FIG. 1). The splice variant found by array analysis was named EGO-A and the cDNA (GenBank Accession # AW970881) is 535 bases long (FIG. 1B). In addition, a two exon splice variant, EGO-B, (GenBank Accession #BC039547) is 1460 bases (FIG. 1B). However, northern blot analysis using RNA isolated from TF-1 cells, a CD34+erythroleukemic cell line, and a probe to a unique region of EGO-A revealed a 1 kb polyadenylated transcript, showing that the reported cDNA is truncated (FIG. 2). RT-PCR data is consistent with EGO-A extending over 300 bases towards the 5' end of the transcript (additional bases in the poly A tail may add 100-200 bases). A northern blot using a probe in exon 2 of EGO-B shows an approximately 1700 base polyadenylated transcript, which is consistent with GenBank data for the BC09547 cDNA (FIG. 2). PCR and sequence data also shows that the 5' splice junction for EGO-B is 46 bases upstream from the reported BC039547 cDNA splice site (FIG. 2) (4767665-476655 TTCTATCAG (SEQ ID NO: 1) . . . GCACGATGGT (SEQ ID NO: 2). Based on the single stranded probes in the Affymetrix arrays, both EGO-A and B are sense on the —strand of genomic DNA, the opposite strand from ITPR-1 transcription. The multiple overlapping transcripts derived from both strands in this region are characteristic of an RNA forest (Caminci et al. 2005). Therefore, at least two EGO transcripts are transcribed within an intron on the opposite strand from ITPR1.

c) Conservation

Vista tracks on the UCSC (University of Santa Cruz) browser show that conservation of the region within the large intron of ITPR-1 that includes the EGO gene is high between human, mouse, and chicken (FIG. 1). However, the highest region of homology, close to 90% identity, is in the intron of EGO-B, showing an additional undiscovered gene or a regulatory region. The 3' portion of EGO-A has approximately 75% identity between mouse and human (FIG. 1). However, no long coding region was found in EGO-A or B and small coding regions are not conserved between mouse and human. Furthermore, non-coding RNA (ncRNA) genes are often found within introns and untranslated regions of coding genes (Carninci et al. 2005, Ravasi et al. 2006). NcRNA genes are often inferred by the lack of large open reading frames or conserved amino acid sequence. Therefore, the hypothesis that EGO is an ncRNA gene was investigated further.

d) Sucrose Gradient Analysis of ncRNA

The hypothesis that EGO is an ncRNA was tested by measuring the transcript's association with ribosomes by sucrose density gradient sedimentation. Sucrose density gradient sedimentation was performed on lysates from CD34+ umbilical cord blood cells stimulated for 24 hours with IL-5 to determine if EGO is in the same fraction as ribosomes or polyribosomes. Absorbance at 260 nm wavelength per fraction gives a characteristic plot in which ribosomes are concentrated at the bottom of the sucrose gradient. In this gradient, UV absorbance in fractions 1 and 3 are indicative of polysomes and fraction 7 corresponds to single ribosomes (FIG. 3A). RT-PCR was performed on each fraction for α-tubulin mRNA and for EGO-A and B transcript expression. As expected, α-tubulin transcripts are mainly associated with polysomes in fraction 3 (FIG. 3B). In contrast, both EGO-A and B transcripts levels are more abundant in the lighter fractions of the gradient, in fractions 13 and 17, respectively (FIGS. 3C and D). These data show that EGO transcripts are not associated with ribosomes in umbilical cord blood CD34+cells in vitro after stimulation for 24 hours with IL-5.

e) EGO Gene Expression

Figure 4C:
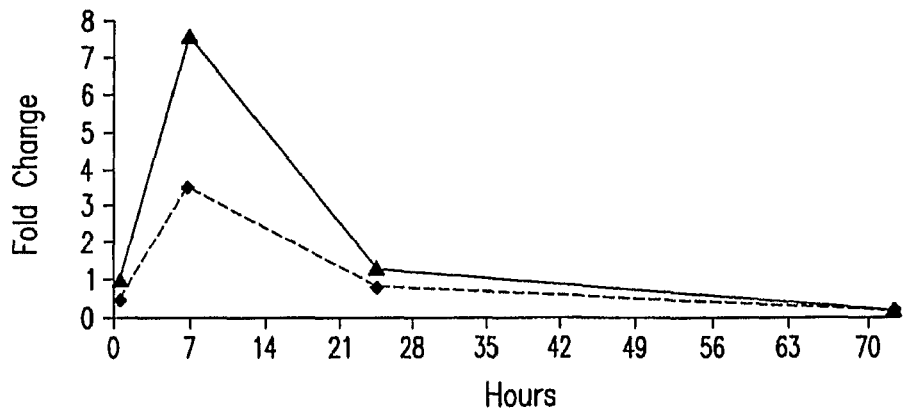

The induction of expression of EGO-A and B RNA was investigated by real time Q-RT-PCR (quantitative reverse transcriptase polyrnerase chain reaction) of CD34+ cells derived from umbilical cord blood and stimulated with IL-5 for various times. EGO-A and B are highly expressed, over 20 fold above the initial time point, at 6 hours after IL-5 addition (FIG. 4A). EGO RNA expression is reduced to initial levels by 72 hours after stimulation (FIGS. 4A and B). The specificity of EGO RNA expression in various developing cell types was investigated by real time Q-RT-PCR of umbilical cord blood CD34+ cells grown on cytokines that support erythrocyte (epoietin-α), mast cell (SCF), monocyte (M-CSF/GM-CSF), multilineage (IL-3) and neutrophil (GM-CSF/G-CSF) differentiation. All cytokines except SCF cause a slight increase in EGO-A and B expression, showing that EGO transcription can also be involved in other myeloid lineages. Expression of EGO-A and B in IL-5 stimulated CD34+ bone marrow cells follows a similar temporal pattern (FIG. 4C). These results show that EGO-A and B RNA are expressed coordinately very early and briefly in eosinophil development in vitro in both bone marrow and umbilical cord blood derived CD34+ cells stimulated with IL-5.

The relative expression of EGO in a panel of human tissue types was investigated by real time Q-RT-PCR. Tissue expression of both EGO-A and B RNA is 2000-7000 higher in bone marrow mononuclear cells and bone marrow CD34+ cells than in brain, the tissue with the lowest expression. Expression of both EGO transcripts is also high in kidney. EGO-B RNA is highly expressed in leukocytes and pancreas relative to EGO-A. The expression of EGO in bone marrow is consistent with a developmental role for EGO in hematopoiesis.

f) The Role of EGO in Development

Figure 5A:
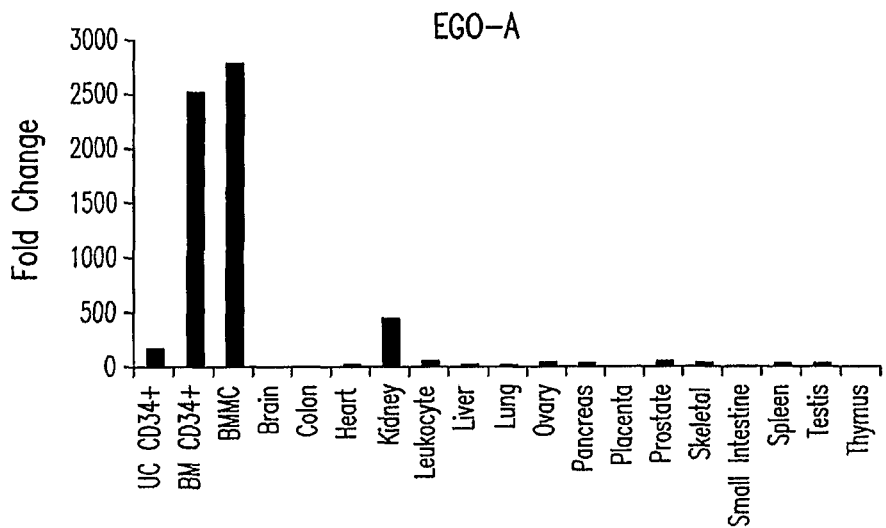

RNA silencing experiments were initiated in order to test the hypothesis that EGO expression influences eosinophil differentiation. TF-1 is a CD34+ erythroleukemic cell line that can be growth stimulated with various cytokines, including IL-5. A short hairpin RNA (shRNA) expression plasmid containing either scrambled control sequences (pSi1 Neg) or sequences simultaneously targeting both variants of EGO (pSi1 20-2) for silencing were transfected into TF-1 cells. Plasmids also contained a green fluorescent protein (GFP) reporter gene. TF-1 cells were sorted to at least 90% purity for GFP positive cells 24 hours after transfection. Real time Q-RT-PCR of RNA isolated from GFP+ cells was used to quantitate silenced levels of EGO RNA using primers abutting the RNA cut site and α-tubulin primers as a control. Levels of EGO are diminished to 35% (65% knockdown) in the cells transfected with the shRNA plasmid directed at EGO transcripts compared to the negative control. Levels of MBP and EDN mRNA, which are expressed at low levels in TF-1 cells, were also measured by Q-RT-PCR. In cells in which EGO transcripts had been silenced, levels of MBP mRNA are 23% of control, and EDN mRNA levels are 52% of control levels, suggesting that diminished EGO RNA levels decrease eosinophil granule protein transcription (FIG. 5A).

CD34+ cells derived from umbilical cord blood (UCB) are a better model of eosinophil differentiation than TF-1 cells, because IL-5 stimulated CD34+ UCB cells develop into mature eosinophils whereas TF-1 cells simply proliferate in response to a variety of cytokines. CD34+UCB cells express MBP mRNA at 72 hours after IL-5 stimulation and have immature granules at 1 week. CD34+ cells were transfected with shRNA plasmids, sorted for >90% pure GFP+ cells less than 24 hours after transfection and grown for 5 days on IL-5. Prior experiments showed that the pSi1 20-2 plasmid reduced EGO transcripts to 40% of control. RNA was isolated and Q-RT-PCR performed to quantitate granule protein mRNA levels. MBP mRNA levels are reduced to 22% in EGO silenced cells as compared to controls and levels of EDN mRNA are 59% of control levels. These data show that EGO RNA is necessary for eosinophil development.

g) Methods (1) CD34+ Isolation and Cell Culture

CD34+ cells were enriched to 60-80% purity from mononuclear cord blood cells or bone marrow mononuclear cells using the Miltenyi Midi Macs System and the StemSep CD34+ Human Selection kit following permission from the University of Utah Institutional Review Board (IRB). Bone marrow was obtained by informed consent from normal patients after permission from the University of Utah IRB. Cells were cultured in RPMI with glutamine, penicillin/streptomycin, 10% Fetal Calf Serum (Hyclone) and 5 ng/ml IL-5 (R&D Systems) or frozen in 10% DMSO for later use. 500,000 cells were cultured per well in a 48 well flat bottom plate. CD34+ cells were stimulated with the following cytokines: 2 U/ml epogen (epoietin-α), 50 ng/ml SCF; 20 ng/ml GM-CSF, 50 ng/ml M-CSF; 20 ng/ml GM-CSF, 50 ng/ml G-CSF; 20ng/ml IL-3. RNA was isolated at the following time points: 0 hours, 6 hours, 24 hours, and 72 hours. TF-1 cells were grown in RPMI, 10% FCS, Gln, P/S and 5 ng/ml IL-5 or 2 μ/ml epogen.

Microarray: CD34+ cells were isolated from the umbilical cord blood of three placentas. Following 24 hours of culture in 5 ng/ml IL-5 or 2 μ/ml epoietin-α, total RNA was isolated and amplified using the Arcturus Riboamp RNA amplification kit. Labeling and hybridization of amplified antisense RNA to Affymetrix U133A DNA chips was done in triplicate according to the manufacturer's instructions. Data was analyzed using GC-RMA and ranked with non-parametric statistics.

Quantitative RT-PCR: Total RNA was isolated using the Qiagen Rneasy kit. First strand cDNA was synthesized using the Superscript III Kit (Invitrogen). PCR conditions were 2 mM dNTPs, 0.5 uM primers, 1/30,000 Sybr Green I, 0.5 UAmplitaq (ABI), 0.1 ug Taqstart antibody (Clontech), 4 mM PCR buffer (Idaho Technology, SLC, UT) and 4 ul 10× diluted cDNA in a 20 ul reaction. PCR was done in triplicate on a Roche LightCycler and averages were plotted. Second derivative maxima of triplicates are within a half cycle of each other or were repeated. Parameters were 94oC for 0 seconds, 60oC for 20 seconds, 40 cycles. All reactions are normalized to an α-tubulin control (Bernard and Wittwer 2002). Efficiency of the tubulin primers is 2.0 and efficiency of all other primers is assumed to be 2.0. Second derivative maxima were used from LightCycler Data Analysis v3.5 to quantitate RNA levels. Primers for EGO A are BCOF1 (cttctcctccaggccatacc SEQ ID NO: 3) and 222314(ccattgtgtagccccg SEQ ID NO: 4). Primers for EGO B are egosp1R2 (ccatcgtgcctgataaa (SEQ ID NO: 5) and BCOF1. Primers for granule proteins are EDNF2 (caccatggttccaaaactgttca SEQ ID NO: 6), EDNR2 (gttttccatcgccgtt SEQ ID NO: 7), MBPF (gggattgcggtacttataca SEQ ID NO: 8), MBPR (atgggctcagctagtt SEQ ID NO: 9). Primers to measure silencing are 222314F8 (aggaattatgattgtggggt SEQ ID NO: 10) and BCO39547R3 (ggtatggcctggaggagaag SEQ ID NO: 11). All amplicons are a single band on agarose gels and were verified by DNA sequencing.

Northern blot: 0.5-1 μg of Poly A+ RNA (Qiagen Oligotex kit) was electrophoresed on a 1% MOPS formaldehyde gel alongside Millennium Markers (Ambion). Markers were stained in 1×TBE and Sybr Gold (Molecular Probes). Gels were transferred to nitrocellulose membranes in 6×SSC (or to GeneScreen for EGO-B) and hybridized overnight at 42oC in 50% formamide to radiolabeled random primed EGO-A or B PCR products (see above), washed 3× in 48° C. 2×SSC and 55° C. 0.2×SSC, the exposed to film.

Sucrose gradients: Approximately 7×106 CD34+ cells were cultured for 24 h in 5 ng/ml IL-5. Cells were disrupted by Dounce homogenization and layered on a 10-50% sucrose gradient. Gradients were centrifuged for 4 hours at 38,000 rpm in a swinging bucket SW40Ti rotor. 0.5 ml fractions were collected from the bottom; total RNA was isolated by phenol/chloroform purification and ethanol precipitation. OD260 readings were taken on each fraction to determine the location of the ribosomal peaks. RNA derived from fractions was reverse transcribed to cDNA and real time PCR was performed as described. Normalization to tubulin was not done due to the differential quantities of tubulin in fractions containing ribosomes.

Multiple tissue expression: Multiple tissue human cDNA panels I and II were purchased from BDBioscience Clontech. Bone marrow cDNA was isolated from human bone marrow obtained by informed consent from normal patients. Bone marrow and CD34+ cell cDNA was normalized to average tubulin Clontech panel values and fold changes were calculated as described above.

Plasmid construction: pSilencer 2.0-U6 (Ambion) was digested with HIII and blunt end cloned to Mlu I/AseI digested pEGFP-C1 (Clontech). The HIII site was not lost. The multiple cloning sites in the EGFP gene were removed by a BgIII/BamHI digest and religation. Subsequently, the sequence 5' gatcccaatagaaccgcaagaaaacaactcgagttgttttcttgcggttctattttttggaaa3' was cloned into the BamHI/HIII sites to create the shRNA plasmid pSi1 20-2 targeting EGO-A and B.

siRNA: CD34+ cells: Frozen cells were allowed to recover for one hour at 37oC 5% CO2 in 10 parts media prior to spinning out DMS0. Endotoxin free short hairpin plasmid DNA (1.0 ug) (Qiagen Endotoxin free kit) was electroporated into 1×106 CD34+ cells using the CD34+ Nucleofector kit and a Nucleofector device (Amaxa) using program U8. Cells were allowed to recover for 15 minutes in serum and antibiotic free media at 37oC 5% CO2. Cells were put in a 48 well flat bottom plate and RPMI, 10% FCS/Gln and pen/strep were immediately added. After 18 hours 5 ng/ml IL-5 was added (time=0') and GFP positive cells were purified on a FACS Vantage cell sorter at least 90% purity. Approximately 100, 000 cells were cultured in a single well of a 96 well round bottom plate. At the 24 hour time point and the 5 day time point total RNA was isolated. TF-1 cells: Cells were grown in RPMI 1640, 10% FCS, Gln and epoietin-α. Approximately 5×106 freshly cultured cells were electroporated on program T3 and V Nucleofector kit with 1-5 ug sh plasmid DNA. Cells were sorted for >90% pure GFP positive within 24 hours as above and RNA was isolated.

TABLE 1

Top 38 increased IL-5 specific transcripts.

| Probe set* | Gene | Description | Fold Change** |
|---|---|---|---|
| 205242_at | CCL13 | chemokine (C-X-C motif) ligand 13 (B-cell chemoattractant) | 85 |
| 205207_at | IL6 | interleukin 6 (interferon, beta 2) | 25 |
| 220322_at | IL1F9 | interleukin 1 family, member 9 | 17 |
| 201860_s_at | PLAT | plasminogen activator, tissue | 13 |
| 210072_at | CCL19 | chemokine (C-C motif) ligand 19 | 9 |
| 206336_at | CXCL6 | chemokine (C-X-C motif) ligand 6 (granulocyte chemotactic protein 2) | 10 |
| 207533_at | CCL1 | chemokine (C-C motif) ligand 1 | 8 |
| 204470_at | CXCL1 | chemokine (C-X-C motif) ligand 1(melanoma growth stimulating) | 9 |
| 207901_at | IL12B | interleukin 12B (natural killer cell stimulatory factor 2) | 9 |
| 204748_at | PTGS2 | prostaglandin-endoperoxide synthase 2 (COX-2) | 9 |
| 209278_s_at | TFPI2 | tissue factor pathway inhibitor 2 | 9 |
| 221658_s_at | IL21R | interleukin 21 receptor | 7 |
| 219424_at | EBI3 | Epstein-Barr virus induced gene 3 (IL12R family) | 8 |
| 209774_x_at | CXCL2 | chemokine (C-X-C motif) ligand 2 (IL8RB) | 6 |
| 206432_at | HAS2 | hyaluronan synthase 2 | 8 |
| 44783_s_at | HEY1 | hairy/enhancer-of-split related with YRPW motif 1(transcription factor) | 6 |
| 211538_s_at | HSPA2 | heat shock 70 kDa protein 2 | 5 |
| 210511_s_at | INHBA | inhibin, beta A (activin A, activin AB alpha polypeptide) | 9 |
| 210001_s_at | SOCS1 | suppressor of cytokine signaling 1 | 5 |
| 207608_x_at | CYP1A2 | cytochrome P450, family 1, subfamily A, polypeptide 2 | 5 |
| 210029_at | INDO | indoleamine-pyrrole 2,3 dioxygenase | 6 |
| 219255_x_at | IL17RB | interleukin 17 receptor B | 6 |
| 204014_at | DUSP4 | dual specificity phosphatase 4 | 6 |
| 219258_at | FLJ20516 | timeless-interacting protein | 5 |
| 222314_x_at | ITPR1 | Inositol 1,4,5-triphosphate receptor, type 1 (intron of ITPR1, EGO) | 4 |
| 208581_x_at | MT1X | metallothionein 1X | 4 |
| 207526_s_at | IL1RL1 | interleukin 1 receptor-like 1 | 6 |
| 205599_at | TRAF1 | TNF receptor-associated factor 1 | 5 |
| 204580_at | MMP12 | matrix metallopeptidase 12 (macrophage elastase) | 6 |
| 203562_at | FEZ1 | fasciculation and elongation protein zeta 1 (zygin I) | 6 |
| 215223_s_at | SOD2 | superoxide dismutase 2, mitochondrial | 4 |
| 205114_s_at | CCL3 | chemokine (C-C motif) ligand 3 | 5 |
| 209369_at | ANXA3 | annexin A3 | 4 |
| 203881_s_at | DMD | dystrophin (muscular dystrophy, Duchenne and Becker types) | 5 |
| 206067_s_at | WT1 | Wilms tumor 1 (zinc finger, transcription factor) | 4 |
| 209277_at | TFPI2 | Tissue factor pathway inhibitor 2 | 5 |
| 206881_s_at | LILRA3 | leukocyte immunoglobulin-like receptor, subfamily A, member 3 | 4 |
| 202071_at | SDC4 | syndecan 4 (amphiglycan, ryudocan) | 4 |

*Affymetrix gene probe tags.
**Fold change relative to epoietin-α induced transcripts.

2. Example 2

Eosinophilopoiesis

IL-5 Stimulated CD34+ Cells from Cord Blood: A model for eosinophil development. An in vitro system of eosinophil development was chosen as a model of eosinophil development. Cells derived from umbilical cord blood and stimulated with IL-5 mature into an essentially pure population of eosinophils within 3 weeks.

Figure 7B:
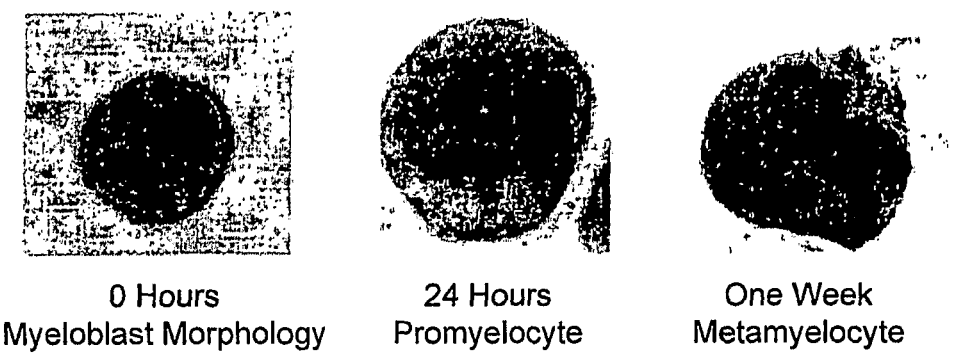

Morphology and Proliferation of Cord Blood Model System. Cord blood CD34+ cells differentiate rapidly in IL-5 containing media, (FIG. 7a) Freshly isolated CD34+ cells appear to have many cells with myeloblast morphology prior to stimulation. Following 24 hours of IL-5 stimulation, the nucleus shrinks substantially and many cells have promyelocyte morphology. At the one week timepoint, the nucleus becomes partially bilobed and granules can be seen which is characteristic of metamyelocytes (FIG. 7b). Most of the gross morphological changes leading to eosinophil development occur within the first week of culture.

Molecular Biology of Model System. The molecular timing of eosinophil development in vitro was also investigated by real time quantitative RT-PCR analysis of granule protein and transcription factor mRNA. Real time PCR is a fluorescent based PCR in which the amplified DNA present at each cycle is recorded and graphed on a computer. In this manner, quantitative information, which is most accurate in the early exponential cycles of PCR, before plateau occurs, can be accurately assessed. The crossing point or second derivative maximum (maximum rate of change) reflects the point at which fluorescent product comes out of background and is the used to quantitate starting amounts of cDNA in the reaction. Each PCR reaction is normalized to α-tubulin mRNA (by PCR) to control for varying amounts of cells and RNA recovery from the initial cultures. In this manner, accurate quantitative information can be obtained from a small amount of starting product.

The results show that the mRNA for the granule protein, EDN, is transcribed after one week of IL-5 stimulation (FIG. 8A). MBP is transcribed at 72 hours, although transcription increases to two weeks (FIG. 8B). As expected, C/EBPε mRNA is transcribed earlier with transcripts detectable by 24 hours (FIG. 8C). As C/EBPε is considered a late transcription factor, causing arrest in the myelocyte to metamyelocyte stage in C/EBPε (---)mice, it is reasonable to assume that a considerable amount of transcriptional activity occurs in the first 24 hours after IL-5 stimulation in vivo. Another possible explanation is that the early rise in C/EBPε transcripts is due to CD34+ stem cells that are already developing into eosinophils. However, this is unlikely because developing eosinophils lose the CD34 marker rapidly during development and would not be isolated by our CD34+ selection system. Therefore, a microarray analysis on RNA derived from cells after 24 hours of stimulation with interleukin-5 was done in order to discover early developmental genes.

Microarray Discovery of Novel Genes in Eosinophilopoesis: A microarray experiment was designed to identify transcripts that are upregulated in early eosinophil development. CD34+ cells derived from cord blood were stimulated for 24 hours in vitro to initiate eosinophilopoiesis. Erythropoiesis of CD34+ cord blood cells stimulated by erythropoietin for 24 hours was used as a control for general proliferation due to cytokine stimulation. Affymetrix microarrays were done in triplicate throughout the experiment to control for patient and gene chip variability. GeneSpring Software was used to identify genes that were upregulated at least four fold relative to control. This analysis produced 38 genes that were upregulated by IL-5 stimulation as compared to erythropoietin stimulation (Table 1). Upregulated genes are mainly cytokines and chemokines and their receptors. Some matrix metalloproteases are upregulated as well.

Real Time Quantitative RT-PCR Confirmation of Microarray Results. The IL-5 stimulated upregulation of the novel and selected known genes discovered by microarray was confirmed by real time RT-PCR of RNA derived from cultured CD34+ cells (Table 2). RNA was derived from separate cord blood cultures not used in the arrays to obtain unbiased results. Upregulation was confirmed to be between 2-1 00 fold when stimulated with IL5 relative to erythropoietin for all genes for which confirmation was attempted.

TABLE 2

Real-time RT-PCR confirmation of micro array. Methods are as in FIG. 1. * Two cord blood donors gave different fold changes.

| Affymetrix Number | Genbank Number | Fold Change | Gene |
|---|---|---|---|
| 222314 at | AW970881 | 5.6, 22.1 * | Unknown (FOE) |
| 227140 at | A1343467 | 8.6 | unknown |
| 235830 at | A1797043 | 5.3 | unknown |
| 230127 at | AW044663 | 6.0 | unknown |
| 231804 at | A1805323 | 8.5 | Leucine rich repeat |
| 205242 at | NM 006419.1 | 100 | SIC 13 |
| 242809 at | A1188516 | 2.1 | unkown |
| 209227 at | AL574096 | 19 | TFPI |
| 237753 at | AW504569 | 2.5 | unkown |
| 229437 at | BG231961 | 45 | BIC |
| 227099 sat | AW276078 | 2.3 | unknown |

AW970881 and A1343467 were selected tbr more mtensive study on the basis of their novelty and dramatic fold change during IL-5 stimulation. AW970881 was provisionally named FOE (Friend of Eosinophil) for simplicity. A two week time course measuring mRNA production in 1L-5 stimulated cells relative to erythropoeitin was conducted. All three of these genes were upregulated strikingly at 6 hours to 24 hours with a rapid decrease in expression to baseline at 72 hours. Therefore, these genes are transcribed rapidly and transiently at approximately 6-24 hours after interleukin-5 stimulation and are degraded to baseline levels by 72 hours.

Gene Hunt. The structure of the FOE gene was investigated using the BLAT program on the University of Santa Cruz website. The Affymetrix tag and Genbank sequence AW970881 (the FOE gene) maps within an intron of the inositol 1,4,5-triphospate type I (ITPR1) gene on the —strand of chromosome 3p26.1. At least two introns and perhaps a third upstream intron are present in the gene. The degree of conservation to the mouse genomic sequence is quite high; L scores of 2-3 are present in most exons representing a probability of .01-0.001 that conservation is not due to chance. Identity ranges from 54.9-72.5% in exons 1 and 2. No large open reading frames exist in the gene, suggesting that the protein is small or that it is an untranslated gene.

Probing Gene Function with RNA Silencing; FOE inhibits granule protein expression. To determine the function of novel genes in eosinophil development, small, interfering RNAs (siRNAs) were used to "knock down" or silence transcripts. This method takes advantage of a double stranded RNA degrading system that is intrinsic to many species. Transfection of a double stranded RNA causes cutting of the RNA into 21 basepair pieces by an enzyme called Dicer. The resulting siRNAs then unwind and bind to homologous mRNA at a target site which is in turn cleaved by an enzyme complex called RISC (RNA Induced Silencing Complex). In human cells, siRNA fragments are directly transfected into cells in order to avoid a global RNA degrading host defense against viruses that is activated by larger dsRNA. RNA silencing has the advantage that one needs to know the sequence of only a small portion of a gene in order to silence it.

Initially, the Lamin A/C gene was silenced as a positive control in CD34+cells using a published target sequence (51). A stem loop region containing the target region of the Lamin A/C was cloned into the pSilencer 2.0-U6 plasmid (Ambion).

This plasmid expresses a hairpin RNA from a U6 RNA polymerase III promoter after transfection. pSilencer Negative plasmid was used as a negative control. The pSilencer Negative plasmid (Ambion) is a scrambled stem loop sequence that isn't homologous to human mRNA. Because antibodies aren't available, RT-PCR is used to detect mRNA knockdown. Silenced mRNA may not be completely degraded into single nucleotides immediately, therefore, PCR primers are used that span the cut site. Silencing of the gene was >90% as reported (FIG. 11). This is the first report that shows that siRNA silences a gene in CD34+stem cells.

Silencing of CD34+ cells was quite effective; therefore knock down FOE expression using the same procedure was attempted. Stem-loop regions encompassing two target regions were chosen using the Ambion siRNA Target Finder program. Potential target regions were entered into the Blast program on the NCBI website to find those that are not homologous to other human genes. The stem-loop regions were cloned into the pSilencer plasmid, sequenced and transfected into CD34+ cells. pSilencer Negative plasmids were used as a control. RNA was isolated from cultures at 6.0 hours and 72 hours after IL-5 stimulation. The plasmid, pSilencer #20, knocks down FOE transcript levels by approximately 8.0 fold at the 6 hour timepoint when transcript levels are usually highest (Table 3). To determine if FOE knockdown has an effect on eosinophil development, granule protein mRNA levels were also investigated by RT-PCR. Interestingly, at 72 hours when MBP transcripts are usually first appearing, no transcripts are present in FOE silenced cultures although MBP mRNA is present in normal levels in the pSilencer Negative controls (FIG. 12). This shows that expression of FOE is critical to MBP expression.

TABLE 4

FOE Silencing by siRNA.

| Construct | 33.5 |
|---|---|
| pSilencer Negative | 33.9 |
| pSilencer #20 | 36 |
| pSilencer #20 | Not detected |

Results show that 8 novel genes as well as 27 described genes are dramatically upregulated during the first 24 hours of eosinophil development. Furthermore, RNA silencing experiments show that expression of FOE transcripts is critical to normal eosinophilopoeisis.

FOE is transcribed within an intron of the ITPR1 gene on the minus strand (the opposite strand of the ITPR1 transcript). At least two exons with several small open reading frames have been found. Therefore, the mRNA structure and predicted protein sequence of FOE can be investigated by constructing a cDNA library and sequencing clones that hybridize to labeled sequences derived from exon 1 and the putative 5' exon. ORFs can be closely compared to mouse sequence to look for conserved amino acid sequence and silent substitutions. Polyclonal antibodies can be raised to selected peptides in the predicted open reading frame(s). Furthermore, the possibility that FOE is a non-coding RNA (ncRNA) gene can be investigated by looking for FOE transcripts in polysomal sucrose gradient fractions versus less dense fractions that could contain ncRNAs.

The FOE cDNA can be cloned from an IL-5 stimulated CD34+ cord blood library. The cDNA library can be constructed from PCR amplified mRNA because of the difficulty in obtaining large amounts of CD34+ cells. This method allows library construction from as little as 50 ng of total RNA. Northern blot gives the predicted size of the RNA. The library can be probed with a radiolabeled cloned fragment of the 5' exon as predicted by northern blot. cDNA clones can be verified as full length by comparing cDNA size to IL-5 stimulated CD34+ mRNA size by northern blot. The FOE cDNA can be sequenced and compared to the human genome sequence and the predicted open reading frame (ORF) can be determined. All ORFs can be carefully compared to mouse sequence to look for conservation of amino acid sequence and silent substitutions. This sequence information can be used to search for motifs and similarities to known classes of proteins.

NcRNAs have recently gained prominence for their roles in transcriptional regulation. They range in size from 21 nucleotides to greater than 10,000 bases and regulate a variety of processes including transcriptional regulation, chromosome replication, RNA processing and protein degradation. The most reliable way to identify a putative ncRNA is to look across species for conservation of mRNA sequence without conservation of predicted protein sequence. Therefore, the complete cDNA sequence can be compared carefully to mouse sequence to look for conserved amino acid sequence within open reading frames. In the event that there is no conserved ORF the possibility of a non-coding RNA gene can be investigated by isolating polysomes on a sucrose density gradient and determining whether FOE is in the polysomal fraction by quantitative RT-PCR. Tubulin mRNA and an ncRNA such as H1 can be used as a control for the various fractions.

CD34+ isolation and culture. CD34+ cells can be isolated using the Miltenyi MidiMacs CD34+ Direct Progenitor Isolation Kit. Culture can be in RPMI plus glutamine, 10% FCS, Penicillin/Streptomycin and 5 ng/ml IL-5 at 37° C. in 5% $CO_2$.

cDNA library construction and Sequencing. Due to the difficulty in obtaining CD34+cells, a cDNA library can be constructed from PCR amplified cDNA obtained from CD34+cord blood cultured with 5 ng/ml of L-5 for 24 hours. The library can be constructed using the Creator SMART cDNA Library Construction Kit (BD Biosciences), a kit designed for low starting amounts of RNA. The library can be transformed into competent XL-1 Blue (Stratagene). Clones can be selected from plated libraries lifted onto Hybond nylon membranes by hybridization (conditions) to a small a 32p labeled probe cloned from a PCR fragment of FOE. Labeling can be done using Stratagene's random priming IT kit. cDNA clones can be verified as full length by comparing the size of the cDNA to the size of the transcript on a northern blot. Probes can be chosen from predicted 5' regions of the mRNA based on northern blot results and Genbank sequence. DNA can be isolated from positive clones and both strands can be sequenced at the University of Utah Sequencing Core Facility. Open reading frames can be identified by ORFinder and sequences can be aligned to genomic DNA using the NCBI program, Spidey. The NCBI programs, Protein Blast, CD-Search, COGnitor and CDART can be used to search for protein classes and motifs.

Antibody production and Western blot. Polyclonal antibodies from rabbits can be raised to KLH conjugated peptides derived from putative FOE protein using the service provided by Cocalico Biologicals. RIBI adjuvant can be used to stimulate antibody production. Rabbits can be bled before and after inoculation and boosted twice per month. Antibody production can be verified by western blot against the expressed recombinant protein and protein derived from IL-5 stimulated cord blood cells. The cDNA clone can be cloned into Creator System (BD Biosciences) inducible bacterial expression vectors (pLP-Protet-6xHN) by Cre-Lox recombination and expressed in *E. coli*. The Invitrogen Rabbit Western Breeze kit can be used with nitrocellulose membranes for western blotting.

Sucrose gradients. A 10-50% sucrose gradient can be layered with a gradient maker. IL-5 stimulated CD34+cells can be lysed with Nonidet P-40 (0.5%) and sodium deoxycholate (0.25%). Cytoplasmic and nuclear RNA fractions can be separated by centrifugation for 5 minutes at 800 g and cytoplasmic RNA can be layered on the sucrose gradient. The gradient can be spun for 4 hours at 124,000 g in an ultracentrifuge. Fractions can be collected, RNA can be isolated and RT-PCR of FOE can be performed on the various fractions. α-tubulin and H1 RNA can be used as controls for cell number and polysomal fraction (α-tubulin) and ncRNA fractions

3. Example 3

EGO (FOE) Expression is Specific to IL-5 Induced Eosinophil Progenitor Development FOE can be expressed only during IL-5 stimulated eosinophilopoiesis or also during IL-3 or GM-CSF stimulated eosinophil development. FOE can also be expressed in other hematopoeitic cell types, such as developing neutrophils or monocytes. Eosinophil specific gene expression can be investigated by comparative RT-PCR of the FOE mRNA derived from CD34+ cord blood cultures grown with cytokine combinations that enhance growth of various lineages. Furthermore, eosinophil specific expression of FOE can be studied by immunohistochemical staining patterns of FOE relative to the eosinophil granule protein, EPO.

FOE transcript and protein expression patterns can be determined via Northern blot and western blot in various tissue types. Commercial Northern blots are available that include major human organ systems such as brain, heart, skeletal muscle, spleen, etc. Available immune system blots include spleen, lymph node, thymus, PBL, bone marrow and fetal liver. These experiments can give us an overview of the constitutive expression of FOE protein and mRNA.

FOE mRNA expression during eosinophilopoiesis occurs between 6-24 hours. The time course of FOE protein expression can also be monitored by western blot in IL-5 stimulated CD34+ cord blood cells. To simulate what occurs in the bone marrow, northern blot can be done on RNA obtained from IL-5 stimulated CD34+ cells obtained from apheresis of peripheral blood. Western blot can also be done on CD34+ cells obtained from apheresis and cultured in the presence of IL-5.

FOE can be expressed only during IL-5 stimulated eosinophilopoiesis or also during IL-3 or GM-CSF stimulated eosinophil development. The specificity of cytokine stimulation to FOE induction can be addressed by growing eosinophils from CD34+ cord blood cells stimulated with GM-CSF, IL-3 or IL-5 and measuring FOE mRNA expression by real time quantitative RTPCR. It is possible that IL-3 or GM-CSF can induce autocrine IL-5 production which can in turn induce FOE transcription. Eosinophils can be produced in the absence of interleukin-5; if autocrine IL-5 production is occurring, anti-IL-5 antibodies can be added to the culture. Therefore, the specificity of FOE induction during non-IL-5 induced eosinophilopoeisis can be assessed.

The specificity of FOE induction to eosinophil development can be analyzed by growing several myeloid types (i.e. eosinophils, neutrophils and monocytes) from CD34+ cord blood cells and assaying for FOE mRNA expression at various timepoints in development. Due to the rapid time frame of FOE expression (6 hours) and eosinophil development (1-3 weeks) it is likely that FOE is expressed by committed hematopoietic progenitors rather than by pluripotent hematopoietic stem cells. It has been shown that expression does not occur in developing erythrocytes derived from erythropoietin stimulated CD34+ cord blood cells. Contamination of other myeloid lineages by eosinophils may occur at low levels; therefore percentages of cell types can be assessed by flow cytometry. The level of FOE stimulation can be proportional to the level of eosinophils.

Northern and western blot. Northern blots (Human 12 lane MTN Blot, MTN blot II, III and Human Immune System MTN blot II) can be purchased from BD Biosciences Clontech and used according to the manufacturer's directions. Multiple 16 tissue prefabricated western blot may be purchased from Biocat (Germany). PBL and bone marrow protein can be electrophoresed and electroblotted separately as these tissue proteins are not available commercially.

CD34+ cell culture. CD34+ cells can be isolated as above. Apheresis of mobilized peripheral blood cells can be done by the CRC (Clinical Research Center) and cells can be isolated and cultured identically to cord blood. All cells can be grown in RPMI with glutamine, 10% FCS, and Penicillin/Streptomycin. CD34+ cells can be stimulated with the following cytokines: eosinophils, 5 ng/ml IL-5; mast cells, 50 ng/ml SCF; monocytes;, 20 ng/ml GM-CSF, 50 ng/ml M-CSF; neutrophils, 20 ng/ ml GM-CSF, 50 ng/ml G-CSF (or 10 ng/ml SCF and 50 ng/ml GCSF)(54). Cells can be harvested and RNA isolated at the following timepoints: 0 hours, 6 hours, 24 hours, 72 hours and one week. Anti-IL-5 antibodies, (Research Diagnostics, Flanders N.J.) if necessary, can be added to IL-3, GM-CSF cultures at 5 ng/ml or more.

Flow cytometry: Flow cytometry can be performed on a Becton Dickinson FACSCAN in our core laboratory. Cells can be blocked with 10% human serum and stained with the following primary antibodies:monocytes; CD 14, mast cells; CD54 or mast cell tryptase, neutrophils; CD 15 and eosinophils; IL-5Ra. Secondary antibodies can be anti-mouse FITC or PE.

Real time RT-PCR. Total RNA can be isolated using the Qiagen Rneasy kit. First strand cDNA can be synthesized using the Endofree RT kit (Ambion) or Superscript II Invitrogen). PCR can be done in triplicate using the following conditions: 2 mM dNTPs, 0.5uM primers, 1/30,000 Sybr Green I (Molecular Probes), 0.5 UAmplitaq(ABI), 0.1 ug Taqstart antibody (Clontech), 4 mM Idaho Technology PCR buffer and 4 ul 5-1 O× diluted cDNA in a 20 ul reaction. Cycling parameters are 94° C. for 0 seconds, 60° C. for 20 seconds, 40 cycles. All reactions are normalized to an α-tubulin control. Efficiency of the α-tubulin primers is 2.0 and efficiency of all other primers is assumed to be 2.0. Crossing point is based on $2^{nd}$ derivative maximum using LightCycler Data Analysis v3.5. Fold change is calculated as described (50).

Immunohistochemistry. Cultured cells can be prepared by cytospin. Cytospin preparations can be fixed in formalin acetone for 30 s and stained for 10 min in phosphate buffer containing 75 mg 3.3 diaminobenzidine tetrahydrochloride, 0.3 ml 3% H202 and 39.2 mg NaCN to stain for endogenous EPO(55). This method differentiates eosinophil peroxidase from neutrophil peroxidase. For the second label, FOE antibody can be applied to the slides and biotinylated goat anti-rabbit antibody can be allowed to bind to FOE. Detection can be with avidin-horseradish peroxidase (Vector Laboratories ABC kit).

In situ hybridization: Oligonucleotides complimentary to FOE mRNA can be labeled with FITC, hybridized and washed. Goat anti-fluorescein antibody can be applied and detection can be with rabbit anti-goat fluorescein. Oligonucleotides complimentary to C/EBPεmRNA can be labeled with biotin. Detection can be with streptavidin Texas Red.

4. Example 4

The Function of FOE in eosinophilopoeisis with Respect to Differentiation and Commitment Silencing of FOE mRNA expression inhibits synthesis of MBP transcripts. To determine if this is a specific inhibition or if FOE also inhibits EDN, ECP or EPO transcription, real time quantitative PCR can be performed on FOE silenced cells using primers specific to these granule protein transcripts. Furthermore, the effect of FOE silencing on the transcription factors C/EBPε, C/EBPα and GATA-1 can also be investigated by the same method. If FOE has an effect on C/EBPε synthesis, then it is likely that MBP transcripts are inhibited secondary to C/EBPε. The sequence of FOE in the cascade of gene expression leading to eosinophil development can be approximated by determining which genes FOE inhibits.

The effect of FOE silencing on the morphological development of IL-5 stimulated CD34+ cord blood cells can be determined by light and electron microscopy. Typically, metamyelocyte morphology consisting of developing granules and a partially bilobed nucleus are present at one week of culture. It is likely that the lack of MBP and possibly other proteins in silenced cells could contribute to morphological changes in the granules.

FOE is expressed quite early in IL-5 driven eosinophil development. FOE transcripts are present 6 hours after IL-5 stimulation, prior to the expression of C/EBPε mRNA at 24 hours and much earlier than granule protein mRNA expression at 72 hours or beyond. This suggests the possibility that FOE is important in commitment to the eosinophil lineage. Forced expression of GATA-1, an early myeloid transcription factor, is able to drive transduced CD34+ stem cell development into eosinophils in the absence of IL-3, IL-5 and GM-CSF. In addition, enforced expression of C/EBPα in myeloid progenitor cells causes development of both eosinophils and neutrophils. The forced expression of FOE in CD34+ cells can also be assessed to measure the effect of FOE on eosinophil commitment.

RNA silencing. Plasmid DNA (1.0 ug) can be electroporated in duplicate into 5-8×10⁵ CD34+ cells using the CD34+ Nucleofector kit and a Nucleofector device (Amaxa) set on program U8. Cells can be put in one well each of a 24 well plate and RPMI, 10% FCS/Gln can be immediately added. After 18 hours 1 ng/ml IL-5 can be added (time=0') and RNA can be isolated at 6 hours and 72 hours using a Qiagen Rneasy.

Real time RT-PCR. Real time RT-PCR. Total RNA can be isolated using the Qiagen Rneasy kit. First strand cDNA can be synthesized using the Endofree RT kit (Ambion) or Superscript II (Invitrogen). PCR can be done in triplicate using the following conditions: 2 mM dNTPs, 0.5 uM primers, 1/30,000 Sybr Green I (Molecular Probes), 0.5 UAmplitaq(ABI), 0.1 ug Taqstart antibody (Clontech), 4 mM Idaho Technology PCR buffer and 4 ul 5-1 O× diluted cDNA in a 20 ul reaction. Cycling parameters are 94° C. for 0 seconds, 60° C. for 20 seconds, 40 cycles. All reactions are normalized to an α-tubulin control. Efficiency of the α-tubulin primers is 2.0 and efficiency of all other primers is assumed to be 2.0. Crossing point is based on $2^{nd}$ derivative maximum using LightCycler Data Analysis v3.5. Fold change is calculated as described.

Microscopy. Developing cells can be cytospun and stained with Fisher Protocol Hema3 (similar to Wright Giemsa) and visualized on a Zeiss Axiophot imaging system. Electron microscopy can be performed in the University of Utah Core Facility using antibody labeled gold particles corresponding to FOE protein and EPO.

Enforced expression of FOE. FOE can be cloned into an inducible, selectable, eukaryotic expression vector such as Invitrogen's GeneSwitch System pGene V5/His. CD34+ cells can be prestimulated with 50 ng/ml SCF, thrombopoeitin, Flt-3 ligand and IL-6. Plasmids (1.0 ug) can be electroporated into CD34+ cells using a CD34+ Nucleofector kit and a Nucleofector device (Amaxa) set on program U8. Cells can be put in one well each of a 24 well plate and RPMI, 10% FCS/Gln can be immediately added. Erythropoeitin, 2 units/ml (or another cytokine that doesn't normally induce FOE expression) can be added to the culture at 18 hours post electroporation. RNA can be isolated at various timepoints and expression of granule protein transcripts can be monitored by real time quantitative RT-PCR.

5. Example 5

A Cell Based Screening Assay for Identifying Inhibitors of Eosinophil Proliferation The purpose of this study was to identify potential drug candidates for asthma. Eosinophils are white blood cells which contribute to the pathology of asthma. Lidocaine inhibits interleukin-5 (IL-5) mediated survival and activation of human eosinophils and is able to replace inhaled glucocorticoids for the treatment of asthma; however, lidocaine has many undesired side effects. Consequently, a collection of compounds, including commercially available lidocaine analogs and synthesized compounds designed by modification of lidocaine structure, were investigated for inhibitory activity on the proliferation of TF-1 cells, a CD34$^+$ cytokine dependent erythroleukemic cell line model for eosinophil development. TF-1 cell proliferation assays were performed at various concentrations of lidocaine and the investigated compounds to determine fifty percent growth inhibition values (IC-50). Among 75 investigated compounds, 25 revealed more potent cell growth inhibitory activity, with IC-50 ranging from 1-136 µM, than lidocaine (IC-50 147 µM). The investigated compounds were also tested on TF-1 cells stimulated with epoietin-α (EPO) as a model for cell type specificity. IC-50 values that are lower on cells grown in IL-5 compared to EPO suggest drug specificity for inhibiting IL-5 mediated proliferation. Seven of the top 25 compounds were slightly more specific than lidocaine in the assay. Consequently, the cell based assay is an effective method for screening chemical compounds and has revealed potential drug candidates for the treatment of asthma.

Asthma is a chronic inflammatory condition, triggered by environmental factors in genetically predisposed individuals [Siqueira, 2005], and is characterized by mast cell, T lymphocyte, and eosinophil infiltrates in the bronchial mucosa [Roquet, 1997]. Eosinophils are end stage, terminally differentiated leukocytes that reside in the submucosal tissue of the gastrointestinal tract. They are recruited to sites of specific immune reactions, especially during allergic diseases, [Kita, 2003] and are correlated with disease severity [Roquet, 1997]. Activated eosinophils secrete major basic protein which can lead to bronchial hyperactivity, damage to the bronchial mucosa, and stimulate the production of profibrotic cytokines [Kita, 2003] [Pergorier, 2006].

Eosinophils are not only associated with asthma, but that they also cause the disease has been tested. Eosinophil activation and prevention of apoptosis has been linked to the cytokine, IL-5 [Kita, 2003] [Simon, 2006]. Anti- IL-5 therapy has been investigated in several studies in humans to deplete eosinophils. Administration of the anti-IL-5 drug, mepolizumab, to patients with mild asthma reduced blood and sputum eosinophils [Leckie, 2000]; however, eosinophils were still present in bone marrow and lung tissue[Flood-Page] The use of anti-IL5 did not improve the symptoms in these asthmatics, but the patients showed decreased airway remodeling. Two mouse models have been developed that are devoid of eosinophils [Lee, 2004] [Humbles, 2004] and have reduced asthma severity in standard asthma models. The mice are healthy and do not require living in sterile conditions suggesting that eosinophils are not required in laboratory conditions. Accordingly, by selectively blocking the overproduction of eosinophils, novel drugs can act as therapeutic treatments for asthma.

Inhaled glucocortocoids have been established as the standard for the treatment of asthma [Cockcroft, 1999], although they are accompanied numerous adverse effects, such as hypothalamic-pituitary-adrenal axis suppression, reduction of bone mineral density and vertical growth, and ocular toxicity [Rizzo, 2006]. Therefore a need exists for alternative treatments to overcome these undesirable side effects of steroid therapy for asthma and to provide another effective agent for the treatment of eosinophil-associated asthma.

The topical anesthetic lidocaine inhibits eosinophil survival and can replace inhaled glucocorticoid steroid treatments in asthmatics. In the first study on the effect of nebulized lidocaine, 17 out of 20 prednisolone-dependent patients were able to eliminate or significantly reduce steroid usage [Hunt, 1996]. A second study was performed with children who were able to stop systemic glucocorticoid use after treatment with nebulized lidocaine [Decco, 1998]. Finally, a randomized, double blind, placebo controlled study, including 50 patients with mild to moderate asthma symptoms, was conducted. In this study, nebulized lidocaine treated patients were able to discontinue their use of inhaled glucocorticoids. Furthermore, blood eosinophil levels decreased in these patients. As expected, the symptoms in patients in the placebo group worsened and eosinophils increased [Hunt, 2004]. The results of these studies indicate that nebulized lidocaine is an effective treatment for asthma while also supporting the hypothesis that the beneficial effects of lidocaine are due to a decrease in eosinophils. This study describes a screening method to identify new drug candidates with the potential to treat asthma by decreasing eosinophil levels.

a) Materials and Methods (1) Cell Line and Culture

TF-1 cells were cultured in RPMI 1640 media (Invitrogen, Carlsbad, Calif.) with 10% FCS (Hyclone, Logan, Utah), Gln (Invitrogen, Carlsbad, Calif.), penicillin streptomycin (Invitrogen, Carlsbad, Calif.), and either the cytokine IL-5 (5 ng/mL) (Invitrogen, Carlsbad, Calif.) or Procrit Epoeitin-α (EPO) (2 units/mL) (Ortho Biotech, Bridgewater, N.J.).

(a) Chemicals

Lidocaine, its analogs and the reference drugs (controls) dexamethasone and ketotifen fumarate (Zaditor®) were obtained commercially. Modified lidocaine derivatives were synthesized from the reaction of appropriate acid chloride or anhydride with 2,6-dimethylaniline in dichloromethane for 4 hours at room temperature. The synthesized products were purified by flash chromatography and crystallized from ethanol. Their structure were confirmed by spectroscopic (IR, NMR and Ms) and elemental methods of analysis.

(b) Method

Controls and test compounds were assayed in serial dilutions, ranging from 1 mM to 0.5 uM, against TF-1 cell proliferation. Compounds were solublized in DMSO in 0.2M solutions followed by serial dilutions with the culture media. This resulted in a 0.5% final DMSO concentration in RPMI, 10% FBS, Gln, and P/S.

Each dilution of the compounds was tested in triplicate in a 96 well, flat bottom tissue culture plate with 10,000 TF-1 cells per well for their abilities to inhibit IL-5 and/or EPO stimulated cultures. Wells without cells were used for the background signals. Both IL-5 and EPO stimulated cell cultures were tested in assays performed on the same day. Cultures were incubated for 72 hours in a 37° C. humidified incubator. At the end of the incubation, CellTiter $AQ_{ueous}$ One Solution (Promega, Madison, Wis.) was added for 1 to 3 hours, depending on the rate of color change. Following sufficient color change, the plates were read on a spectrophotometer (SpectraMax 190, Molecular Devices) at 490 nm.

(c) Data Analysis

IC-50 and $I^2$ values were calculated using the software SOFTmax Pro (Molecular Devices, Sunnyvale, Calif.).

b) Results and Discussion

To identify lidocaine analogs and other small molecule compounds that have potential for asthma treatment, cell based assays were used. A cell based assay is an effective way to screen for drugs candidates because the mechanism of action for lidocaine is not known and drugs that are not cell permeable are eliminated immediately. Because eosinophils are difficult to culture, TF-1 cells, a cytokine dependent, erythroleukemic derived CD34+ cell line [Kitamura, 1989], were used as a cell line model for eosinophil development. This assay was used to identify drug candidates for asthma that are more potent and specific than lidocaine.

Compounds were screened by inspecting the IC-50 values of the drug candidate on the proliferation assay. All IC-50 values with $r^2 \geq 0.75$ were repeated, while lower $r^2$ values indicate a flat line or no response to a drug (FIG. 13). Potencies of the investigated compounds in inhibiting TF-1 cell proliferation were evaluated by comparing their IC-50 values relative to lidocaine. Due to the ability of TF-1 cells to be stimulated by a variety of cytokines, specificity can be evaluated by comparing IL-5 and EPO stimulated cell cultures IC-50 values. Specificity or differential inhibition (Di) values can be calculated for the investigated compounds using equation 1.

$$Di = EPO\ IC\text{-}50/IL5\ IC\text{-}50 \qquad \text{(equation 1)}$$

Applying the above equation allows the comparison of specificity of the tested compounds relative to the lead compound lidocaine.

To validate the utility of this assay, ketotifen fumarate (3), dexamethasone (2), and lidocaine (1) were assayed as positive controls because of the known anti-eosinophil activities of these drugs. Ketotifen fumarate, is a non-competitive histamine antagonist established for use against allergic conjunctivitis. Eosinophil necrosis and decreased chemotaxis has been observed with the use of this drug [Hasela,2005] [Woerly,2003]. Dexamethasone is a glucocorticoid which inhibits eosinophil survival and chemotaxis[Usami, 2006]. The IL-5 IC-50 values for ketotifen fumarate and dexamethasone, 9 uM and 4 uM respectively, treated cells were substantially less than lidocaine (140 uM), showing that our assay can identify compounds which are known inhibitors of eosinophil proliferation or chemotaxis (Table 5, Table 6. The Di value for dexamethasone, 5.136, shows specific inhibition of IL-5 stimulated cells and suggests that this assay is a useful in vitro model for inhibition of eosinophil proliferation (Table 7).

Seventy five compounds were tested in the TF-1 cell proliferation assay. Sixty nine of the tested compounds were obtained commercially as analogs of lidocaine or related small molecules; some of them are well known local anesthetics. Six compounds were synthesized as novel lidocaine analogs. Twenty five compounds had IL-5 IC-50 values lower than lidocaine's (Table 5, Table 6); In particular, 4-Amino-N-pyridin-3-yl-methyl-benzamide (4) consistently had the lowest IC-50 tested of 1.3 uM. N-(2,4-difluorophenyl)-2-(-4-pyrimidin-2-ylpiperazinyl)ethanamide (5) also has a relatively low IC-50 value of 5 uM. Seven of the top 25 compounds were only slightly more specific to IL-5 stimulated TF-1 cells compared to EPO stimulated cells (Table 7), however the dexamethasone control, which selectively decreases blood eosinophil levels in vivo was specific in our assay (Di of 5.14). This shows that the assay is valid for identifying specific compounds, although none of our tested compounds was particularly specific.

As a local anesthetic, lidocaine's activity is due to its sodium channel blocking ability. Commonly, anesthetics have tertiary amines connected through an amide or ester linkage to an aromatic structure. The length of the alkyl linkage has been shown to increase the hydrophobicity which increases the anesthetic property of the molecule [Bokesh, 1986]. The aromatic moiety and the tertiary amine have shown to be contributors to the sodium channel blocking ability in local anesthetics [Haeseler, 2002] [Wagner, 1999] [Rolf, 2000]. More potent sodium channel blockers, such as dyclonine, are not effective against asthma [Groben, 2001]; therefore, it is unlikely that the sodium channel blocking activity of lidocaine is its mechanism for IL-5 inhibition and against asthma. Additionally, the potency of sodium channel blockage is not related to the effect of lidocaine analogs on eosinophil apoptosis or inflammatory allergic response in the rat lung [Okada, 1998] [da Costa, 2007]. Accordingly, modified lidocaine analogs based on removal of the structural moieties responsible for the sodium channel blocking ability of lidocaine were synthesized to identify the pharmcophoric moiety responsible for inhibition of IL-5 stimulated TF-1 cells.

Six novel modified lidocaine derivatives were synthesized and tested. It is worthy to mention that five (9, 15, 18, 22 and 26) of the six synthesized modified lidocaine derivatives were among the top 25 compounds revealed IL-5 IC-50 values lower than lidocaine's (Table 6). All of the synthesized lidocaine derivatives, except the quinoline-4-carboxamide derivative (9) are lacking the tertiary amine, indicating that it is not necessary for function in this assay.

c) Conclusion

Lidocaine is a useful drug for the treatment of asthma because of its ability to reduce the number of eosinophils in the blood. Unfortunately, it is accompanied by many side effects when used either systemically or topically. By using a TF-1 cell based assay, new compounds can be found to inhibit the systemic eosinophil population more effectively and safely than lidocaine.

TABLE 5

Structures of the reference drugs (1-3) and the top 25 most potent compounds (4-28) arranged in a descending manner according to their IL-5 IC-50. Compounds 9, 15, 18, 22, and 26 are novel synthesized molecules.

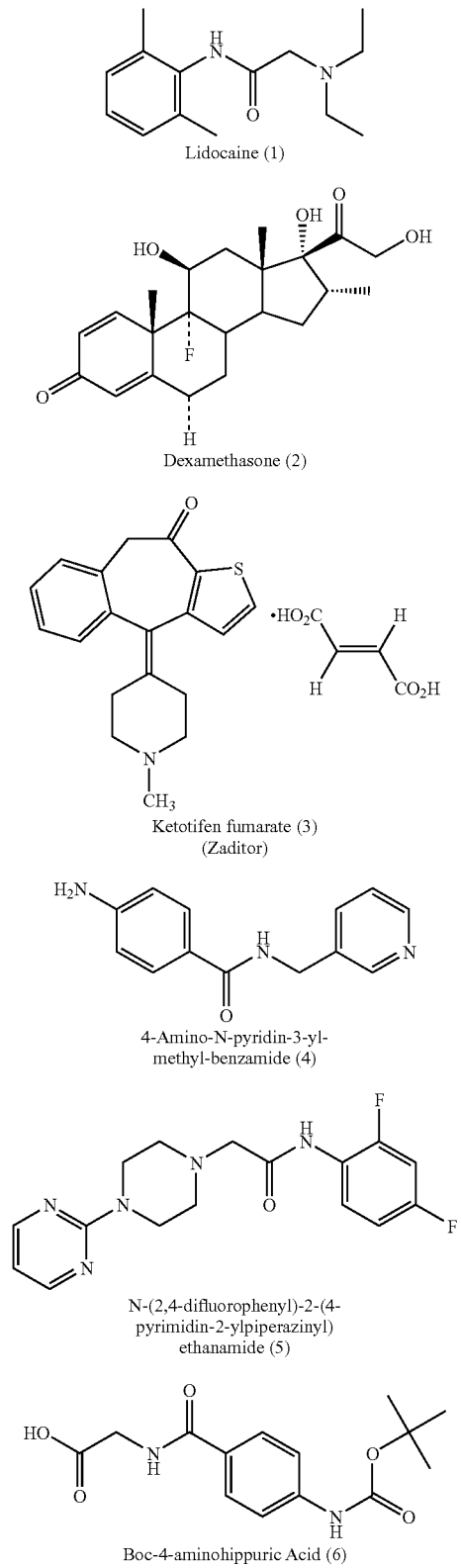

TABLE 5-continued

Structures of the reference drugs (1-3) and the top 25 most potent compounds (4-28) arranged in a descending manner according to their IL-5 IC-50. Compounds 9, 15, 18, 22, and 26 are novel synthesized molecules.

9,10-Difluoro-2,3-dihydro-3-methyl-7-oxo-7H-pyrido[1,2,3-DE]-1,4-benzoxazine-6-carboxylic acid (7)

7-Bromo-4-methyl-3,4-dihydro-2H-1,4-benzoxazine (8)

N-(2,6-dimethylphenyl)quinoline-4-carboxamide (9)

3-Carboxymethoxy-1,2,3,4-Tetrahydroisoquinol (10)

N-Benzoyl-L-Threonine (11)

3,4-Dihydro-2H-1,4-Benzoxazine-2-Carboxylic Acid (12)

Dibucaine Hydrochloride (13)

Tocainide HCL (14)

N-(2,6-dimethylphenyl)hexanamide (15)

3,4-Ethylenedioxyaniline (16)

Procaine (17)

N-(2,6-dimethylphenyl)pivalamide (18)

Lidocaine HCL (19)

2-methyl-N-(3-pyridinylmethyl)benzamide (20)

4-methyl-3,4-dihydro 2H-1,4-benoxazine 7 carboxylic acid (21)

TABLE 5-continued

Structures of the reference drugs (1-3) and the top 25 most potent compounds (4-28) arranged in a descending manner according to their IL-5 IC-50. Compounds 9, 15, 18, 22, and 26 are novel synthesized molecules.

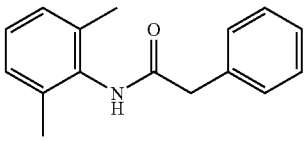 [SMILES: Cc1cccc(C)c1NC(=O)Cc1ccccc1]

N-(2,6-dimethylphenyl)-2-phenylacetamide (22)

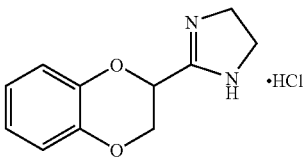 [SMILES: c1ccc2c(c1)OCC(C1=NCCN1)O2 ; Cl]

Idazoxan Hydrochloride (23)

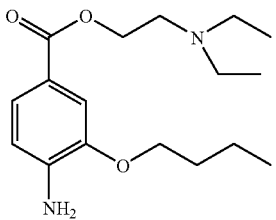 [SMILES: CCCCOc1cc(C(=O)OCCN(CC)CC)ccc1N]

Benoxinate (24)

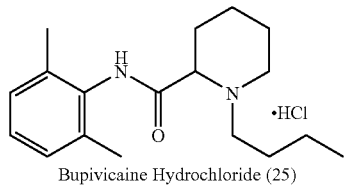

Bupivicaine Hydrochloride (25)

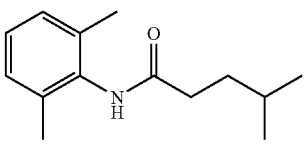 [SMILES: Cc1cccc(C)c1NC(=O)CCC(C)C]

4-methyl-N-(2,6-dimethylphenyl)-pentanamide (26)

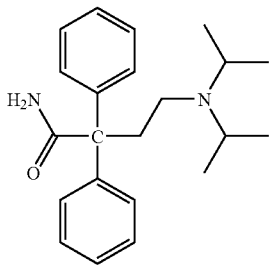 [SMILES: CC(C)N(CCC(C(N)=O)(c1ccccc1)c1ccccc1)C(C)C]

Disopyramide (27)

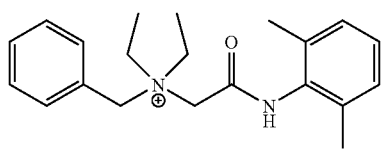 [SMILES: CC[N+](CC)(CC(=O)Nc1c(C)cccc1C)Cc1ccccc1]

Denatonium Saccharide (28)

TABLE 6

IC50 of the 25 most potent compounds. Reference compounds are 1-3. Compounds 4-28 are shown in descending order according to IC-50.

| Compound | Compound No. | IL-5 IC-50 (uM) |
|---|---|---|
| Lidocaine | 1 | 147 |
| Dexamethasone | 2 | 9 |
| Ketotifen fumarate (Zaditor) | 3 | 9 |
| 4-Amino-N-pyridin-3-yl-methyl benzamide | 4 | 1.3 |
| N-(2,4-difluorophenyl)-2-(4-pyrimidin-2-ylpiperazinyl) ethanamide | 5 | 5 |
| Boc-4-aminohippuric Acid | 6 | 19 |
| 9,10-Difluoro-2,3-dihydro-3-methyl-7-oxo-7H-pyrido[1,2,3-DE]-1,4-benzoxazine-6-carboxylic acid | 7 | 20 |
| 7-Bromo-4-methyl-3,4-dihydro-2H-1,4-benzoxazine | 8 | 24 |
| N-(2,6-dimethylphenyl)quinoline-4-carboxamide | 9 | 24 |
| 3-Carboxymethoxy-1,2,3,4-Tetrahydroisoquinol | 10 | 26 |
| N-Benzoyl-L-Threonine | 11 | 30 |
| 3,4-Dihydro-2H-1,4-Benzoxazine-2-Carboxylic Acid | 12 | 38 |
| Dibucaine Hydrochloride | 13 | 48 |
| Tocainide Hydrochloride | 14 | 49 |
| N-(2,6-dimethylphenyl)hexanamide | 15 | 62 |
| 3,4-Ethylenedioxyaniline | 16 | 69 |
| Procaine | 17 | 71 |
| N-(2,6-dimethylphenyl)pivalamide | 18 | 79 |
| Lidocaine Hydrochloride | 19 | 84 |
| 2-methyl-N-(3-pyridinylmethyl)benzamide | 20 | 90 |
| 4-methyl-3,4-dihydro 2H-1,4-benoxazine 7 carboxylic acid | 21 | 92 |
| N-(2,6-dimethylphenyl)-2-phenylacetamide | 22 | 96 |
| Idazoxan Hydrochloride | 23 | 97 |
| Benoxinate | 24 | 98 |
| Bupivicaine Hydrochloride | 25 | 107 |
| 4-methyl-N-(2,6-dimethylphenyl)-pentanamide | 26 | 119 |
| Disopyramide | 27 | 129 |
| Denatonium Saccharide | 28 | 136 |

TABLE 7

Di and IC-50 values of the control drugs and the most potent compounds with higher Di[a] compared to lidocaine. Reference compounds 1-3 are shown at the top of the table and the remaining compounds are in order of specificity.

| Compound | Compound No. | Di | IL-5 IC-50 (uM) | EPO IC-50 (uM) |
|---|---|---|---|---|
| Lidocaine | 1 | 1.361 | 147 | 200 |
| Dexamethasone | 2 | 5.136 | 7 | 38 |
| Ketotifen fumarate (Zaditor) | 3 | 1.000 | 9 | 9 |
| Lidocaine Hydrochloride | 21 | 3.286 | 84 | 276 |
| N-(2,6-dimethylphenyl)hexanamide | 17 | 2.210 | 62 | 137 |
| 3,4-Ethylenedioxyaniline | 20 | 1.971 | 69 | 136 |
| 2-methyl-N-(3-pyridinylmethyl)benzamide | 16 | 1.700 | 90 | 153 |
| Procaine | 4 | 1.535 | 71 | 109 |
| 4-Amino-N-pyridin-3-yl-methyl-benzamide | 15 | 1.471 | 1.3 | 1.9 |
| 4-methyl-3,4-dihydro 2H-1,4-benoxazine 7 carboxylic acid | 19 | 1.412 | 91.8 | 130 |
| N-(2,6-dimethylphenyl)-2-phenylacetamide | 22[b] | 1.351 | 95.5 | 129 |

[a]Di was determined using equation 1.
[b]Di value is lower than Lidocaine (1) but almost comparable

6. Example 6

EGO, a Novel, Non-coding RNA gene, Regulates Eosinophil Granule Protein Transcript Expression

Eosinophils are tissue dwelling hematopoietic cells that likely play a role in parasitic immunity and allergic disease, such as asthma (Kita 2003). Activated eosinophils secrete toxic basic proteins such as MBP and are postulated to cause bronchial hyperreactivity, damage of the bronchial mucosa, and remodeling of the airways (Kita 2003). Mice lacking eosinophils fail to show hallmarks of asthma such as airway hyperresponsiveness, tissue remodeling, and mucous metaplasia (Lee 2004; Humbles 2004).

Eosinophils develop in the bone marrow from hematopoietic stem cells and migrate mainly to the gut or to sites of inflammation. Eosinophils, neutrophils, and monocytes have a common progenitor in the myeloid pathway of development. The combinatorial interactions of several transcription factors, including GATA-1, PU.1, and the CCAAT enhancer binding proteins, c/EBPa and E, are important to eosinopbil development (McNagny 2002; Nerlov 1998; Hirasawa 2002; Zhang 1997). High levels of PU.1 specify myeloid differentiation by antagonizing GATA-1 in the earliest stages of stem cell commitment (Nerlov 1988). In particular, a high affinity GATA-1 binding site within the GATA-1 promoter appears to be critical for eosinophil development; deletion of this binding site in mice specifically abolishes the entire eosinophil lineage (Okazaki 2002). During later stages of eosinophil development, an intermediate level of GATA-1 in synergy with PU.1 directs the formation of the eosinophil lineage by activating dual binding sites in the MBP promoter (Du 2002; Gombart 2003; Yamaguchi 1998). GATA-1 also activates the eotaxin receptor CC chemokine receptor-3 (CCR3) promoter and the IL-5 receptor a (IL-5Ra) gene (Zimmermann 2005). The CCAAT enhancer binding protein, c/EBPa, is important in early myeloid development, whereas c/EBPE plays a later role (Yamanaka 1997). Mouse knockouts of c/EBPE affect both neutrophil and eosinophils development at the myelocyte to metamyelocyte stage (Yamanaka 1997). Other genes involved in eosinophil development include the helix-loop-helix transcription factors, Id 1 and 2, and FOG (Friend of GATA). FOG inhibits eosinophil development by interaction with GATA-1 (Querfurth 2000). Id 1 inhibits eosinophil development whereas Id 2 enhances both neutrophil and eosinophil development (Buitenhuis 2005). All of these transcription factors are used in general myeloid development; therefore, eosinophil development is regulated by fine tuning of combinatorial expression levels of transcription factors.

This complex interplay of transcription factors is influenced by the cytokines IL-3, GM-CSF and particularly the Th2 cytokine, IL-5. CD34+ hematopoietic cells cultured in IL-5 are exclusively eosinophils after several weeks of culture (Ema 1990). Furthermore, transgenic mice over-expressing IL-5 have massive eosinophilia (Lee 1997; Dent 1990; Tominaga 1991). However, mouse IL-5 knockouts still have basal levels of eosinophils but do not develop eosinophilia when infected by helminths or challenged with aeroallergen (Kopf 1996; Foster 1996). Inhalation of IL-5 in human asthmatics causes increased eosinophil numbers and airway hyperreactivity (Kitagaki 1997; Shi 1998). Furthermore, a subset of mouse bone marrow cells expressing IL-5Rα are eosinophil progenitors (Iwasaki 2005). Therefore, IL-5 is the most important cytokine in eosinophil development but alternative developmental pathways also exist.

In this study it was shown that EGO is a novel, nested, ncRNA, gene expressed during eosinophil development and in mature eosinophils. NcRNA accounts for at least half of transcribed genes in mammals and has been increasingly implicated in playing a functional role in biology (Claverie 2005; Carninci 2005; Ravasi 2006; Willingham 2005) NcRNAs are often found nested in the introns or in 3' untranslated regions of coding genes. It is herein shown that EGO is an ncRNA involved in regulating MBP and EDN transcript expression.

a) Methods (1) Cell Isolation and Culture

Bone marrow was obtained by informed consent from normal volunteers after permission from the University of Utah IRB. CD34+ cells were enriched to 60-80% purity from mononuclear cord blood or bone marrow mononuclear cells using the Midi Macs System (Miltenyi) and the CD34+ Human Selection kit (StemSep). Eosinophils were isolated from peripheral blood granulocytes using negative selection with CD1 6 (Miltenyi). Cells were cultured in RPMI with penicillin/streptomycin (P/S), 10% FCS (Hyclone) and 5 ng/ml IL-5 (R&D Systems) or frozen in 10% DMSO for later use. Cells were cultured $0.5 \times 10^6$ per well in a 48 well flat bottom plate. CD34+ cells were stimulated with the following cytokines: 2 µl/ml epoietin-α, 50 ng/ml SCF, 20 ng/ml GM-CSF, 50 ng/ml M-CSF, 20 ng/ml GM-CSF, 50 ng/ml G-CSF or 20 ng/ml IL-3 (R&D Systems). TF-1 cells were grown in RPMI, 10% FCS, P/S and 5 ng/ml IL-5 or 2 µ/ml epoietin-α (Epogen).

Microarray: CD34+ cells were isolated from the umbilical cord blood (UCB) of four placentas (#17, #18, #4 and #23). Samples #17 and #18 were split in half and cultured in IL-5 (5 ng/ml) or epoietin-α (2U/ml). Sample #4 was cultured in IL-5 and sample #23 was cultured in epoietin-α. Samples were not pooled. Following 24 hours of culture, total RNA was isolated and amplified using the Rioamp RNA amplification kit (Arcturus). Labeling and hybridization of amplified antisense RNA to Affymetrix HG-U133A DNA chips was done in triplicate according to the manufacturer's instructions. Data were analyzed using GC-RMA and ranked with non-parametric statistics (Breitling 2005).

Quantitative RT-PCR: Total RNA was isolated using the Qiagen Rneasy kits. First strand cDNA was synthesized using the Superscript III Kit (Invitrogen). PCR conditions were 2 mM dNTPs, 0.5 uM primers, 1/150,000 dilution of Sybr Green (Molecular Probes) I, 0.2 UAmplitaq (Applied Biosystems), 0.1 ug Taqstart antibody (Clontech), 4 mM PCR buffer (Idaho Technology) and 4 ul 10× diluted cDNA in a 20 ul reaction. PCR was done in triplicate on a Roche LightCycler and averages and standard errors were plotted. Second derivative maxima of triplicates are within a half cycle of each other or were repeated. Parameters were 94° C. for 0 seconds, 60° C. for 20 seconds, 40 cycles. All reactions were normalized to an α-tubulin control (Bernard 2002) with the exception of mature eosinophil cDNA which was normalized to a GAPDH control. Efficiency of the αtubulin primers is 2.0 and efficiency of all other primers is assumed to be 2.0. Second derivative maxima were used from LightCycler Data Analysis v3.5 to quantitate RNA levels. Primers for EGO-A are BCOF1 (cttctcctccaggccatacc, SEQ ID NO: 3) and 2223 14F (ccattgtgtagccccg SEQ ID NO: 4). Primers for EGO-B are EGOsp1R2 (ccatcgtgcctgatagaa SEQ ID NO: 5) and BCOF 1. Primers for granule proteins are EDNF2 (caccatggttccaaaact-gttca SEQ ID NO: 6), EDNR2(gttttccatcgccgtt SEQ ID NO: 7), MBPF(gggattgcggtacttataca SEQ ID NO: 8), MBPR (atgggctcagctagtt SEQ ID NO: 9), GAPDHF(tctctgctcctcct-gtt SEQ ID NO: 12) and GAPDHR(caagcttcccgttctca SEQ ID NO: 13). Primers to measure silencing of EGO are 2223 14F8(aggaattatgattgtgggt SEQ ID NO: 10) and BCO39547R3 (ggtatggcctggaggagaag SEQ ID NO: 11). Other primers include GATA-1ex3F (ggactctcctccccag SEQ ID NO: 14) and GATA1ex3R(ctgaattgagggggct SEQ ID NO: 15) and GAPDHF (tctctgctcctcctgtt SEQ ID NO: 12) and GAPDHR (caagcttcccgttctca SEQ ID NO: 13). All amplicons were a single band on agarose gels verified by DNA sequencing.

Northern blot: 0.5-1 µg of Poly A+ RNA (Qiagen Oligotex kit) was electrophoresed on a 1% agarose MOPS formaldehyde gel alongside Millennium Markers (Ambion). Markers were stained in 1×TBE and Sybr Gold (Molecular Probes). Gels were transferred to nitrocellulose membranes in 6×SSC (or to GeneScreen for EGO-B) and hybridized overnight at 42° in 50% formamide to radiolabeled random primed EGO-A or B PCR products (see above), washed 3× in 48° 2×SSC and 2× in 55° C. 0.2×SSC, then exposed to film.

Sucrose gradients: Approximately $7 \times 10^6$ CD34+ cells were cultured for 24 h in 5 ng/ml IL-5. Cells were disrupted by Dounce homogenization and layered on a 10-50% sucrose gradient. Gradients were centrifuged for 4 hours at 38,000 rpm in a swinging bucket SW4OTi rotor. 0.5 ml fractions were collected from the bottom and total RNA was isolated by phenol/chloroform purification and ethanol precipitation. OD260 readings were taken on each fraction to determine the location of the ribosomal peaks. RNA derived from fractions was reverse transcribed to cDNA and real time PCR was performed as described.

Multiple tissue expression: Multiple tissue human cDNA panels I and II were purchased from BD Bioscience Clontech. Bone marrow cDNA was isolated from human bone marrow obtained by informed consent from normal volunteers. Bone marrow and CD34+ cell cDNA were normalized to average α-tubulin Clontech panel values and RNA levels were calculated as described above.

Plasmid construction: pSilencer 2.0-U6 (Ambion) was digested with Hind III and blunt end cloned to Mlu I/AseI digested pEGFP-Cl (Clontech). The Hind III site was not lost. The multiple cloning sites in the EGFP gene were removed by a BglII/BamHI digest and religation. This plasmid is the pSi1 Neg. Subsequently, the sequence 5' gatcccaatagaaccgcaagaaaacaactcgagttgttttcttgcggttctattttggaaa3' (SEQ ID NO: 16) was cloned into the BarHI/HIII sites to create the shRNA, plasmid pSi1 20-2, targeting EGO-A and B.

siRNA: CD34+ cells: Frozen cells were reconstituted dropwise with media and allowed to recover for one hour at 37° C., 5% CO2 in 10 parts media prior to centrifugation. Endotoxin free short hairpin plasmid DNA (1.0 ug) (Qiagen Endofree maxi kit) was electroporated into $1-2 \times 10^6$ CD34+ cells using the CD34+ Nucleofector kit and a Nucleofector device (Amaxa) using program U8. Cells were allowed to recover for 15 minutes in serum and antibiotic free media at 37° C., 5% CO2. Cells were put in a 48 well flat bottom plate and RPMI, 10% FCS and P/S were immediately added. After 18 hours 5 ng/ml IL-5 was added (time=0') and EGFP+ cells were purified on a FACS Vantage cell sorter to at least 90% purity. Approximately 100,000 cells were cultured in a single well of a 96 well round bottom plate. At the 24 hour time point (to measure EGO silencing) or the 5 day time point (to measure MBP silencing) total RNA was isolated. TF-1 cells: Cells were grown in RPMI 1640, 10% FCS and IL-5 (5ng/ml). Approximately $5 \times 10^6$ freshly cultured cells were electroporated on program T3 using the V Nucleofector kit with 1-5 µg shDNA. Cells were sorted for >90% pure GFP positive within 24 hours as above and RNA was isolated. Accession numbers: Representative cDNAs for EGO-A and B are AW970881 and BC03 9547, respectively.

b) Results (1) Gene Profiling of Early Eosinophil Development

Gene expression profiling identified transcripts expressed during early eosinophil development. Affymetrix HG-U1 33 A human microarray chips were hybridized with labeled antisense RNA amplified from CD34+human hematopoietic stem cells derived from unpooled donors and cultured for 24 hours in IL-5, an eosinophil specific cytokine, or epoietin-α as a control. Arrays were normalized by GC-RMA and increased transcript levels were analyzed using rank based statistics (Breitling 2005). The top thirty-eight ranked genes have transcript levels at least four fold higher in IL-5 treated cells compared to control (Table 1). Several interleukins, interleukin receptors and chemokine receptor transcripts are increased in response to IL-5: CXCL13, IL6, IL1 family members as well as IL12B and IL21R have increased mRNA levels. PTGS2 (COX-2), a gene involved in inflammatory prostaglandin synthesis, is also differentially upregulated. In addition, two transcription factors, WT1 and HEY increase in transcriptional expression following IL-5 treatment. One novel transcript, (Affymetrix 2223 $14_{13}x_{13}$at) is nested within an intron on the opposite strand of the inositol triphosphate receptor type 1 (ITPR1) gene (FIG. 14A). This transcript is of particular interest because of its inducible expression to high transcript levels, conservation and lack of a large open reading frame. This gene was named EGO.

(2) Conservation of EGO

Vista tracks on the UCSC (University of Santa Cruz) browser show that conservation of the region within the large intron of ITPR1 which includes the EGO gene is high among human, mouse, and chicken (FIG. 14A and B). However, the highest region of homology, close to 90% identity, is in the intron of EGO-B, suggesting an additional undiscovered gene or a regulatory region. The 3' portion of EGO-A has approximately 75% identity between mouse and human (FIG. 14B). However, no ORFs over 86 amino acids are present in EGO-A or B and amino acids are not conserved between mouse and human. Furthermore, ncRNA genes are often found within introns and untranslated regions of coding genes (Carninci 2005; Ravasi 2006). NcRNA genes are often inferred by the lack of large open reading frames or of conserved amino acid sequence. Therefore, the hypothesis that EGO is an ncRNA gene was investigated further.

(3) EGO Gene Structure

Two splice variants of the EGO transcript were found using a BLAT Search (May 2004 Assembly) (FIG. 14C). The splice variant found by array analysis is a 535 basepair cDNA (GenBank Accession # AW970881) which was named EGOA (FIG. 14C). In addition, a two exon splice variant, EGO-B, (GenBank Accession #BC39547) is 1460 bases in length (FIG. 14C). However, northern blot analysis using RNA isolated from TF-1 cells, a CD34+erythroleukemic cell line, and a probe to a unique region of EGO-A revealed a 1 kb polyadenylated transcript, showing the reported cDNA is truncated (FIG. 2). RT-PCR data is consistent with EGO-A extending over 300 bases towards the 5' end of the transcript (additional bases in the poly A tail may add 100-200 bases). Northern blot using a probe complementary to exon 2 of EGO-B (FIG. 2) shows an approximately 1700 base polyadenylated transcript, which is consistent with GenBank data for BC039547 cDNA. Sequence data shows that the 5' splice junction for EGO-B is 46 bases upstream from the reported BC039547 cDNA splice site (4767665-476655 TTCTATCAG... GCACGATGGT (SEQ ID NOS 1 and 2) (FIG. 2B). Based on the single stranded probes in the Affymetrix arrays, both EGO-A and B are sense on the —strand of genomic DNA, the opposite strand from ITPR1 transcription. The multiple overlapping transcripts derived from both strands in this region are characteristic of an RNA forest. Therefore, at least two EGO splice variants are transcribed within an intron on the opposite strand from ITPR1.

(4) Sucrose Density gradient Analysis of ncRNA

The hypothesis that EGO is an ncRNA was tested by measuring its association with ribosomes by sucrose density gradient sedimentation. Sucrose density gradient sedimentation was performed on lysates from $CD34^+$ UCB cells stimulated for 24 hours with IL-5 to determine if EGO RNA is in the ribosomal fraction. Absorbance at 260 nm per fraction gives a characteristic plot in which ribosomes are concentrated at the bottom of the sucrose gradient. In this gradient, UV absorbance in fractions 1 and 3 are indicative of polysomes and fraction 7 corresponds to single ribosomes (FIG. 3A). Real time RT-PCR was performed on each fraction for ($\alpha$-tubulin mRNA and for EGO-A and B transcript expression. As expected, $\alpha$-tubulin transcripts are mainly associated with polysomes in fraction 3 (FIG. 3B). In contrast, both EGO-A and B transcripts levels are more abundant in the lighter fractions of the gradient, especially in fraction 17 (FIGS. 3C and D). These data show that EGO transcripts are not associated with ribosomes in UCB $CD34^+$ cells in vitro after stimulation for 24 hours with IL-5.

(5) EGO Gene Expression

Figure 15A:
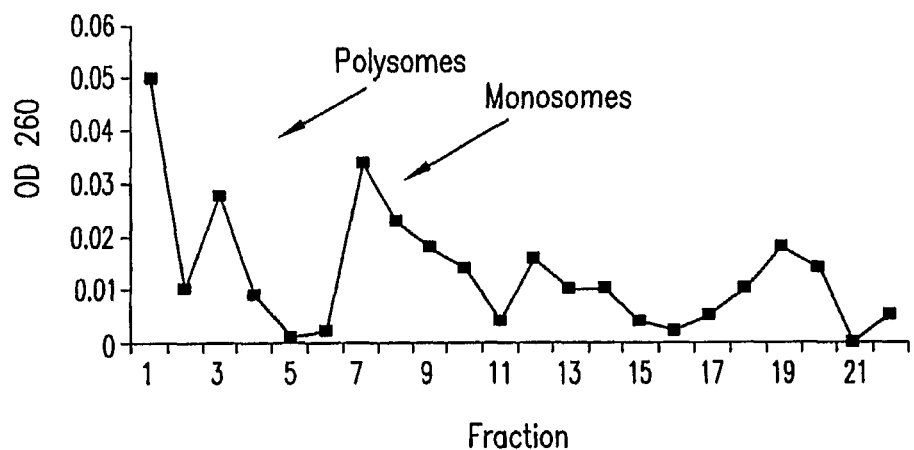
Figure 15B:
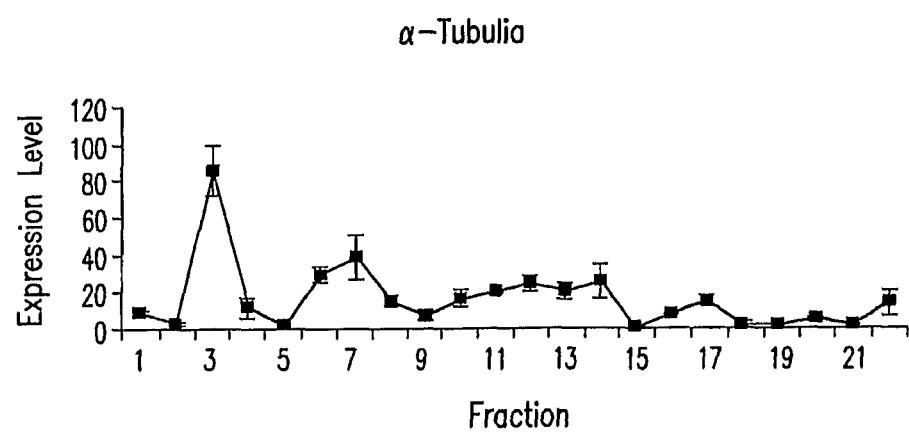
Figure 15C:
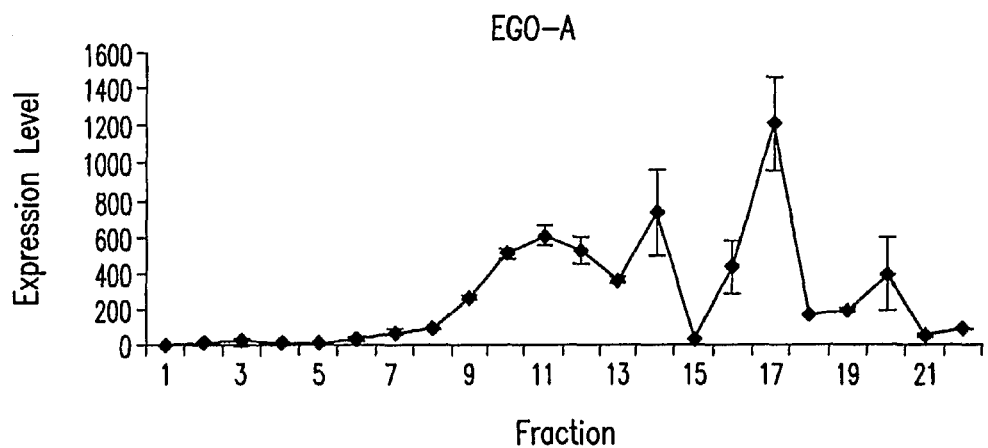
Figure 15D:
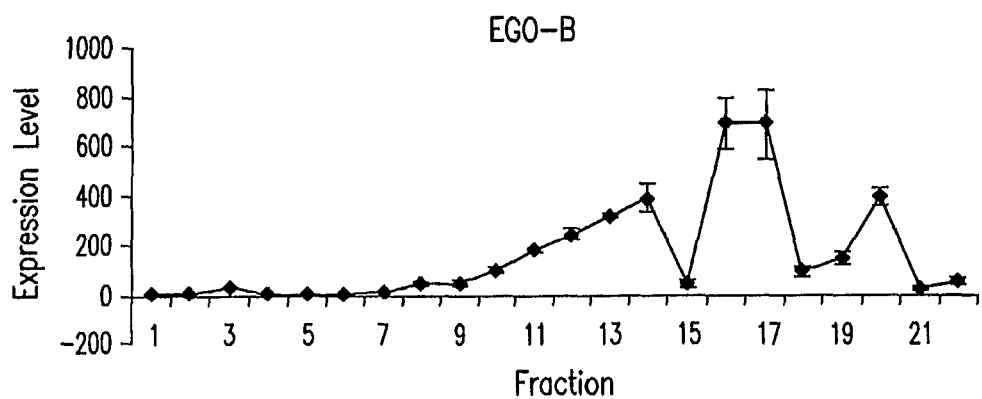

The inducible expression of EGO-A and B RNA was investigated by real time Q-RT-PCR (quantitative reverse transcriptase polymerase chain reaction) of $CD34^+$ cells derived from UCB or bone marrow and stimulated with cytokines over a time course. EGO-A and B transcripts derived from $CD34^+$ UCB cells are highly expressed, over 20 fold above the initial time point, at 6 hours after IL-5 addition, and expression is reduced to baseline levels by 72 hours after stimulation (FIGS. 15A and B). The specificity of IL-5 induced EGO RNA expression was investigated by real time Q-RT-PCR of UCB $CD34^+$ cells grown on the hematopoietic cytokines: epoietin-$\alpha$, SCF, M-CSF/GM-CSF, IL-3, or GM-CSF/G-CSF. All cytokines except SCF cause a slight increase in EGO-A and B expression, suggesting that EGO transcription may also be involved in other lineages (FIGS. 15A and B). A positive control, MBP mRNA, is increasingly expressed from 72 hours to two weeks of IL-5 stimulation of $CD34^+$ UCB cells but is not expressed in epoietin-$\alpha$ stimulated cells (FIG. 15C). Expression of EGO-A and B in IL-5 stimulated $CD34^+$ bone marrow cells follows a temporal pattern similar to UCB CD34+ cells (FIG. 15D). These results show that EGO-A and B RNA are expressed coordinately very early and briefly in eosinophil development in vitro in both UCB and bone marrow derived $CD34^+$ cells stimulated with IL-5.

Figure 16A:
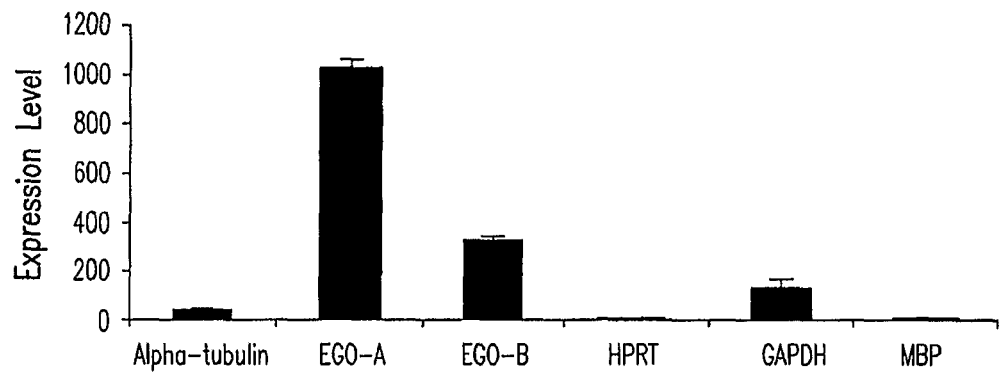
Figure 16B:
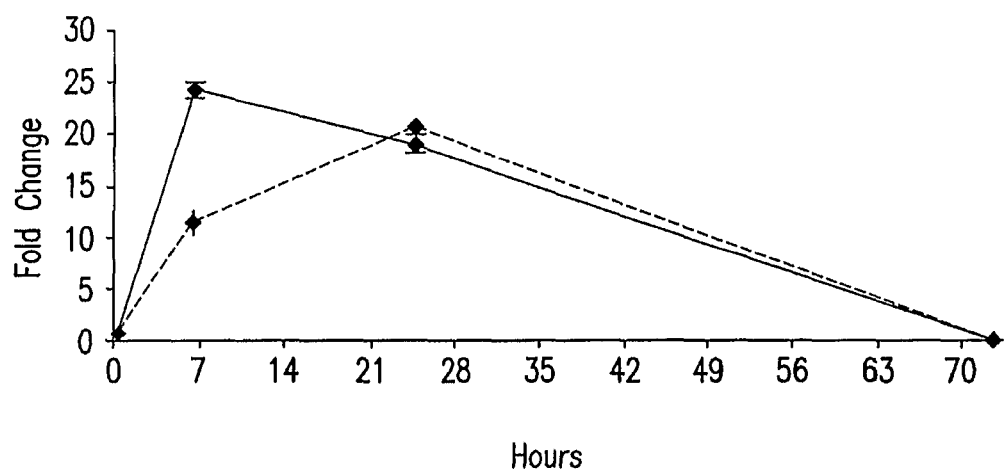

Expression levels of EGO in mature peripheral blood eosinophils were investigated. Although overall levels of RNA in mature eosinophils are low, EGO-A and B are expressed approximately 1000 fold and 300 fold higher, respectively than the transcripts for the housekeeping genes, HPRT (hypoxanthine guanine phosphoribosyl transferase), $\alpha$-tubulin, and the granule protein, MBP. GAPDH (glycerol. aldehyde phosphate dehydrogenase) mRNA is expressed at slightly higher levels, about 100 fold higher than HPRT (FIG. 16A). Eosinophils were also stimulated with IL-5 and cultured for various time points. EGO-A and B RNA are increased nearly 25 fold relative to GAPDH between 6 and 24 hours of IL-5 stimulation (FIG. 16B). Therefore, EGO is present and inducible in the mature eosinophil.

The relative expression of EGO in a panel of human tissue types was investigated by real time Q-RT-PCR. Tissue expression of both EGO-A and B RNA is 2000-7000 higher in bone marrow mononuclear cells and bone marrow $CD34^+$ cells than in brain, the tissue with the lowest expression (FIGS. 5A and B). Expression of both EGO transcripts is also high in kidney. EGO-B RNA is highly expressed in leukocytes and pancreas relative to EGO-A. The relatively high expression of EGO in bone marrow is consistent with a role for EGO in developing hematopoietic stem cells in vivo.

(6) The Role of EGO in Eosinophil Granule Protein mRNA Expression

RNA silencing experiments were initiated in order to test the hypothesis that EGO expression influences eosinophil differentiation. TF-1 is a $CD34^+$ erythroleukemic cell line that expresses eosinophil granule protein mRNA and can be growth stimulated with various cytokines, including IL-5. A short hairpin RNA (shRNA) expression plasmid containing either scrambled control sequences (pSi1 Neg) or sequences simultaneously targeting both variants of EGO (pSi1 20-2) for silencing were transfected into TF-1 cells. Plasmids also contained an enhanced green fluorescent protein (EGFP) reporter gene. TF-1 cells were sorted to at least 90% purity for $EGFP^+$ cells 24 hours after transfection. Real time Q-RT-PCR of RNA isolated from $EGFP^+$ cells was used to quantitate silenced levels of EGO RNA using primers spanning the putative RNA cut site and $\alpha$-tubulin primers as a control. Levels of EGO are diminished to 13% (87% knockdown) in the cells transfected with the shRNA plasmid directed at EGO transcripts compared to the negative control (FIG. 17A). Levels of MBP and EDN mRNA, which are constitutively expressed in TF-1 cells, were also measured by Q-RT-PCR (eosinophil peroxidase mRNA is not expressed). In cells in which EGO transcripts have been silenced, levels of MBP mRNA are 9% of control, and EDNRNA levels are 4% of control levels, however, GAPDH mRNA levels and the GA TA-1 transcription factor mRNA levels remain relatively unchanged (FIG. 17A). Repeated experiments in TF-1 cells show similar results with variations in transcript levels (Table 8). This shows that diminished EGO RNA levels decrease transcript levels of the eosinophil granule proteins MBP and EDN.

Figure 5B:
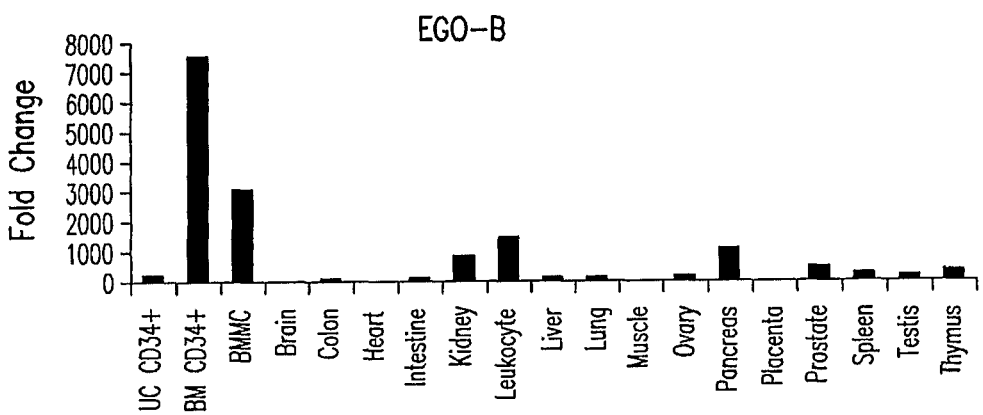

$CD34^+$ cells derived from UCB are a better model of eosinophil differentiation than TF-1 cells, because IL-5 stimulated CD34+ UCB cells develop into eosinophils whereas TF-1 cells simply proliferate in response to a variety of cytokines. $CD34^+$ UCB cells express MBP mRNA at 72 hours after IL-5 stimulation and have immature granules at 1 week; however, electroporated cells are fragile and have incomplete development, dying after 5 days. $CD34^+$ cells were transfected with shRNA plasmids, sorted for >90% pure EGFP+ cells less than 24 hours after transfection and grown for 5 days on IL-5. Silencing reduced EGO transcripts to 38% of control (62% knockdown) at 24 hours after IL-5 stimulation (FIG. 5B). RNA was isolated and Q-RT-PCR performed to quantitate granule protein mRNA levels. MBP mRNA levels are reduced to 27% in EGO silenced cells as compared to controls and levels of EDNmRNA are 59% of control levels (FIG. 5B). In contrast, GAPDH levels are increased in response to EGO silencing (FIG. 5B). GATA-1 is expressed at very low levels in $CD34^+$ cells and can not be reliably measured. These data show that EGO RNA is necessary for normal MBP and EDN transcript levels during eosinophilopoiesis.

c) Discussion

Genes expressed in early eosinophil development were investigated by transcriptional profiling of $CD34^+$ cells stimulated with IL-5. Increases in inflammatory cytokines, cytokine receptors and chemokine ligand transcript expression were shown. Included in the differentially expressed proinflammatory molecules are: IL6, IL1F9, CCL19, CCL1, CCL6, PTGS2 (COX-2), IL12B, IL21R, EBI3, IL1RL1 and IL1 7RB. IL12B promoter polymorphism has been linked with asthma severity and atopic dermatitis (Morahan 2002; Tsunemi 2002) and IL21R is associated with rheumatoid arthritis (Jungel 2004). Of particular interest is the increased expression of the HEY1 (hairy enhancer of split) transcription factor. HEY1 is reported to physically interact with GA TA-1 to decrease its activity (Elagib 2004). An intermediate level of GA TA-1 is instrumental in eosinophil development; therefore, HEY1 can be the effector molecule that maintains these critical levels. Furthermore, the results show that, EGO, a transcript nested within an intron on the opposite strand of ITPR1, also increases in response to IL-5. However, ITPR1 mRNA levels do not increase following IL-5 stimulation (Table 1). RNA silencing, sucrose density gradient and gene expression experiments show that EGO is an ncRNA necessary for normal eosinophil granule protein transcript levels of MBP and EDN.

EGO is nested within a conserved intron of the ITPR1 gene. At least half of transcripts in mammals are non-coding and many ncRNAs are found in introns or in the 3' untranslated regions of coding genes. Approximately 158 coding nested genes have been identified in the human genome (Yu 2005). Conservation of the ITPRI intron containing EGO is higher than most ITPRI exons, with up to 900/0 identity among mouse, human and chicken. EGO-A and the 5' exon of EGO-B have up to 75% identity between human and mouse, reflecting evolutionary pressure and a possible functional role for these transcripts. However, the highest conservation is within the intron of EGO-B, showing an additional transcript or a regulatory region (FIG. 14). Q-RT-PCR shows that the intron of EGO-B is highly expressed, but not inducible with IL-5, further suggesting an undiscovered transcript in this region. Also, in support of an additional transcript, northern blot data shows a 2 kb transcript when probed with the intron of EGO-B. These data show that EGO resides in a highly transcribed region of the genome and has likely been retained by natural selection for a functional role.

The lack of a large open reading frame and poor amino acid conservation of small open reading frames of fewer than 100 amino acids show that EGO is an ncRNA. Furthermore, EGO transcripts are not associated with ribosomes in vitro, although translated mRNA, such as αtubulin, is present in the polyribosome fraction of the sucrose gradient, as expected. EGO-A and B are present in less dense, non-ribosomal fractions of the sucrose gradient. As most, if not all RNAs, are associated with proteins, it is likely that EGO-A and B are bound to proteins. Although, the translationally controlled expression of a small protein at discrete intervals in hematopoietic development is possible, the simplest explanation for the data is that EGO does not code for a protein.

Tissue specific expression and inducible expression of ncRNA suggests functionality. Expression of EGO RNA is rapidly and transiently increased following IL-5 addition to CD34+ hematopoietic cell culture derived from UCB, bone marrow or mature eosinophils. EGO RNA is very highly expressed in bone marrow; however, EGO transcript levels were not high in thymus cDNA, showing that EGO does not have a role in lymphoid development. The high, tissue specific expression of EGO in bone marrow shows a role in development from bone marrow hematopoietic stem cells.

The fiunctional role of EGO was investigated by RNA silencing. TF-1, a CD34+ cell line, which is cytokine growth dependent and CD34+ UCB cells were used to evaluate the effect of EGO RNA silencing on eosinophil development. TF-1 cells express EGO and granule protein mRNA constitutively during growth on a variety of cytokines. Silencing of EGO transcripts in TF-1 and CD34+ cells decreases the level of MBP and EDNmRNA; however, GA TA-1 levels were not affected in TF-1 cells, showing a GA TA-1 independent mechanism. Therefore, EGO is an ncRNA which is expressed during IL-5 stimulation of CD34+ UCB cells, is present in bone marrow mononuclear cells and regulates granule protein MBP and EDN mRNA levels.

TABLE 8

EGO silencing in TF-1 cells. Percentage of transcripts in silenced cells compared to controls.

| Experiment | Plasmid | EGO | MBP | EDN | GAPDH | GA TA-1 |
|---|---|---|---|---|---|---|
| 1 | pSil Neg | 100 | 100 | 100 | 100 | nd* |
|  | pSil 20-2 | 13 | 30 | 7 | 113 | nd |
| 2 | pSil Neg | 100 | 100 | nd | 100 | nd |
|  | pSil 20-2 | 40 | 64 | nd | 73 | nd |
| 3 | pSil Neg | 100 | 100 | 100 | nd | nd |
|  | pSil 20-2 | 35 | 21 | 61 | nd | nd |
| 4 | pSil Neg | 100 | 100 | 100 | 100 | 100 |
|  | pSil 20-2 | 32 | 85 | 75 | 76 | 97 |
| 5 | pSil Neg | 100 | 100 | 100 | 100 | 100 |
|  | pSil 20-2 | 13 | 9 | 4 | 66 | 135 |
| 6 | pSil Neg | 100 | 100 | 100 | 100 | 100 |
|  | pSil 20-2 | 46 | 74 | 16 | 85 | 99 |

*nd not determined

G. REFERENCES

1. Kita, H., Adolphson, C. R. & Gleich, G. J. in Middleton's Allergy: Principles & Practice (eds. Adkinson, N. F., Jr. et al.) 305-332 (Mosby, Philadelphia, 2003).
2. Lee, J. J. et al. Defining a Link with Asthma in Mice Congenitally Deficient in Eosinophils. Science 305, 1773-6 (2004).
3. Humbles, A. A. et al. A Critical Role for Eosinophils in Allergic Airways Remodeling. Science 305, 1776-9 (2004).
4. McNagny, K. & Graf, T. Making eosinophils through subtle shifts in transcription factor expression. J Exp Med 195, F43-7 (2002).
5. Nerlov, C., McNagny, K. M., Doderlein, G., Kowenz-Leutz, E. & Graf, T. Distinct C/EBP functions are required for eosinophil lineage commitment and maturation. Genes Dev 12, 2413-23 (1998).
6. Hirasawa, R. et al. Essential and instructive roles of GATA factors in eosinophil development. J Exp Med 195, 1379-86 (2002).
7. Zhang, D. E. et al. Absence of granulocyte colony-stimulating factor signaling and neutrophil development in CCAAT enhancer binding protein alpha-deficient mice. Proc Natl Acad Sci U S A 94, 569-74 (1997).
8. Nerlov, C. & Graf, T. PU.1 induces myeloid lineage commitment in multipotent hematopoietic progenitors. Genes Dev 12, 2403-12 (1998).
9. Okazaki, Y. et al. Analysis of the mouse transcriptome based on functional annotation of 60,770 full-length cDNAs. Nature 420, 563-73 (2002).
10. Du, J. et al. Novel combinatorial interactions of GATA-1, PU.1, and C/EBPepsilon isoforms regulate transcription of the gene encoding eosinophil granule major basic protein. J Biol Chem 277, 43481-94 (2002).
11. Gombart, A. F. et al. Regulation of neutrophil and eosinophil secondary granule gene expression by transcription factors C/EBP epsilon and PU.1. Blood 101, 3265-73 (2003).

12. Yamaguchi, Y. et al. Mechanisms of transcription in eosinophils: GATA-1, but not GATA-2, transactivates the promoter of the eosinophil granule major basic protein gene. Blood 91, 3447-58 (1998).
13. Zimmermann, N., Colyer, J. L., Koch, L. E. & Rothenberg, M. E Analysis of the CCR3 promoter reveals a regulatory region in exon 1 that binds GATA-1. BMC Immunol 6, 7 (2005).
14. Yamanaka, R. et al. Impaired granulopoiesis, myelodysplasia, and early lethality in CCAAT/enhancer binding protein epsilon-deficient mice. Proc Natl Acad Sci U S A 94, 13187-92 (1997).
15. Querfurth, E. et al. Antagonism between C/FBPbeta and FOG in eosinophil lineage commitment of multipotent hematopoietic progenitors. Genes Dev 14, 2515-25 (2000).
16. Buitenhuis, M. et al. Differential regulation of granulopoiesis by the basic helix-loop-helix transcriptional inhibitors Id1 and Id2. Blood 105, 4272-4281 (2005).
17. Ema, H. et al. Target cells for granulocyte colony-stimulating factor, interleukin-3, and interleukin-5 in differentiation pathways of neutrophils and eosinophils. Blood 76, 1956-61 (1990).
18. Lee, N. A. et al. Expression of IL-5 in thymocytes/T cells leads to the development of a massive eosinophilia, extramedullary eosinophilopoiesis, and unique histopathologies. J Immunol 158, 1332-44 (1997).
19. Dent, L. A., Strath, M., Mellor, A. L. & Sanderson, C. J. Eosinophilia in transgenic mice expressing interleukin 5. J Exp Med 172, 1425-31 (1990).
20. Tominaga, A. et al. Transgenic mice expressing a B cell growth and differentiation factor gene (interleukin 5) develop eosinophilia and autoantibody production. J Exp Med 173, 429-37 (1991).
21. Kopf, M. et al. IL-5-deficient mice have a developmental defect in CD5+B-1 cells and lack eosinophilia but have normal antibody and cytotoxic T cell responses. Immunity 4, 15-24 (1996).
22. Foster, P. S., Hogan, S. P., Ramsay, A. J., Matthaei, K. I. & Young, I. G. Interleukin 5 deficiency abolishes eosinophilia, airways hyperreactivity, and lung damage in a mouse asthma model. J Exp Med 183, 195-201 (1996).
23. Kitagaki, H. et al. Repeated elicitation of contact hypersensitivity induces a shift in cutaneous cytokine milieu from a T helper cell type 1 to a T helper cell type 2 profile. J Inmunol 159, 2484-91 (1997).
24. Shi, H. Z. et al. Effect of inhaled interleukin-5 on airway hyperreactivity and eosinophilia in asthmatics. Am J Respir Crit Care Med 157, 204-9 (1998).
25. Iwasaki, H. et al. Identification of eosinophil lineage-committed progenitors in the murine bone marrow. J Exp Med 201, 1891-7 (2005).
26. Claverie, J. M. Fewer genes, more noncoding RNA. Science 309, 1529-30 (2005).
27. Carninci, P. et al. The transcriptional landscape of the mammalian genome. Science 309, 1559-63 (2005).
28. Ravasi, T. et al. Experimental validation of the regulated expression of large numbers of non-coding RNAs from the mouse genome. Genome Res 16, 11-9 (2006).
29. Willingham, A. T. et al. A strategy for probing the function of noncoding RNAs finds a repressor of NFAT. Science 309, 1570-3 (2005).
30. Breitling, R. & Herzyk, P. Rank-based methods as a non-parametric alternative of the T-statistic for the analysis of biological microarray data. J Bioinform Comput Biol 3, 1171-89 (2005).
31. Morahan, G. et al. Association of IL12B promoter polymorphism with severity of atopic and non-atopic asthma in children. Lancet 360, 455-9 (2002).
32. Tsunemi, Y. et al. Interleukin-12 p 40 gene (IL12B) 3'-untranslated region polymorphism is associated with susceptibility to atopic dermatitis and psoriasis vulgaris. J Dermatol Sci 30, 161-6 (2002).
33. Jungel, A. et al. Expression of interleukin-21 receptor, but not interleukin-21, in synovial fibroblasts and synovial macrophages of patients with rheumatoid arthritis. Arthritis Rheum 50, 1468-76 (2004).
34. Elagib, K. E. et al. Jun blockade of erythropoiesis: role for repression of GATA-1 by HERP2. Mol Cell Biol 24, 7779-94 (2004).
35. Yu, P., Ma, D. & Xu, M. Nested genes in the human genome. Genomics 86, 414-22 (2005).
36. Bernard, P. S. & Wittwer, C. T. Real-time PCR technology for cancer diagnostics. Clin Chem 48, 1178-85 (2002).
37. Siqueira, J., Costa J., Cordiero, R., Serra, M., Silva, P., Martins, M. Local anesthetic medication for the treatment of asthma. Mem Inst Oswaldo Cruz, 2005. 100(1):161-165.
38. Roquet, A., et al. Combined antagonism of leukotrienes and histamine produces predominant inhibition of allergen-induced early and late phase airway obstruction in asthmatics. Am J respire Crit Care Med, 1997. 155(6): 1956-63.
39. Kita H., C.R. Adolphson, and G.J Gleich. Allergy, Principles and Practice. 6 ed. Allergy, ed. NF. Adkinson, et al. Vol 1. 2003, Philadelphia: Mosby.
40. Leckie, M. J., et al. Effects of an interleukin-5 blocking monoclonal antibody on eosinophils, airway hyper-responsiveness, and the late asthmatic response. Lancet, 2000. 356(9248): 2144-8.
41. Therapeutic and adverse effects of glcocorticoids.
42. Hunt, L. W., H. A. Swedlund, and G. J. Gleich. Effect of nebulized lidocaine on severe glucocorticoid-dependent asthma. Mayo Clin Proc, 1996. 71(4): 361-8.
43. Decco, M. L., et al. Nebulized lidocaine in the treatment of severe asthma in children: a pilot study. Ann Allergy Asthma Immnunol, 1998. 160(8): 4010-7.
44. Hunt, L. W., et al. treatment of asthma with nebulized lidocaine: a randomized, placebo-controlled study. J Allergy Clin Immunol, 2004. 113(5): 853-9.
45. Bokesh, P. M., C. Post, and G. Strichartz. Structure-activity relationship of lidocaine homologs producing tonic and frequency dependent impulse blockade in nerve. J 46
46. Haeseler, G., et al. Block of voltage-operated sodium charnels by 2,6-dimethylphenol, a structural analogue of lidocaine's aromatic tail. Br J Pharmacol, 2002.137(2): 285-93.
47. Wagner, L. E., 2nd, et al. Meperidine and lidocaine block of recombinant voltage-dependent Na+ channels: evidence that meperidine is a local anesthetic. Anesthesiology, 1999. 91(5): 1481-1490.
48. Rolf, S., et al. Effects of antiarrhythmic drugs on cloned cardiac voltage-gated potassium channels expressed in Xenopus oocytes. Naunyn Schmiedebergs Arch Pharmacol, 2000. 362(1): 22-31.
49. Scheuer, T. Commentary: A Revised View of Local Anesthetic Action: What Channel State Is Really Stabilized? J Gen Physiol, 1999. 113(1): 3-6.
50. Groben, H., et al. Airway anesthesia alone does not explain attenuation of histamine-induced bronchospasm by local anesthetics: a comparison of lidocaine, ropivacaine, and dyclonine. Anesthesiology, 2001.17(11): 672-679.
51. Okada, S., et al. Lidocaine and its analogues inhibit IL-5-mediated survival and activation of human eosinophils. J Immunol, 1998. 160(8): 4010-4017.
52. Usami, A., et al. Theophylline and dexamethasone induce peroxisome proliferator-activated receptor-gamma expression in human eosinophils. Pharmacology. 2006. 77(1):33-37.
53. Humbles, A. A., et al., A critical role for eosinophils in allergic airways remodeling. Science, 2004.305(5691): 1776-9.
54. Lee, J. J., et al., Defining a link with asthma in mice congenitally deficient in eosinophils. Science, 2004. 305: 1773-6.
55. Simon, H U. Molecules involved in the regulation o eosinophil apoptosis. Chem Immunol Allergy, 2006. 91:49-58.
56. Cockcroft, D. W., Pharmacologic Therapy for Asthma: Overview and Historical Perspective. J Clin Pharmacol, 1999.35:219-222.
57. Rizzo, M. C., Sole, D., Inhaled corticosteroids in the treatment of respiratory allergy: safety vs. efficacy. J Pediatr, 2006. 82(2): S198-205.
58. Kitamura, T., Tange, T., Terasawa, T., Chiba, S., Kuwaki, T., Miyagawa, K., Piao, Y F., Miyazono, K., Urabe, A., Takaku, F. Establishment and characterization of a unique human cell line that proliferates dependently on GM-CSF, IL-3, or erythropoietin. J Cell Physiol, 1989. 140(2): 323-334.
59. da Costa, J., Olsen, P., De Azereredo Siqueira, R., De Frias Carcalho, V., Serra, M., Alves, L., Faria, R., Xisto, D., Rocco, P., Cordeiro, R., Rodrigues, E., Silva, P., Martins, M. JMF-2, a lidocaine derivative acting on airways spasm and lung allergic inflammation in rats. J Allergy Clin Immunol, 2007. 119(1):219-25.

What is claimed is:

1. A method of inhibiting or reducing eosinophil development in a subject comprising reducing Eosinophil Granule Ontogeny mRNA levels in the subject, wherein reducing Eosinophil Granule Ontogeny mRNA levels comprises administering to the subject an inhibitor of Eosinophil Granule Ontogeny.

2. The method of claim 1, wherein the inhibitor of Eosinophil Granule Ontogeny is a viral vector, wherein delivery of the vector to a cell inhibits eosinophil development.

3. The method of claim 2, wherein the vector comprises a nucleic acid operably linked to an expression control sequence and wherein the nucleic acid inhibits eosinophil development.

4. The method of claim 1, wherein the subject has asthma, a skin disease, atopic dermatitis, urticaria, drug reactions, reactions to insect stings, cutaneous T-cell lymphoma (CTCL), Eosinophilia Myalgia Syndrome, Toxic Oil Syndrome, eosinophilic esophagitis, or Hypereosinophilic Syndrome.

5. The method of claim 1, wherein the inhibitor of Eosinophil Granule Ontogeny is a functional nucleic acid.

6. The method of claim 5, wherein the functional nucleic acid is siRNA.

7. The method of claim 6, wherein the siRNA targets EGO-A, EGO-B, or parts thereof.

8. The method of claim 6, wherein the siRNA targets EGO-A, EGO-B, or parts of EGO-A and EGO-B.

9. The method of claim 6, wherein the siRNA is SEQ ID NO: 16.

* * * * *

UNITED STATES PATENT AND TRADEMARK OFFICE
CERTIFICATE OF CORRECTION

PATENT NO. : 9,012,419 B2  
APPLICATION NO. : 12/300894  
DATED : April 21, 2015  
INVENTOR(S) : Lori A. Wagner et al.

Page 1 of 1

It is certified that error appears in the above-identified patent and that said Letters Patent is hereby corrected as shown below:

IN THE SPECIFICATION

In column 1, lines 12-14, replace "This invention was made with government support under Public Health Service Grant R01 AI009728. The government has certain rights in this invention." with -- This invention was made with government support under grant number R01 AI009728 awarded by National Institutes of Health. The government has certain rights in this invention. --

Signed and Sealed this
First Day of December, 2015

Michelle K. Lee
*Director of the United States Patent and Trademark Office*

SEQUENCE LISTING

```
<160> NUMBER OF SEQ ID NOS: 16

<210> SEQ ID NO 1
<211> LENGTH: 9
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 1 ttctatcag                                                                 9

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 2
gcacgatggt                                                               10

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 3
cttctcctcc aggccatacc                                                    20

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 4
ccattgtgta gccccg                                                        16

<210> SEQ ID NO 5
```

```
<211> LENGTH: 18
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 5
ccatcgtgcc tgatagaa                                                         18

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 6
caccatggtt ccaaaactgt tca                                                   23

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 7
gtttttccat cgccgtt                                                          17

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 8
gggattgcgg tacttataca                                                       20

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 9
atgggctcag ctagtt                                                           16

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 10
aggaattatg attgtggggt                                                       20

<210> SEQ ID NO 11
<211> LENGTH: 20
```

```
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 11
ggtatggcct ggaggagaag                                                   20

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 12
tctctgctcc tcctgtt                                                      17

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 13
caagcttccc gttctca                                                      17

<210> SEQ ID NO 14
<211> LENGTH: 16
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 14
ggactctcct ccccag                                                       16

<210> SEQ ID NO 15
<211> LENGTH: 16
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 15
ctgaattgag ggggct                                                       16

<210> SEQ ID NO 16
<211> LENGTH: 64
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 16
gatcccaata gaaccgcaag aaaacaactc gagttgtttt cttgcggttc tattttttg        60 gaaa                                                                    64
```